(12) United States Patent
Blanco-Pillado et al.

(10) Patent No.: US 8,642,768 B2
(45) Date of Patent: Feb. 4, 2014

(54) DIMETHYL-BENZOIC ACID COMPOUNDS

(71) Applicant: Eli Lilly and Company, Indianapolis, IN (US)

(72) Inventors: Maria-Jesus Blanco-Pillado, Fishers, IN (US); Matthew Joseph Fisher, Mooresville, IN (US); Steven Lee Kuklish, Fishers, IN (US); Tatiana Natali Vetman, Greenwood, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/922,277

(22) Filed: Jun. 20, 2013

(65) Prior Publication Data

US 2014/0005222 A1    Jan. 2, 2014

Related U.S. Application Data

(60) Provisional application No. 61/778,969, filed on Mar. 13, 2013, provisional application No. 61/665,956, filed on Jun. 29, 2012.

(51) Int. Cl.
*C07D 211/68* (2006.01)
*A61K 31/445* (2006.01)

(52) U.S. Cl.
USPC .......................... 546/193; 514/318

(58) Field of Classification Search
USPC .......................... 546/193; 514/318
See application file for complete search history.

(56) References Cited

U.S. PATENT DOCUMENTS

| | | | |
|---|---|---|---|
| 7,705,035 | B2 | 4/2010 | Boyd et al. |
| 2005/0256170 | A1 | 11/2005 | Oxford et al. |
| 2011/0288100 | A1 | 11/2011 | Sun |
| 2012/0083463 | A1 | 4/2012 | Maue et al. |

FOREIGN PATENT DOCUMENTS

| | | |
|---|---|---|
| WO | 9602509 A1 | 2/1996 |
| WO | 2012117097 A1 | 9/2012 |

*Primary Examiner* — John Mabry

(74) *Attorney, Agent, or Firm* — Nelsen L. Lentz

(57) ABSTRACT

The present invention provides a compound of the Formula II:

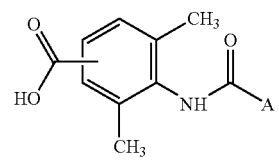

Formula II wherein A is:

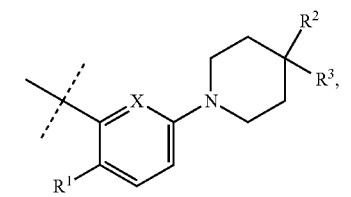

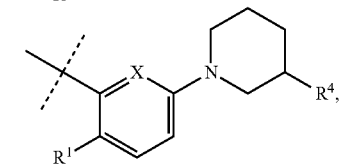

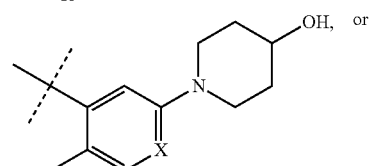

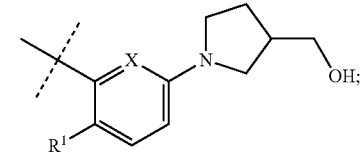

$R^1$ is $CH_3$, $CF_3$, or F;
$R^2$ is H, $CH_3$, or F;
$R^3$ is $CH_3$, $OCH_3$, OH, F;
$R^4$ is OH or $CH_2OH$; and
X is CH or N;
or a pharmaceutically acceptable salt thereof.

13 Claims, No Drawings

DIMETHYL-BENZOIC ACID COMPOUNDS

The present invention relates to novel dimethyl-benzoic acid compounds, to pharmaceutical compositions comprising the compounds, to methods of using the compounds to treat physiological disorders, and to intermediates and processes useful in the synthesis of the compounds.

The present invention is in the field of treatment of inflammatory conditions, such as arthritis, including osteoarthritis and rheumatoid arthritis, and further including pain associated with these conditions. Arthritis affects millions of patients in the United States alone and is a leading cause of disability. Treatments often include NSAIDs (nonsteroidal anti-inflammatory drugs) or COX-2 inhibitors, which may produce untoward cardiovascular side effects. As such, patients who have a poor cardiovascular profile, such as hypertension, may be precluded from using NSAIDs or COX-2 inhibitors. Thus, there is a need for an alternative treatment of osteoarthritis and rheumatoid arthritis, preferably without the side effects of the current treatments.

Four prostaglandin $E_2$ ($PGE_2$) receptor subtypes have been identified as the following: EP1, EP2, EP3 and EP4. It has been disclosed that EP4 is the primary receptor involved in joint inflammatory pain in rodent models of rheumatoid arthritis and osteoarthritis (See *J. Pharmacol. Exp. Ther.*, 325, 425 (2008)). Hence, a selective EP4 antagonist may be useful in treating arthritis, including arthritic pain. In addition, it has been suggested that since EP4 antagonism does not interfere with biosynthesis of prostanoids, such as $PGI_2$ and $TxA_2$, a selective EP4 antagonist may not possess the potential cardiovascular side effects seen with NSAIDs and COX-2 inhibitors. (See for example *Bioorganic & Medicinal Chemistry Letters*, 21, 484 (2011)).

WO 96/02509 discloses certain quinoline derivatives which are selective, non-peptide NK3 antagonists useful in treating a variety of disorders including, for example, pulmonary disorders, CNS disorders, neurogenic inflammation, and inflammatory pain. In addition, U.S. Pat. No. 7,705,035 discloses certain indoline amide derivatives useful as EP4 ligands, agonists, or antagonists useful in treating various disorders, such as osteoarthritis, rheumatoid arthritis, and acute and chronic pain.

The present invention provides certain novel compounds that are selective inhibitors of EP4 relative to EP1, EP2, and EP3. In addition, the present invention provides certain novel compounds with the potential for reduced cardiovascular or gastrointestinal side effects in comparison to traditional NSAIDs.

Accordingly, the present invention provides a compound of the Formula II:

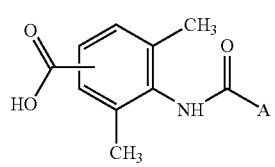

Formula II wherein A is:

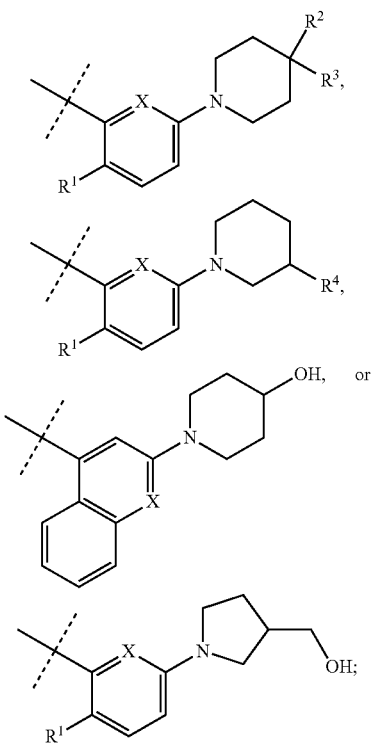

$R^1$ is $CH_3$, $CF_3$, or F;
$R^2$ is H, $CH_3$, or F;
$R^3$ is $CH_3$, $OCH_3$, OH, F;
$R^4$ is OH or $CH_2OH$; and
X is CH or N;
or a pharmaceutically acceptable salt thereof.

The present invention further provides a compound of the Formula I:

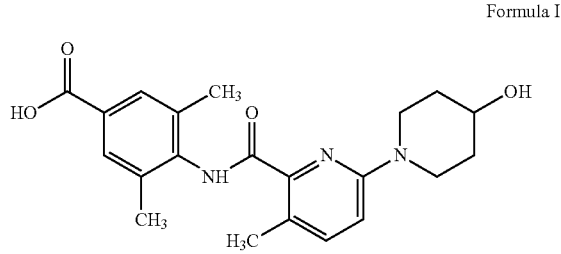 [SMILES: Cc1ccc(N2CCC(O)CC2)nc1C(=O)Nc1c(C)cc(C(=O)O)cc1C]

Formula I or a pharmaceutically acceptable salt thereof.

The invention further provides a hydrated compound of Formula I.

The present invention also provides a method of treating arthritis in a patient, comprising administering to a patient in need of such treatment an effective amount of a compound of Formula I or Formula II, or a pharmaceutically acceptable salt thereof. The present invention also provides a method of treating osteoarthritis in a patient, comprising administering to a patient in need of such treatment an effective amount of a compound of Formula I or Formula II, or a pharmaceutically acceptable salt thereof. In addition, the present invention provides a method of treating rheumatoid arthritis in a patient, comprising administering to a patient in need of such treatment an effective amount of a compound of Formula I or Formula II, or a pharmaceutically acceptable salt thereof. The present invention also provides a method of treating pain associated with arthritis in a patient, comprising administering to a patient in need of such treatment an effective amount of a compound of Formula I or Formula II, or a pharmaceutically acceptable salt thereof. The present invention further provides a method of treating pain associated with osteoarthritis or rheumatoid arthritis in a patient, comprising administering to a patient in need of such treatment an effective amount of a compound of Formula I or Formula II, or a pharmaceutically acceptable salt thereof.

Furthermore, the invention provides a compound of Formula I or Formula II, or a pharmaceutically acceptable salt thereof for use in therapy, in particular for the treatment of osteoarthritis. In addition, the invention provides a compound of Formula I or Formula II, or a pharmaceutically acceptable salt thereof for use in the treatment of rheumatoid arthritis. The invention also provides a compound of Formula I or Formula II, or a pharmaceutically acceptable salt thereof for use in the treatment of pain associated with osteoarthritis or rheumatoid arthritis. Furthermore, the invention provides the use of a compound of Formula I or Formula II, or a pharmaceutically acceptable salt thereof, for the manufacture of a medicament for the treatment of osteoarthritis. The invention provides the use of a compound of Formula I or Formula II, or a pharmaceutically acceptable salt thereof, for the manufacture of a medicament for the treatment of rheumatoid arthritis. The present invention also provides the use of a compound of Formula I or Formula II, or a pharmaceutically acceptable salt thereof, for the manufacture of a medicament for the treatment of pain associated with osteoarthritis or rheumatoid arthritis.

The invention further provides a pharmaceutical composition comprising a compound of Formula I or Formula II, or a pharmaceutically acceptable salt thereof, in combination with one or more pharmaceutically acceptable carriers, diluents, or excipients. In a particular embodiment, the composition further comprises one or more other therapeutic agents. This invention also encompasses novel intermediates and processes for the synthesis of the compound of Formula I or Formula II, or a pharmaceutically acceptable salt thereof.

In addition, the invention includes a method of treating inflammatory conditions such as arthritis, including osteoarthritis and rheumatoid arthritis, in a patient, comprising administering to a patient in need of such treatment an effective amount of an antagonist of a proinflammatory prostaglandin, such as an EP4 antagonist, in combination with an effective amount of a modulator of a lipoxin or resolvin receptor, such as a modulator of BLT-1, BLT-2, ALX/FPR1, GPR32, CysLT1, CysLT2, or ChemR23.

A further aspect of the invention includes a method of treating inflammatory disease such as arthritis, including osteoarthritis and rheumatoid arthritis, in a patient, comprising administering to a patient in need of such treatment an effective amount of an inhibitor of a proinflammatory prostaglandin synthase, such as an mPGES-1 inhibitor, in combination with an effective amount of a modulator of a lipoxin or resolvin receptor, such as a modulator of BLT-1, BLT-2, ALX/FPR1, GPR32, CysLT1, CysLT2, or ChemR23.

As used herein, the terms "treating" or "to treat" includes restraining, slowing, stopping, or reversing the progression or severity of an existing symptom or disorder.

As used herein, the term "patient" refers to a mammal, such as a mouse, guinea pig, rat, dog, or human. It is understood that the preferred patient is a human.

As used herein, the term "effective amount" refers to the amount or dose of the compound of the invention, or a pharmaceutically acceptable salt thereof which, upon single or multiple dose administration to the patient, provides the desired effect in the patient under diagnosis or treatment.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compound of Formula I or Formula II, or pharmaceutically acceptable salt thereof, are generally effective over a wide dosage range. For example, dosages per day normally fall within the range of about 0.01 to about 50 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the invention are preferably formulated as pharmaceutical compositions administered by any route which makes the compound bioavailable. Most preferably, such compositions are for oral administration. Such pharmaceutical compositions and processes for preparing same are well known in the art. (See, e.g., Remington: The Science and Practice of Pharmacy (D. B. Troy, Editor, 21st Edition, Lippincott, Williams & Wilkins, 2006).

It is understood that Formula II includes Formula IIa and IIb:

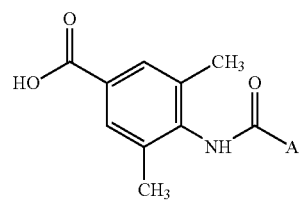

Formula IIa

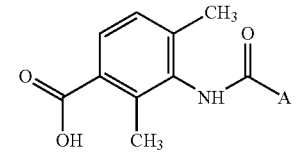

Formula IIb

The compounds of Formula I and Formula II are particularly useful in the treatment methods of the invention, but certain groups, substituents, and configurations are preferred. The following paragraphs describe such preferred groups, substituents, and configurations. It will be understood that these preferences are applicable both to the treatment methods and to the new compounds of the invention.

It is preferred that A is:

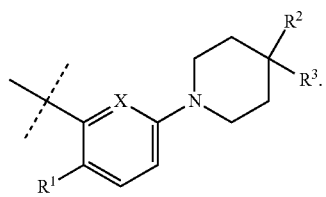

It is preferred that $R^1$ is $CH_3$.
It is preferred that X is N.
It is further preferred that when $R^2$ is H, that $R^3$ is OH.
A preferred compound is 4-[[6-(4-hydroxy-1-piperidyl)-3-methyl-pyridine-2-carbonyl]amino]-3,5-dimethyl-benzoic acid, which is:

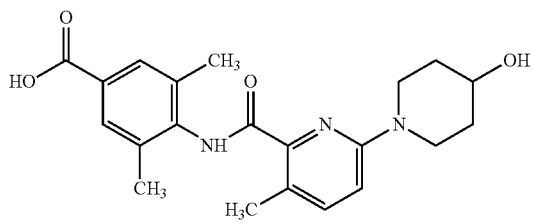 [SMILES: Cc1ccc(N2CCC(O)CC2)nc1C(=O)Nc1c(C)cc(C(=O)O)cc1C]

or a pharmaceutically acceptable salt thereof.
4-[[6-(4-hydroxy-1-piperidyl)-3-methyl-pyridine-2-carbonyl]amino]-3,5-dimethyl-benzoic acid is especially preferred.
Hydrated 4-[[6-(4-hydroxy-1-piperidyl)-3-methyl-pyridine-2-carbonyl]amino]-3,5-dimethyl-benzoic acid is further preferred.
Hydrated 4-[[6-(4-hydroxy-1-piperidyl)-3-methyl-pyridine-2-carbonyl]amino]-3,5-dimethyl-benzoic acid characterized by a substantial peak in the X-ray diffraction spectrum, at diffraction angle 2-theta, of 9.0°, in combination with two or more peaks at diffraction angle 2-theta selected from the group consisting of 5.8°, 8.5°, 9.8°, 11.6°, 11.8°, 17.5°, and 24.2°, is also preferred.
As used herein, "DMEM" refers to Dulbecco's Modified Eagle's Medium; "DMSO" refers to dimethylsulfoxide; "IPA" refers to isopropyl alcohol; "MeOH" refers to methanol; "EtOH" refers to ethanol; "DMF" refers to dimethylformamide; "THF" refers to tetrahydrofuran; "EtOAc" refers to ethyl acetate; "FBS" refers to Fetal Bovine Serum; "$PGE_2$" refers to prostaglandin $E_2$; "FBS" refers to Fetal Bovine Serum; "IBMX" refers to (3-isobutyl-1-methylxanthine); "MES" refers to (2-(N-morpholino)ethanesulfonic acid; "HEPES" refers to (2-[4-(2-hydroxyethyl)piperazin-1-yl] ethanesulfonic acid); "HTRF" refers to homogeneous time-resolved fluorescence technology; "HEK" refers to human embryonic kidney; and "$IC_{50}$" refers to the concentration of an agent that produces 50% of the maximal inhibitory response possible for that agent.

Pharmaceutically acceptable salts and common methodology for preparing them are well known in the art. See, e.g., Gould, P. L., "Salt selection for basic drugs," *International Journal of Pharmaceutics,* 33: 201-217 (1986); Bastin, R. J., et al. "Salt Selection and Optimization Procedures for Pharmaceutical New Chemical Entities," *Organic Process Research and Development,* 4: 427-435 (2000); and S. M. Berge, et al., "Pharmaceutical Salts," Journal of Pharmaceutical Sciences, 66: 1-19 (1977). One skilled in the art of synthesis will appreciate that the compound of Formula I is readily converted to and may be isolated as pharmaceutically acceptable salts using techniques and conditions well known to one of ordinary skill in the art.

The compounds of the present invention, or pharmaceutically acceptable salts thereof, may be prepared by a variety of procedures known in the art, some of which are illustrated in the schemes, preparations, and examples below. The specific synthetic steps for each of the routes described may be combined in different ways, or in conjunction with steps from different schemes, to prepare the compounds of Formula I or Formula II, or pharmaceutically acceptable salt thereof. The products of each step in the schemes below can be recovered by conventional methods, including extraction, evaporation, precipitation, chromatography, filtration, trituration, and crystallization. The reagents and starting materials are readily available to one of ordinary skill in the art. All substituents, unless otherwise specified, are as previously defined. It is understood that these schemes, preparations, and examples are not intended to be limiting to the scope of the invention in any way.

Scheme 1

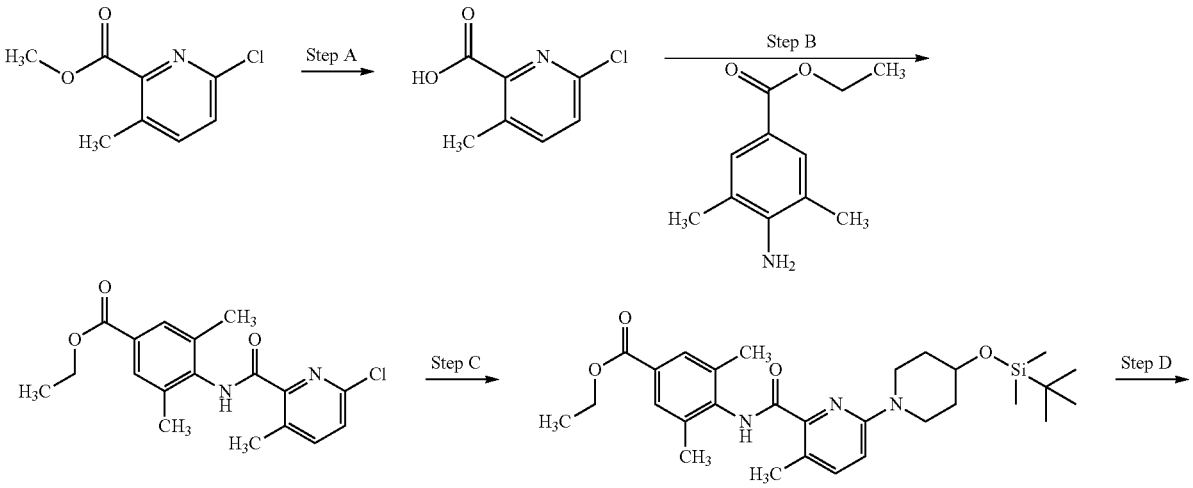

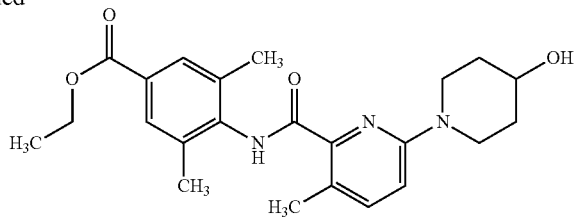

Preparation 1

Synthesis of 6-chloro-3-methyl-pyridine-2-carboxylic acid

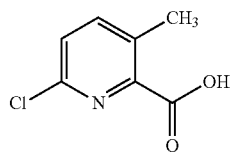

Scheme 1, step A. A solution of aqueous 1N NaOH (10 ml) is added to a stirred solution of methyl 6-chloro-3-methyl-pyridine-2-carboxylate (1.0 g, 5.39 mmoles) in THF:MeOH (10 ml:2 ml). The mixture is stirred at room temperature for 3 hours. The organic solvent is removed under reduced pressure and the semi-solid is dissolved in water and acidified to pH 1-2 with aqueous 1N HCl. The resulting precipitate is filtered, washed with water, and dried at 40° C. in a vacuum oven for 12 hours to give the title compound as a white solid (780 mg, 84%). Mass spectrum (m/z): 172.0 (M+1).

Preparation 2

Synthesis of ethyl 4-[(6-chloro-3-methyl-pyridine-2-carbonyl)amino]-3,5-dimethyl-benzoate

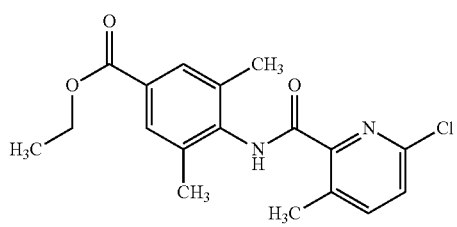 [SMILES: CCOC(=O)c1cc(C)c(NC(=O)c2nc(Cl)ccc2C)c(C)c1]

Scheme 1, step B. To a solution of 6-chloro-3-methyl-pyridine-2-carboxylic acid (0.78 g, 4.55 mmol) in CH$_2$Cl$_2$ (15 mL) at room temperature are added ethyl 4-amino-3,5-dimethyl-benzoate (0.878 g, 4.55 mmol) and N,N-diisopropylethylamine (1.98 ml, 11.36 mmol). After stirring the reaction mixture for 10 minutes, 1-propanephosphonic acid cyclic anhydride (50% solution in ethyl acetate, 3.25 ml, 5.46 mmol) is added via syringe. After 48 hours, the solvent is removed under reduced pressure and the residue is diluted with water and extracted with ethyl acetate. The organic layers are combined and dried over magnesium sulfate, filtered, and concentrated under reduced pressure. The resulting residue is purified by flash chromatography (silica gel) using a gradient of 0-40% ethyl acetate in hexanes. After purification, the solid is triturated with 30% ethyl acetate in hexanes and filtered to give the title compound as a white powder (0.907 g, 57.5%). Mass spectrum (m/z): 347.2 (M+1).

Preparation 3

Synthesis of tert-butyl-dimethyl-(4-piperidyloxy)silane

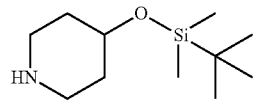

Scheme 1, step C reagent. To a solution of 4-hydroxypiperidine (2.00 g, 9.89 mmoles) in CH$_2$Cl$_2$ (30 mL) is added 1H-imidazole (2.69 g, 39.55 mmoles) followed by t-butyldimethylchlorosilane (3.58 g, 23.73 mmoles) and the reaction mixture is stirred at room temperature. After 12 hours, the reaction mixture is washed with water, saturated solution of NaHCO$_3$, and brine. The organic layers are combined and dried over sodium sulfate, filtered, and concentrated under reduced pressure. The resulting residue is purified by flash chromatography (silica gel) over a gradient using 100% CH$_2$Cl$_2$ to 10% 7N ammonia in MeOH/90% CH$_2$Cl$_2$ to afford the title compound (3.69 g, 86.3%). Mass spectrum (m/z): 216.2 (M+1).

Preparation 4

Synthesis of ethyl 4-[[6-[4-(tert-butyl(dimethyl)silyl)oxy-1-piperidyl]-3-methyl-pyridine-2-carbonyl]amino]-3,5-dimethyl-benzoate

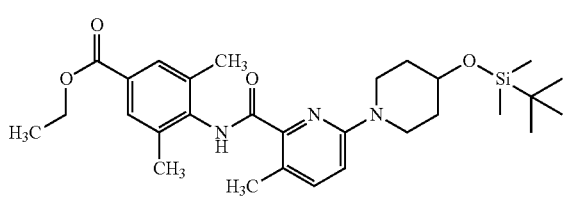 [SMILES: CCOC(=O)c1cc(C)c(NC(=O)c2nc(N3CCC(O[Si](C)(C)C(C)(C)C)CC3)ccc2C)c(C)c1]

Scheme 1, step C. To a solution of ethyl 4-[(6-chloro-3-methyl-pyridine-2-carbonyl)amino]-3,5-dimethyl-benzoate, (440 mg, 1.27 mmol) in THF (1.6 mL) is added (iPr)Pd(cinnamyl)Cl (16.43 mg, 0.03 mmol) followed by lithium bis(trimethylsilyl)amide (3.81 ml). The reaction mixture is purged with nitrogen for 5 minutes and then stirred at room temperature. After 18 hours, the reaction is diluted with a saturated solution of NaHCO$_3$ and extracted with ethyl acetate. The organic layers are combined and dried over magnesium sulfate, filtered, and concentrated under reduced pressure. The resulting residue is purified by flash chromatography (silica gel) over a gradient using 0-30% ethyl acetate in hexanes to afford the title compound (278 mg, 41%). Mass spectrum (m/z): 526.2 (M+1).

Preparation 5

Synthesis of ethyl 4-[[6-(4-hydroxy-1-piperidyl)-3-methyl-pyridine-2-carbonyl]amino]-3,5-dimethyl-benzoate

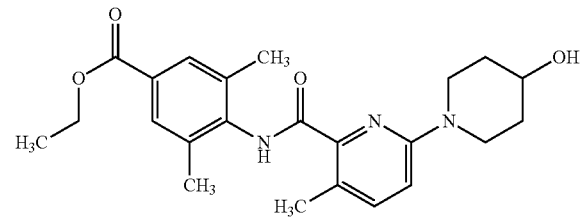 [SMILES: CCOC(=O)c1cc(C)c(NC(=O)c2nc(N3CCC(O)CC3)ccc2C)c(C)c1]

Scheme 1, step D. To a solution of ethyl 4-[[6-[4-(tert-butyl (dimethyl)silyl)oxy-1-piperidyl]-3-methyl-pyridine-2-carbonyl]amino]-3,5-dimethyl-benzoate (342 mg, 0.650 mmol) in THF (4 ml) is added Bu$_4$NF 1.0 M in THF (0.975 ml, 0.975 mmol) at 0° C. The reaction mixture is gradually warmed to ambient temperature. After 12 hours, the reaction mixture is diluted with ice-water and extracted with ethyl acetate. The organic layers are combined, dried over sodium sulfate, filtered, and concentrated under reduced pressure to give a residue. The residue is purified by flash chromatography (silica gel) over a gradient using 0-40% ethyl acetate in hexanes to afford the title compound (223 mg, 83.3%). Mass spectrum (m/z): 412.2 (M+1).

Scheme 2

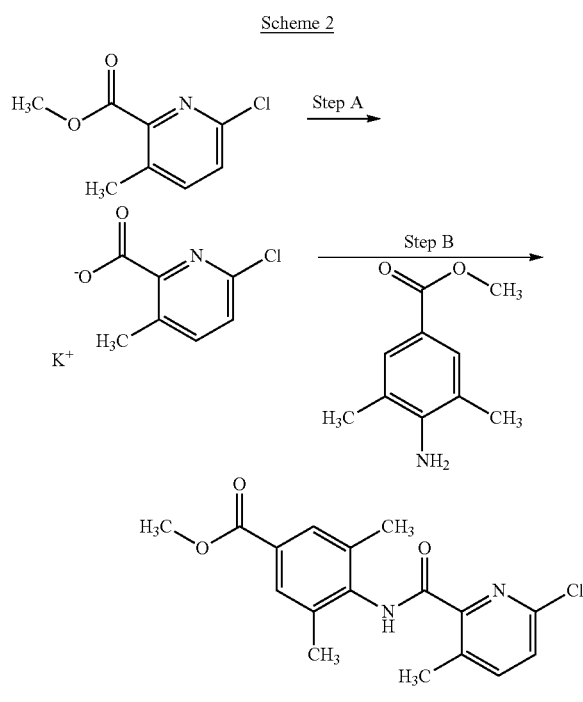

Preparation 6

Synthesis of potassium 6-chloro-3-methyl-pyridine-2-carboxylate

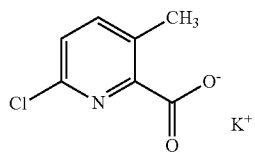

Scheme 2, step A. Methyl 6-chloro-3-methyl-pyridine-2-carboxylate (50 g, 269.4 mmoles) is added to a solution of potassium hydroxide (18.7 g, 282.9 mmoles) in isopropyl alcohol (2000 mL). The mixture is stirred at ambient temperature for 1 hour. Hexanes (500 mL) are added, and the solid is filtered, washed with hexanes, and dried under reduced pressure at 45° C. for 4 hours to give the title compound (52 g, 92%). Mass spectrum (m/z): 172.0 (M+1). $^1$H NMR (300 MHz, D$_2$O): 7.62 (d, J=8.0 Hz, 1H), 7.27 (d, J=8.0 Hz, 1H), 2.23 (s, 3H).

Preparation 7

Synthesis of methyl 4-[(6-chloro-3-methyl-pyridine-2-carbonyl)amino]-3,5-dimethyl-benzoate

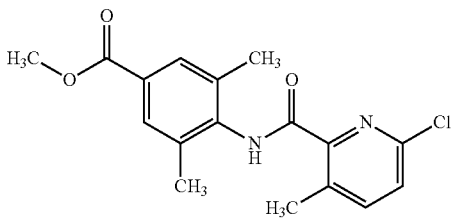 [SMILES: COC(=O)c1cc(C)c(NC(=O)c2nc(Cl)ccc2C)c(C)c1]

Scheme 2, step B. To a suspension of potassium 6-chloro-pyridine-2-carboxylate (52 g, 265.8 mmoles) in dimethylformamide (676 mL) is added bis(2-oxo-3-oxazolidinyl)phosphonic chloride (115 g, 451.8 mmoles). The mixture is stirred at ambient temperature for 30 minutes. Methyl 4-amino-3,5-dimethyl-benzoate (42.9 g, 239.2 mmoles, see preparation 12) and diisopropylethylamine (115.9 mL, 664.5 mmoles) are added. The reaction is stirred at ambient temperature for 16 hours. The mixture is then poured into water (2000 mL) and is stirred for 30 minutes. The resulting solid is filtered and dried under reduced pressure at 45° C. The dry material is triturated with hexane (1400 mL) over 2 hours. The solid is filtered and dried under vacuum to give the title compound (69 g, 78%) as a white solid. Mass spectrum (m/z): 333.05 (M+1). $^1$H NMR (300 MHz, DMSO): 10.16 (s, 1H), 7.89 (d, J=8.2 Hz, 1H), 7.73 (s, 2H), 7.63 (d, J=8.2 Hz, 1H), 3.85 (s, 3H), 2.49 (s, 3H), 2.28 (s, 6H).

Scheme 3

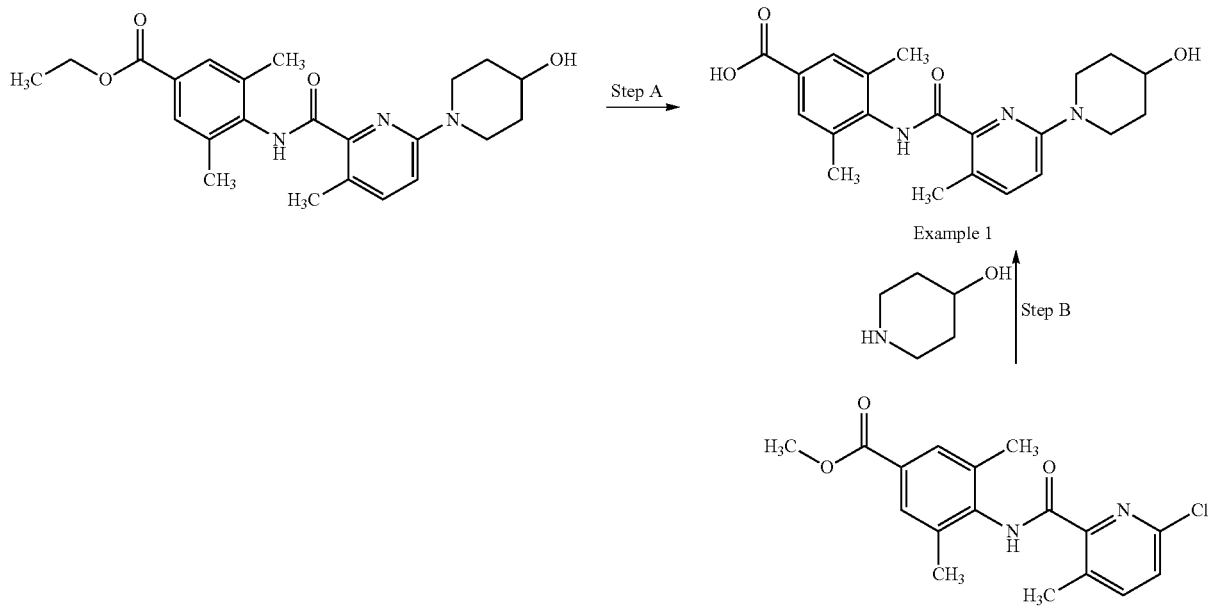

Example 1

EXAMPLE 1

Synthesis of 4-[[6-(4-hydroxy-1-piperidyl)-3-methyl-pyridine-2-carbonyl]amino]-3,5-dimethyl-benzoic acid

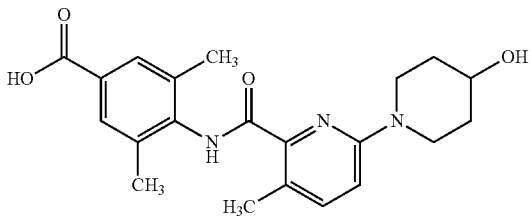 [SMILES: Cc1ccc(N2CCC(O)CC2)nc1C(=O)Nc1c(C)cc(C(=O)O)cc1C]

Scheme 3, step A. A solution of aqueous 1N NaOH (1.08 ml) is added to a stirred solution of ethyl 4-[[6-(4-hydroxy-1-piperidyl)-3-methyl-pyridine-2-carbonyl]amino]-3,5-dimethyl-benzoate (223 mg, 0.541 mmol) in THF:MeOH (4 ml:2 ml). After heating at 40° C. for 12 hours, the organic solvent is removed under reduced pressure and the semi-solid is dissolved in water and acidified to pH 3 with aqueous 1N HCl. The resulting precipitate is filtered, washed with water, and dried at 40° C. in a vacuum oven for 12 hours to give the title compound as a white solid (160 mg, 77%). Mass spectrum (m/z): 384.2 (M+1). Alternative synthesis of 4-[[6-(4-hydroxy-1-piperidyl)-3-methyl-pyridine-2-carbonyl]amino]-3,5-dimethyl-benzoic acid.

Scheme 3, step B. 4-Hydroxypiperidine (171.2 g, 1660 mmoles) is added to a solution of methyl 4-[(6-chloro-3-methyl-pyridine-2-carbonyl)amino]-3,5-dimethyl-benzoate (69 g, 207.3 mmoles) in N-methylpyrrolidone (483 mL) and the mixture is stirred at 150° C. for 4 hours. The mixture is cooled to ambient temperature and poured into water (1000 mL). The mixture is washed with methyl t-butyl ether (300 mL). The aqueous layer is then acidified to pH 2 with aqueous 36% HCl. The mixture is extracted with a solution of 1/1 ethyl acetate/methyl-t-butyl ether (3×250 mL). The organic layer is evaporated to dryness. Water (500 mL) is added to the residue and the resulting mixture is stirred for 30 minutes, filtered and the filtered material dried in an oven vacuum at 45° C. overnight. The dried light brown solid is dissolved in acetone (500 mL) and heated to 50° C. Water (1000 mL) is slowly added and the mixture is stirred at 50° C. for 2 hours. The mixture is cooled to ambient temperature, filtered, and the filtered material dried under reduced pressure at 45° C. The dried material is stirred in ethyl acetate (600 mL) at 50° C. for two hours. The mixture is cooled to ambient temperature, filtered, and the filtered material dried under reduced pressure at 45° C. overnight to give the title compound as a white solid (50.8 g, 64%). Mass spectrum (m/z): 384.2 (M+1). $^1$H NMR (300 MHz, DMSO): 12.85 (s, 1H), 9.87 (s, 1H), 7.71 (s, 2H), 7.49 (d, J=8.7 Hz, 1H), 7.01 (d, J=8.7 Hz, 1H), 4.68 (d, J=4.1 Hz, 1H), 4.11-4.04 (m, 2H), 3.70 (m, 1H), 3.15-3.07 (m, 2H), 2.41 (s, 3H), 2.27 (s, 6H), 1.81-1.77 (m, 2H), 1.44-1.32 (m, 2H).

X-Ray Powder Diffraction

The XRD patterns of crystalline solids are obtained on a Bruker D4 Endeavor X-ray powder diffractometer, equipped with a CuKa source ($\lambda$=1.54060 Å) and a Vantec detector, operating at 35 kV and 50 mA. The sample is scanned between 4 and 40° in 2θ, with a step size of 0.0087° in 2θ and a scan rate of 0.5 seconds/step, and with 0.6 mm divergence, 5.28 mm fixed anti-scatter, and 9.5 mm detector slits. The dry powder is packed on a quartz sample holder and a smooth surface is obtained using a glass slide. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The U.S. Pharmacopeia 35-National Formulary 30 Chapter <941> Characterization of crystalline and partially crystalline solids by X-ray powder diffraction (XRPD) Official Dec. 1, 2012-May 1, 2013. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of °2θ), typically the more prominent peaks. The crystal form diffraction patterns, collected at ambient temperature and relative humidity, were adjusted based on NIST 675 standard peaks at 8.85 and 26.77 degrees 2-theta.

EXAMPLE A

Preparation of hydrated 4-[[6-(4-hydroxy-1-piperidyl)-3-methyl-pyridine-2-carbonyl]amino]-3,5-dimethyl-benzoic acid 4-[[6-(4-Hydroxy-1-piperidyl)-3-methyl-pyridine-2-carbonyl]amino]-3,5-dimethyl-benzoic acid (240.7 mg) is dissolved in 10 ml of 1:1 acetone:water to give a clear pale solution. The mixture is concentrated at room temperature and crystalline hydrated form begins to slowly precipitate from solution over several minutes. The resulting solids are filtered and air dried to give 197.5 mg of the title compound.

A prepared sample of the title compound of Example A is characterized by an X-ray powder diffraction pattern using CuKα radiation as having diffraction peaks (2-theta values) as described in Table 1 below. Specifically the pattern contains a peak at 9.0° in combination with two or more of the peaks selected from the group consisting of 5.8°, 8.5°, 9.8°, 11.6°, 11.8°, 17.5°, and 24.2° with a tolerance for the diffraction angles of 0.2 degrees.

TABLE 1

X-ray powder diffraction peaks of Example A.

| Peak | Angle (2-Theta °) | Intensity (%) |
|---|---|---|
| 1 | 5.8 | 43 |
| 2 | 8.5 | 16 |
| 3 | 9.0 | 100 |
| 4 | 9.8 | 21 |
| 5 | 11.6 | 62 |
| 6 | 11.8 | 34 |
| 7 | 14.1 | 9 |
| 8 | 15.3 | 15 |
| 9 | 15.4 | 30 |
| 10 | 17.5 | 43 |
| 11 | 20.4 | 11 |
| 12 | 20.8 | 21 |
| 13 | 22.7 | 13 |
| 14 | 24.2 | 35 |
| 15 | 24.6 | 19 |
| 16 | 27.5 | 9 |

Scheme 4

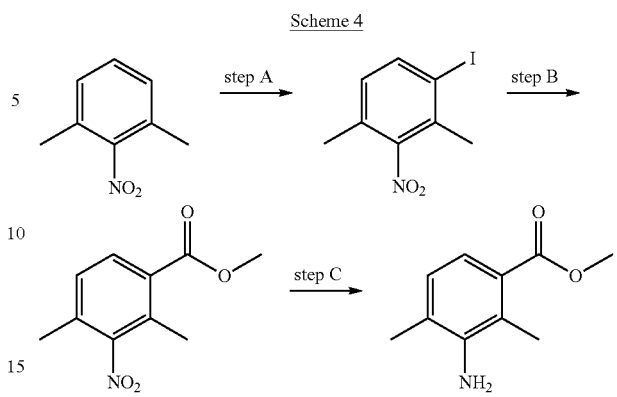

Preparation 8

Synthesis of 1-iodo-2,4-dimethyl-3-nitro-benzene

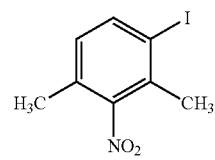

Scheme 4, step A: To 1,3-dimethyl-2-nitro-benzene (68.5 g, 453.2 mmol) is added sulfuric acid (27.2 mL, 510 mmol), acetic acid (543.8 mL, 9.49 mol), iodine (46 g, 181.3 mmol) and HIO$_4$ (91.9 g, 403.3 mmol). The reaction is heated to 90° C. for 7 days. The reaction mixture is cooled to ambient temperature and water (500 mL) is added. The resulting solid is collected by filtration and washed with cold water. The solid is dried under reduced pressure at 45° C. overnight to afford the title compound as a yellow solid (119 g, 95%). $^1$H NMR (300.16 MHz, CDCl$_3$): δ 7.80 (d, J=8.2 Hz, 1H), 6.85 (d, J=8.2 Hz, 1H), 2.37 (s, 3H), 2.23 (s, 3H).

Preparation 9

Synthesis of methyl 2,4-dimethyl-3-nitro-benzoate

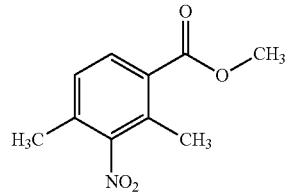

Scheme 4, Step B: To a 2 L Parr™ autoclave with mechanical stirring is added 1-iodo-2,4-dimethyl-3-nitro-benzene (70 g, 252.7 mmol), Pd(OAc)$_2$ (2.8 g, 12.6 mmol), 1,4-bis(diphenylphosphino)butane (6.5 g, 15.2 mmol), acetonitrile (462 mL), triethylamine (88.2 mL), and methanol (280 mL). The Parr™ autoclave is sealed, purged and pressurized with CO to 551.6 kPa (80 psig). The mixture is heated to 100° C. for 2 hours. The mixture is cooled to ambient temperature and then vented. The mixture is then concentrated to dryness under reduced pressure. Ethyl acetate (300 mL) and water (300 mL) are added. The layers are separated and the aqueous layer discarded. The organic layer is dried over MgSO$_4$, filtered, and concentrated to dryness to afford the title compound as a red oil which crystallizes upon standing (52 g, 98%). $^1$H NMR (300.13 MHz, CDCl$_3$): δ 7.89 (d, J=8.2 Hz, 1H), 7.19 (d, J=8.2 Hz, 1H), 3.91 (s, 3H), 2.49 (s, 3H), 2.33 (s, 3H).

Preparation 10

Synthesis of methyl 3-amino-2,4-dimethyl-benzoate

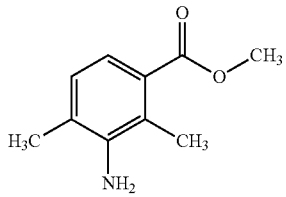

Scheme 4, Step C: To a solution of methyl 2,4-dimethyl-3-nitro-benzoate (37 g, 176.9 mmol) in methanol (370 mL), 10% palladium on carbon 50% wet (5.6 g) is added. The reaction is bubbled with hydrogen and placed under a hydrogen atmosphere for 6 days. The mixture is filtered through diatomaceous earth and the filtrate is evaporated to dryness. The resulting residue is purified by flash chromatography (silica gel), eluting with 20% ethyl acetate in hexanes to afford the title compound as a yellow oil (20.5 g, 65%). Mass spectrum (m/z): 180.1 (M+1). $^1$H NMR (300.16 MHz, DMSO-d$_6$): δ 6.89 (s, 2H), 4.78 (s, 2H), 3.76 (s, 3H), 2.23 (s, 3H), 2.12 (s, 3H).

Scheme 5

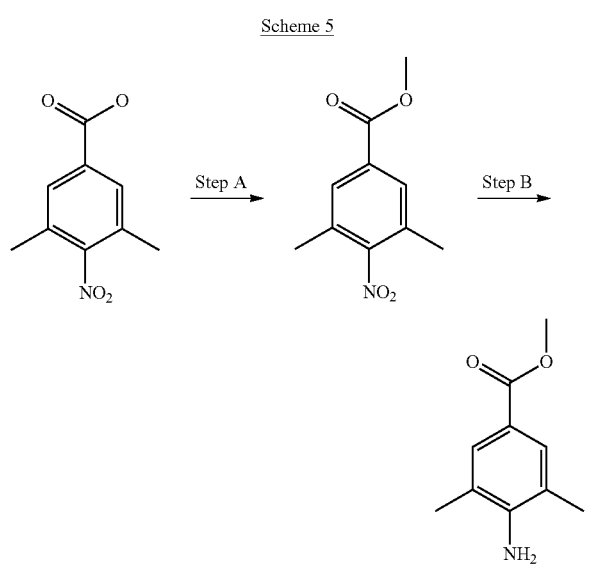

Preparation 11

Synthesis of methyl 3,5-dimethyl-4-nitro-benzoate

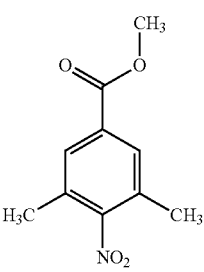

Scheme 5, step A. To a solution of 3,5-dimethyl-4-nitro-benzoic acid (10.0 g, 0.0512 mol) in MeOH (150 mL) is added thionyl chloride (10 ml) at 0° C. and the reaction is heated to 80° C. After 16 h, the reaction mixture is cooled to room temperature and solvent is removed under reduced pressure. The residue is diluted with water (50 ml) and basified with saturated NaHCO$_3$ solution to pH 7-8 and extracted with EtOAc (2×120 mL). The organic layers are combined and dried over anhydrous sodium sulfate. The solvent is removed under reduced pressure to afford the title compound as a light yellow solid (10.71 g, 98.3%). $^1$H NMR (400 MHz, DMSO): δ 7.83 (s, 2H), 3.88 (s, 3H), 2.30 (s, 6H).

Preparation 12

Synthesis of methyl 4-amino-3,5-dimethyl-benzoate

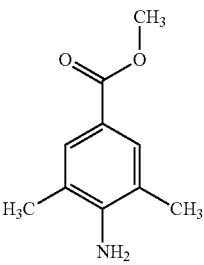

Scheme 5, step B. To a solution of methyl 3,5-dimethyl-4-nitrobenzoate (10.0 g, 0.0478 mol) in methanol (100 mL), iron powder (15.7 g, 0.2869 mol) and 37% HCl (1.72 g, 0.0478 mol) is added at 0° C. The reaction is heated at 80° C. for 16 hours. The mixture is cooled to room temperature and filtered through Celite™ bed and washed with methanol followed by evaporation of filtrate to dryness to afford the title compound as a brown solid (7.8 g, 99%). Mass spectrum (m/z): 180.2 (M+1).

Scheme 6

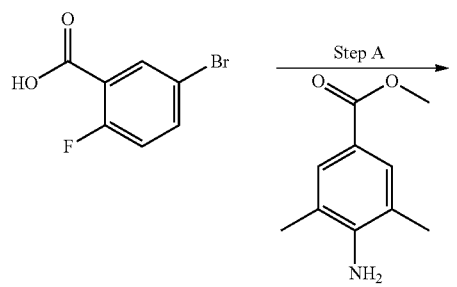

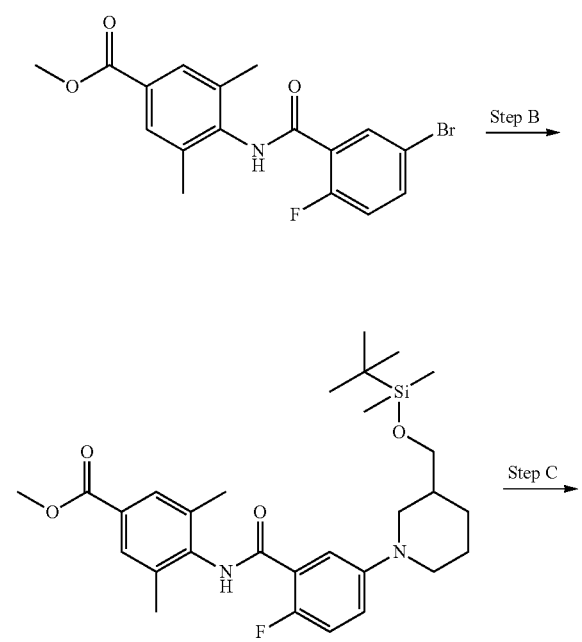

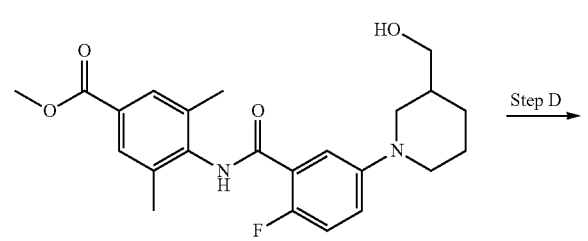

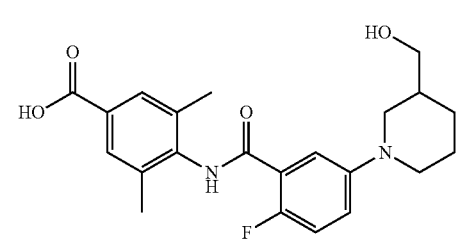

Preparation 13

Synthesis of methyl 4-[(5-bromo-2-fluoro-benzoyl)amino]-3,5-dimethyl-benzoate

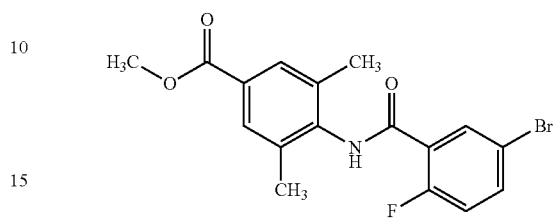

Scheme 6, step A. To a solution of 5-bromo-2-fluorobenzoic acid (3.50 g, 15.9 mmol) in $CH_2Cl_2$ (50 mL) at 0° C. are added methyl 4-amino-3,5-dimethylbenzoate (2.86 g, 15.9 mmol, see preparation 12) and N,N-diisopropylethylamine (8.35 ml, 47.9 mmol). After stirring the reaction mixture for 10 minutes, 1-propanephosphonic acid cyclic anhydride (50% solution in ethyl acetate, 20.5 ml, 31.9 mmol) is added via syringe and stirred at ambient temperature. After 36 hours, the solvent is removed under reduced pressure and the residue is diluted with water and extracted with ethyl acetate. The organic layers are combined and dried over anhydrous $Na_2SO_4$, filtered, and concentrated under reduced pressure. The resulting residue is purified by flash chromatography (silica gel) using 10% ethyl acetate in hexane to give the title compound as a white solid (4.20 g, 69%). Mass spectrum (m/z): 380.2 (M+1).

Preparation 14

Synthesis of tert-butyl-dimethyl-(3-piperidylmethoxy)silane

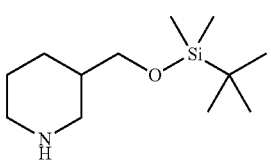

Scheme 6, step B. To a solution of piperidin-3-ylmethanol (2.10 g, 0.018 mol) in $CH_2Cl_2$ (20 mL) is added triethylamine (5.53 g, 0.0547 mol) followed by t-butyldimethylchlorosilane (4.127 g, 0.0275 mol) and the reaction mixture is stirred at room temperature. After 24 hours, the reaction mixture is washed with water, saturated solution of $NaHCO_3$, and brine. The combined organic layers are combined and dried over sodium sulfate, filtered, and concentrated under reduced pressure. The resulting residue is purified by flash chromatography (silica gel) over a gradient using 0-10% MeOH in dichloromethane to afford the title compound (2.50 g, 60%). Mass spectrum (m/z): 231.2 (M+1).

Preparation 15

Synthesis of methyl 4-[[5-[3-[[tert-butyl(dimethyl)silyl]oxymethyl]-1-piperidyl]-2-fluoro-benzoyl]amino]-3,5-dimethyl-benzoate

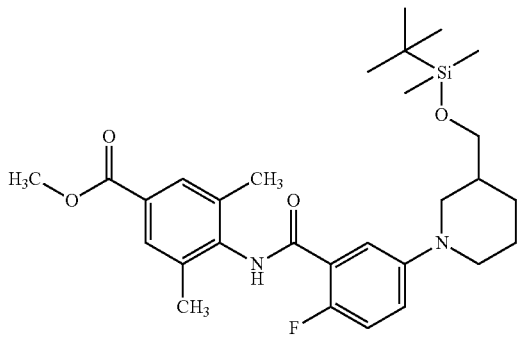 [SMILES: COC(=O)c1cc(C)c(NC(=O)c2cc(N3CCCC(CO[Si](C)(C)C(C)(C)C)C3)ccc2F)c(C)c1]

Scheme 6, step B. To a solution of methyl 4-[(5-bromo-2-fluoro-benzoyl)amino]-3,5-dimethyl-benzoate (0.40 g, 1.05 mmol), tert-butyl-dimethyl-(3-piperidylmethoxy)silane (0.362 g, 1.57 mmol) and $Cs_2CO_3$ (1.04 g, 3.15 mmol) in 1,4-dioxane (6 ml) is added $Pd_2(dba)_3$ (0.10 g, 0.105 mmol) followed by S-Phos (0.043 g, 0.105 mmol). The reaction mixture is purged with nitrogen for 5 minutes and then heated at 90° C. After 16 hours, the reaction is cooled to ambient temperature, filtered through Celite™, and washed with EtOAc. The combined filtrates are dried over sodium sulfate, filtered, and concentrated under reduced pressure and purified by flash chromatography (silica gel) using 10% EtOAc in hexane to afford the title compound as a pale yellow oil (0.22 g, 40%). Mass spectrum (m/z): 529.2 (M+1).

Preparation 16

Synthesis of methyl 4-[[2-fluoro-5-[3-(hydroxymethyl)-1-piperidyl]benzoyl]amino]-3,5-dimethyl-benzoate

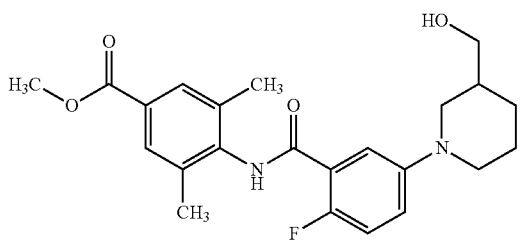 [SMILES: COC(=O)c1cc(C)c(NC(=O)c2cc(N3CCCC(CO)C3)ccc2F)c(C)c1]

Scheme 6, step C. To a solution of methyl 4-[[5-[3-[[tert-butyl(dimethyl)silyl]oxymethyl]-1-piperidyl]-2-fluoro-benzoyl]amino]-3,5-dimethyl-benzoate (0.30 g, 0.54 mmol) in THF (8 ml) is added $Bu_4NF$ 1.0 M in THF (0.35 g, 1.60 mmol) at 0° C. The reaction mixture is gradually warmed to ambient temperature. After 4 hours, the reaction mixture is diluted with ice-water and extracted with ethyl acetate. The organic layers are combined, dried over sodium sulfate, filtered, and concentrated under reduced pressure to give a residue. The residue is purified by flash chromatography (silica gel) over a gradient using ethyl acetate in hexanes as eluent to afford the title compound as a white solid (0.10 g, 55%). Mass spectrum (m/z): 414.2 (M+1).

EXAMPLE 2

Synthesis of 4-[[2-fluoro-5-[3-(hydroxymethyl)-1-piperidyl]benzoyl]amino]-3,5-dimethyl-benzoic acid

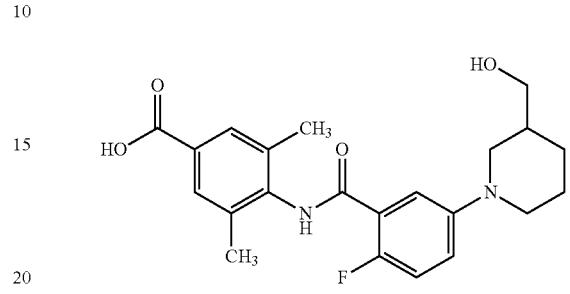

Scheme 6, step D. A solution of aqueous 2N NaOH (2.00 ml) is added to a stirred solution of methyl 4-[[2-fluoro-5-[3-(hydroxymethyl)-1-piperidyl]benzoyl]amino]-3,5-dimethyl-benzoate (0.18 g, 0.43 mmol) in THF:MeOH (3 ml:1 ml). After 16 h at 50° C., the organic solvent is removed under reduced pressure and the residue is diluted with water, acidified to pH 4 with 1N HCl and extracted with $CH_2Cl_2$. The organic layers are combined and dried over anhydrous sodium sulfate. The solvent is removed under reduced pressure and the resulting precipitate is triturated with diethyl ether and filtered to afford the title compound as a white solid (0.12 g, 69%). Mass spectrum (m/z): 401.2 (M+1).

Chiral separation of racemic 4-[[2-fluoro-5-[3-(hydroxymethyl)-1-piperidyl]benzoyl]amino]-3,5-dimethyl-benzoic acid.

4-[[2-fluoro-5-[3-(hydroxymethyl)-1-piperidyl]benzoyl]amino]-3,5-dimethyl-benzoic acid is separated by chiral chromatography using Chiralpak™ AD-H, 25% MeOH/CO2, 5 ml/min, 225 nm to give:

EXAMPLE 2A

4-[[2-fluoro-5-[3-(hydroxymethyl)-1-piperidyl]benzoyl]amino]-3,5-dimethyl-benzoic acid isomer 1. Peak eluting at 2.52 min. Mass spectrum (m/z): 401.2 (M+1).

EXAMPLE 2B

4-[[2-fluoro-5-[3-(hydroxymethyl)-1-piperidyl]benzoyl]amino]-3,5-dimethyl-benzoic acid isomer 2. Peak eluting at 2.93 min. Mass spectrum (m/z): 401.2 (M+1).

Scheme 7

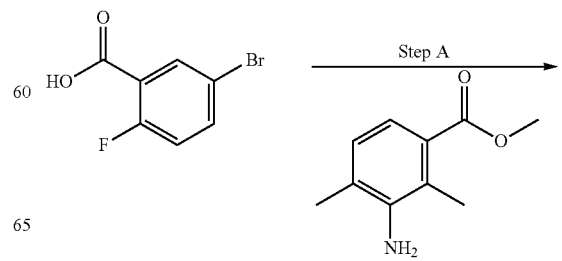

-continued

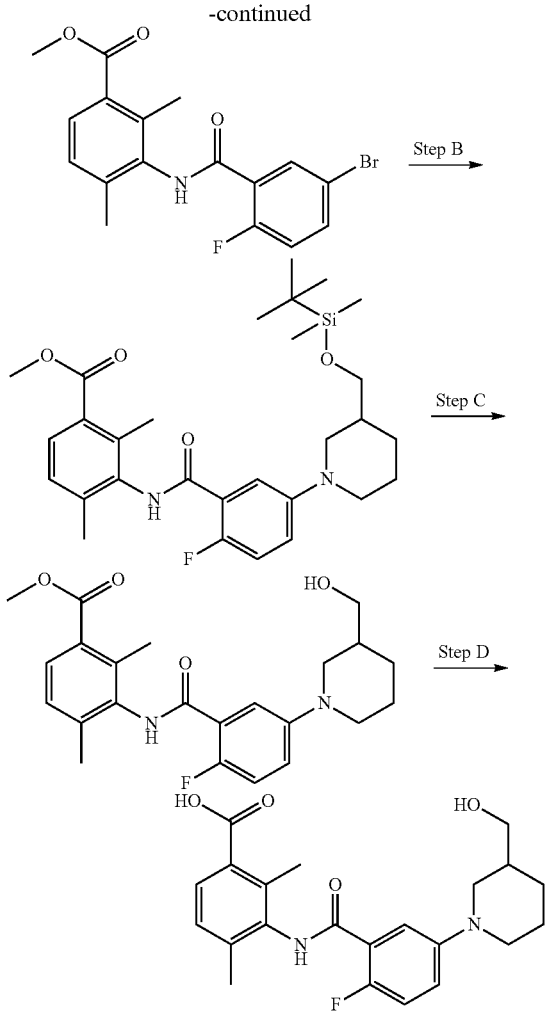

Preparation 17

Synthesis of methyl 3-[(5-bromo-2-fluoro-benzoyl)amino]-2,4-dimethyl-benzoate

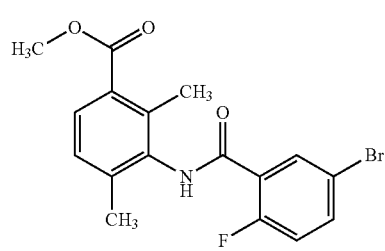 [SMILES: COC(=O)c1ccc(C)c(NC(=O)c2cc(Br)ccc2F)c1C]

Scheme 7, step A. To a solution of 5-bromo-2-fluoro-benzoic acid (500 mg, 2.28 mmol) in CH$_2$Cl$_2$ (15 mL) at 0° C. are added methyl 3-amino-2,4-dimethylbenzoate (409 mg, 2.28 mmol, see preparation 10) and N,N-diisopropylethylamine (737.6 mg, 5.71 mmol). After stirring the reaction mixture for 10 minutes, 1-propanephosphonic acid cyclic anhydride (50% solution in ethyl acetate, 1.74 g, 2.74 mmol) is added via syringe and stirred at 50° C. After 16 hours, the solvent is removed under reduced pressure and the residue is triturated with MeOH to give the title compound as a white solid (450 mg, 51.8%). Mass spectrum (m/z): 380.2 (M+1).

Preparation 18

Synthesis of methyl 3-[[5-[3-[[tert-butyl(dimethyl)silyl]oxymethyl]-1-piperidyl]-2-fluoro-benzoyl]amino]-2,4-dimethyl-benzoate

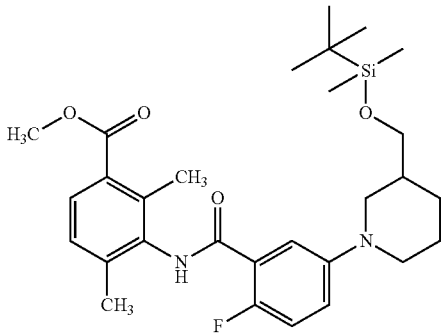 [SMILES: COC(=O)c1ccc(C)c(NC(=O)c2cc(N3CCCC(CO[Si](C)(C)C(C)(C)C)C3)ccc2F)c1C]

Scheme 7, step B. To a solution of methyl 3-[(5-bromo-2-fluoro-benzoyl)amino]-2,4-dimethyl-benzoate (0.7 g, 1.84 mmol), tert-butyl-dimethyl-(3-piperidylmethoxy)silane (2.53 g, 11.03 mmol, see preparation 14) and Cs$_2$CO$_3$ (1.81 g, 5.50 mmol) in 1,4-dioxane (15 ml) is added Pd$_2$(dba)$_3$ (0.168 g, 0.184 mol) followed by S-Phos (0.075 g, 0.184 mol). The reaction mixture is purged with nitrogen for 5 minutes and then heated at 120° C. After 6 hours, the reaction mixture is concentrated under reduced pressure and residue is carried forward without further purification.

Preparation 19

Synthesis of methyl 3-[[2-fluoro-5-[3-(hydroxymethyl)-1-piperidyl]benzoyl]amino]-2,4-dimethyl-benzoate

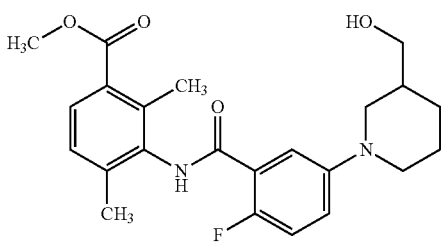 [SMILES: COC(=O)c1ccc(C)c(NC(=O)c2cc(N3CCCC(CO)C3)ccc2F)c1C]

Scheme 7, step C. To a solution of methyl 3-[[5-[3-[[tert-butyl(dimethyl)silyl]oxymethyl]-1-piperidyl]-2-fluoro-benzoyl]amino]-2,4-dimethyl-benzoate (2.9 g, 5.48 mmol) in THF (20 ml) is added Bu$_4$NF 1.0 M in THF (5.73 g, 0.0219 mol) at 0° C. The reaction mixture is gradually warmed to ambient temperature. After 4 hours, the reaction mixture is diluted with ice-water and extracted with ethyl acetate. The organic layers are combined, dried over sodium sulfate, filtered, and concentrated under reduced pressure to give a residue. The residue is purified by flash chromatography (silica gel) over a gradient using 35-45% ethyl acetate in hexane to afford the title compound as a white solid (0.38 g, 16.8%). Mass spectrum (m/z): 415.2 (M+1).

EXAMPLE 3

Synthesis of 3-[[2-fluoro-5-[3-(hydroxymethyl)-1-piperidyl]benzoyl]amino]-2,4-dimethyl-benzoic acid

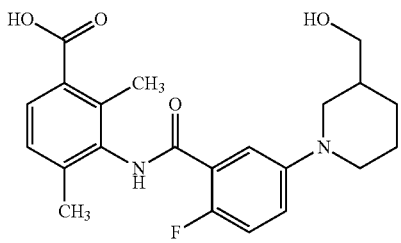

Scheme 7, step D. A solution of NaOH (0.146 mg, 0.00366 mol) in 1.5 ml of H$_2$O is added to a stirred solution of methyl 3-[[2-fluoro-5-[3-(hydroxymethyl)-1-piperidyl]benzoyl]amino]-2,4-dimethyl-benzoate (0.38 g, 0.000916 mol) in THF:EtOH (3 ml:2 ml). After 4 hours at ambient temperature, the organic solvent is removed under reduced pressure and the residue is diluted with water, acidified to pH 4 with 1N HCl, and extracted with ethyl acetate. The organic layer are combined and dried over anhydrous sodium sulfate. The solvent is removed under reduced pressure to afford the title compound as a light yellow solid (85 mg g, 36.8%). Mass spectrum (m/z): 401.2 (M+1).

Scheme 8

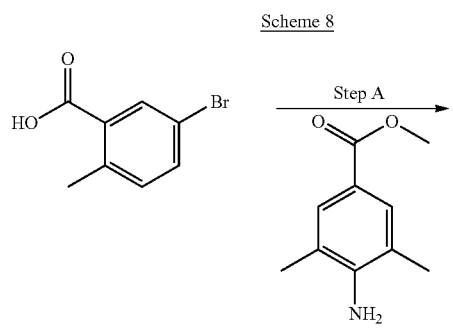

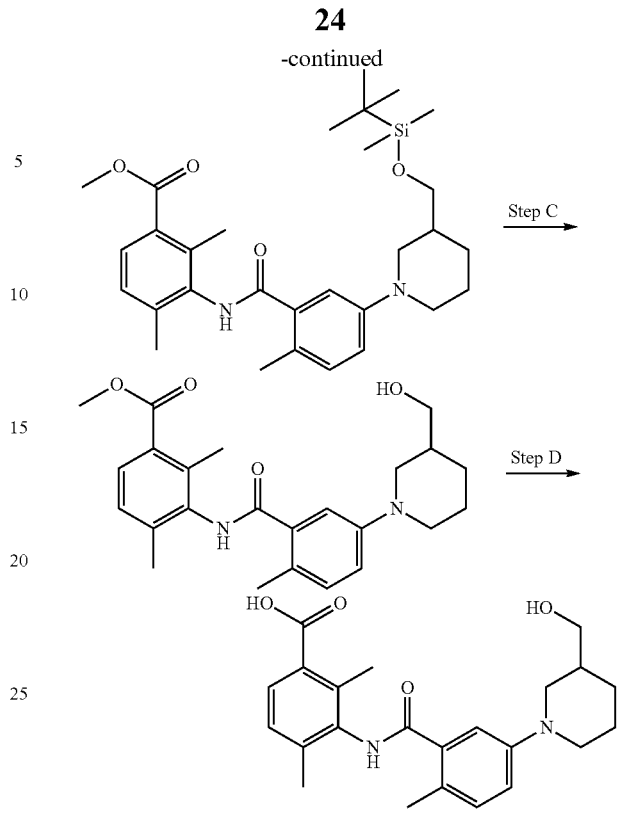

Preparation 20

Synthesis of methyl 3-[(5-bromo-2-methyl-benzoyl)amino]-2,4-dimethyl-benzoate

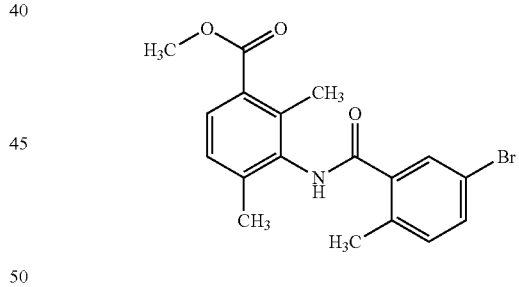

Scheme 8, step A. To a solution of 5-bromo-2-methylbenzoic acid (2.0 g, 0.0093 mol) in CH$_2$Cl$_2$ (20 mL) at 0° C. are added methyl 3-amino-2,4-dimethylbenzoate (1.49 g, 0.0084 mol, see preparation 10) and N,N-diisopropylethylamine (4.79 g, 0.0372 mol). After stirring the reaction mixture for 10 minutes, 1-propanephosphonic acid cyclic anhydride (50% solution in ethyl acetate, 8.87 g, 0.028 mol) is added via syringe and stirred at 50° C. After 16 hours, the solvent is removed under reduced pressure and the residue is diluted with water and extracted twice with ethyl acetate. The organic layers are combined and dried over anhydrous Na$_2$SO$_4$, filtered, and concentrated under reduced pressure. The resulting residue is purified by flash chromatography (silica gel) using 10% ethyl acetate in hexane to give the title compound as a white solid (2.80 g, 80%). Mass spectrum (m/z): 376.1 (M+1).

Preparation 21

Synthesis of methyl 3-[[5-[3-[[tert-butyl(dimethyl)silyl]oxymethyl]-1-piperidyl]-2-methyl-benzoyl]amino]-2,4-dimethyl-benzoate

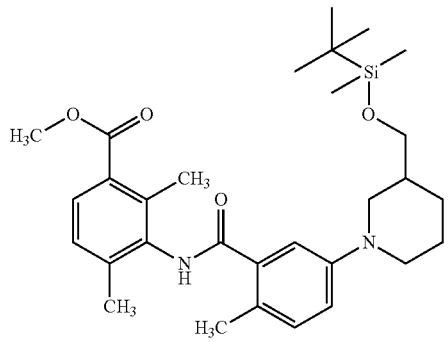 [SMILES: COC(=O)c1ccc(C)c(NC(=O)c2cc(N3CCCC(CO[Si](C)(C)C(C)(C)C)C3)ccc2C)c1C]

Scheme 8, step B. To a solution of methyl 3-[(5-bromo-2-methyl-benzoyl)amino]-2,4-dimethyl-benzoate (0.5 g, 1.32 mmol), tert-butyl-dimethyl-(3-piperidylmethoxy)silane (0.45 g, 1.99 mmol, see preparation 14) and Cs$_2$CO$_3$ (1.29 g, 3.98 mmol) in 1,4-dioxane (15 ml) is added Pd$_2$(dba)$_3$ (0.12 g, 0.132 mmol) followed by S-Phos (0.050 g, 0.132 mmol). The reaction mixture is purged with nitrogen for 5 minutes and then heated at 110° C. After 6 hours, the reaction is cooled to ambient temperature, filtered through Celite™, and washed with EtOAc. The combined filtrates are dried over sodium sulfate, filtered, and concentrated under reduced pressure and purified by flash chromatography (silica gel) using 15% EtOAc in hexane as eluent to afford the title compound as a brown semi solid (0.6 g, 85%). Mass spectrum (m/z): 525.2 (M+1).

Preparation 22

Synthesis of methyl 3-[[5-[3-(hydroxymethyl)-1-piperidyl]-2-methyl-benzoyl]amino]-2,4-dimethyl-benzoate

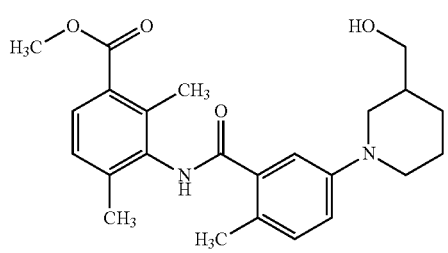 [SMILES: COC(=O)c1ccc(C)c(NC(=O)c2cc(N3CCCC(CO)C3)ccc2C)c1C]

Scheme 8, step C. To a solution of methyl 3-[[5-[3-[[tert-butyl(dimethyl)silyl]oxymethyl]-1-piperidyl]-2-methyl-benzoyl]amino]-2,4-dimethyl-benzoate (0.60 g, 1.14 mmol) in THF (15 ml) is added Bu$_4$NF 1.0 M in THF (0.596 g, 2.28 mmol) at 0° C. The reaction mixture is gradually warmed to ambient temperature. After 1 hour, the reaction mixture is diluted with ice-water and extracted with ethyl acetate. The organic layers are combined, dried over sodium sulfate, filtered, and concentrated under reduced pressure to give a residue. The residue is purified by flash chromatography (silica gel) over a gradient using 4% methanol in dichloromethane as eluent to afford the title compound as a white solid (0.4 g, 85.5%). Mass spectrum (m/z): 411.4 (M+1).

EXAMPLE 4

Synthesis of 3-[[5-[3-(hydroxymethyl)-1-piperidyl]-2-methyl-benzoyl]amino]-2,4-dimethyl-benzoic acid

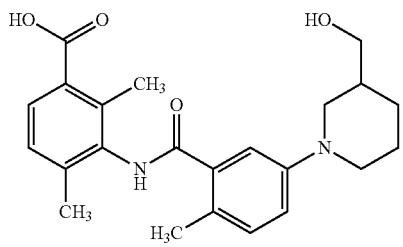

Scheme 8, step D. A solution of aqueous 4N NaOH (4.00 ml) is added to a stirred solution of methyl 3-[[5-[3-(hydroxymethyl)-1-piperidyl]-2-methyl-benzoyl]amino]-2,4-dimethyl-benzoate (0.4 g, 0.975 mmol) in THF:MeOH (10 ml:5 ml). After 4 hours at ambient temperature, the organic solvent is removed under reduced pressure and the residue is diluted with water, acidified to pH 4 with 1N HCl, and extracted twice with 10% IPA in CH$_2$Cl$_2$. The organic layers are combined and dried over anhydrous sodium sulfate. The solvent is removed under reduced pressure and the resulting precipitate is triturated with diethyl ether and filtered to afford the title compound as a light brown solid (0.28 g, 72.5%). Mass spectrum (m/z): 397.2 (M+1).

Chiral separation of racemic 3-[[5-[3-(hydroxymethyl)-1-piperidyl]-2-methyl-benzoyl]amino]-2,4-dimethyl-benzoic acid.

3-[[5-[3-(hydroxymethyl)-1-piperidyl]-2-methyl-benzoyl]amino]-2,4-dimethyl-benzoic acid is separated by chiral chromatography using Chiralcel™ OJ-H, 15% MeOH/CO2, 5 ml/min, 225 nm to give:

EXAMPLE 4A

3-[[5-[3-(hydroxymethyl)-1-piperidyl]-2-methyl-benzoyl]amino]-2,4-dimethyl-benzoic acid isomer 1. Peak eluting at 1.76 min. Mass spectrum (m/z): 397.2 (M+1).

EXAMPLE 4B

3-[[5-[3-(hydroxymethyl)-1-piperidyl]-2-methyl-benzoyl]amino]-2,4-dimethyl-benzoic acid isomer 2. Peak eluting at 2.49 min. Mass spectrum (m/z): 397.2 (M+1).

Scheme 9

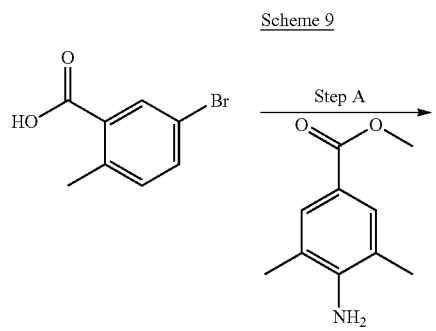

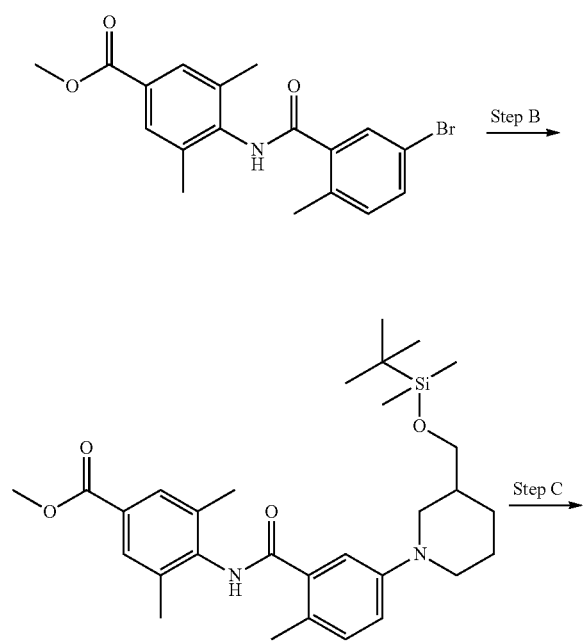

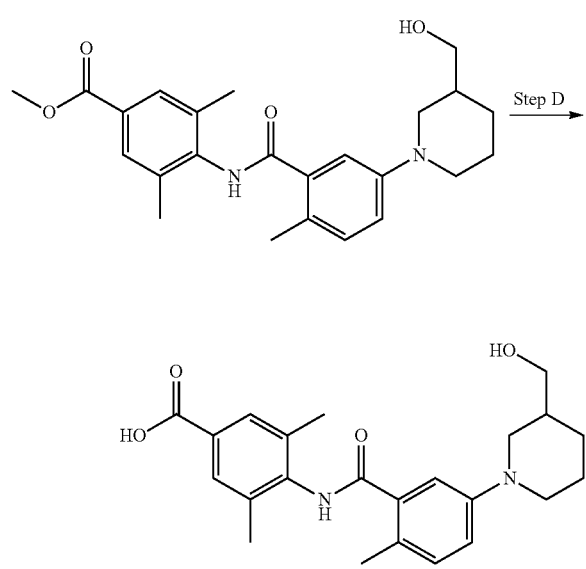

Preparation 23

Synthesis of methyl 4-[(5-bromo-2-methyl-benzoyl)amino]-3,5-dimethyl-benzoate

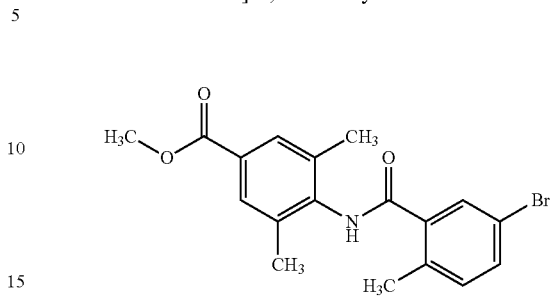

Scheme 9, step A. To a solution of 5-bromo-2-methylbenzoic acid (2.0 g, 0.008 mol) in $CH_2Cl_2$ (20 mL) at 0° C. are added methyl 4-amino-3,5-dimethylbenzoate (1.28 g, 0.0072, see preparation 12) and N,N-diisopropylethylamine (4.12 g, 0.032 mol). After stirring the reaction mixture for 10 minutes, 1-propanephosphonic acid cyclic anhydride (50% solution in ethyl acetate, 7.63 g, 0.024 mol) is added via syringe and stirred at 50° C. After 16 hours, the solvent is removed under reduced pressure and the residue is diluted with water and extracted twice with ethyl acetate. The organic layers are combined and dried over anhydrous $Na_2SO_4$, filtered, and concentrated under reduced pressure. The resulting residue is purified by flash chromatography (silica gel) using 12% ethyl acetate in hexane to give the title compound as a white solid (2.9 g, 97%). Mass spectrum (m/z): 376.0 (M+1).

Preparation 24

Synthesis of methyl 4-[[5-[3-[[tert-butyl(dimethyl)silyl]oxymethyl]-1-piperidyl]-2-methyl-benzoyl]amino]-3,5-dimethyl-benzoate

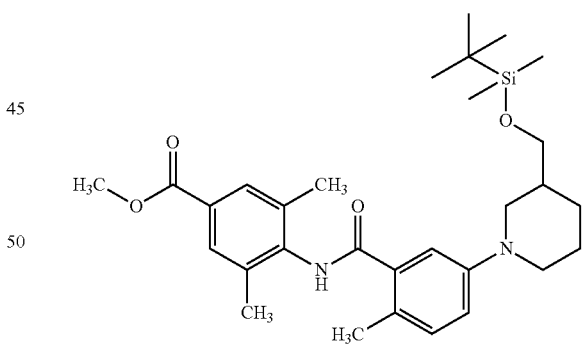

Scheme 9, step B. To a solution of methyl 4-(5-bromo-2-methylbenzamido)-3,5-dimethylbenzoate (0.5 g, 0.0013 mol), tert-butyl-dimethyl-(3-piperidylmethoxy)silane (0.45 g, 0.0019 mol, preparation 14) and $Cs_2CO_3$ (1.29 g, 0.0039 mol) in 1,4-dioxane (15 ml) is added $Pd_2(dba)_3$ (0.12 g, 0.00013 mol) followed by S-Phos (0.054 g, 0.00013 mol). The reaction mixture is purged with nitrogen for 5 minutes and then heated at 110° C. After 16 hours, the reaction is cooled to ambient temperature, filtered through Celite™ and washed with EtOAc. The combined filtrates are dried over sodium sulfate, filtered, and concentrated under reduced pressure and purified by flash chromatography (silica gel) using 15% ethyl acetate in hexane as eluent to afford the title compound as a brown semi solid (0.4 g, 57.3%). Mass spectrum (m/z): 525.2 (M+1).

Preparation 25

Synthesis of methyl 4-[[5-[3-(hydroxymethyl)-1-piperidyl]-2-methyl-benzoyl]amino]-3,5-dimethyl-benzoate

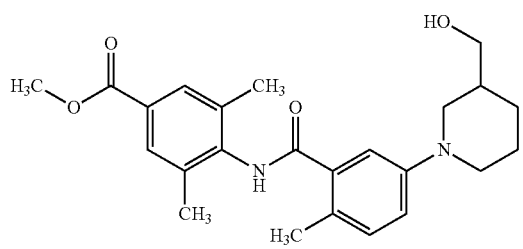

Scheme 9, step C. To a solution of methyl 4-[[5-[3-[[tert-butyl(dimethyl)silyl]oxymethyl]-1-piperidyl]-2-methyl-benzoyl]amino]-3,5-dimethyl-benzoate (0.40 g, 0.76 mmol) in THF (10 ml) is added Bu$_4$NF 1.0 M in THF (0.39 g, 1.52 mmol) at 0° C. The reaction mixture is gradually warmed to ambient temperature. After 1 hour, the reaction mixture is diluted with ice-water and extracted with ethyl acetate. The organic layers are combined, dried over sodium sulfate, filtered, and concentrated under reduced pressure to give a residue. The residue is purified by flash chromatography (silica gel) over a gradient using 4% MeOH in dichloromethane to afford the title compound as a light brown solid (0.30 g, 96%). Mass spectrum (m/z): 411.5 (M+1).

EXAMPLE 5

Synthesis of 4-[[5-[3-(hydroxymethyl)-1-piperidyl]-2-methyl-benzoyl]amino]-3,5-dimethyl-benzoic acid

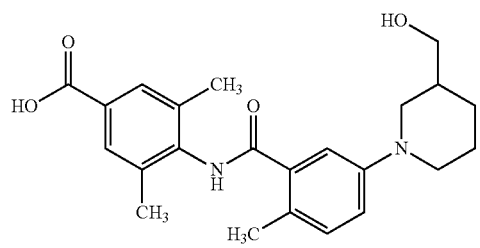 [SMILES: Cc1ccc(N2CCCC(CO)C2)cc1C(=O)Nc1c(C)cc(C(=O)O)cc1C]

Scheme 9, step D. A solution of aqueous 4N NaOH (2.00 ml) is added to a stirred solution of methyl 4-[[5-[3-(hydroxymethyl)-1-piperidyl]-2-methyl-benzoyl]amino]-3,5-dimethyl-benzoate (0.3 g, 0.73 mmol) in THF:MeOH (10 ml:5 ml). After 16 hours at ambient temperature, the organic solvent is removed under reduced pressure and the residue is diluted with water, acidified to pH 4 with 1N HCl, and extracted with 10% IPA in CH$_2$Cl$_2$. The organic layers are combined and dried over anhydrous sodium sulfate. The solvent is removed under reduced pressure and the resulting precipitate is triturated with diethyl ether and filtered to afford the title compound as a light brown solid (0.27 g, 90%). Mass spectrum (m/z): 397.2 (M+1).

Chiral separation of racemic 4-[[5-[3-(hydroxymethyl)-1-piperidyl]-2-methyl-benzoyl]amino]-3,5-dimethyl-benzoic acid.

4-[[5-[3-(hydroxymethyl)-1-piperidyl]-2-methyl-benzoyl]amino]-3,5-dimethyl-benzoic acid is separated by chiral chromatography using Chiralpak AD-H, 30% EtOH/CO$_2$, 5 ml/min, 225 nm to give:

EXAMPLE 5A

4-[[5-[3-(hydroxymethyl)-1-piperidyl]-2-methyl-benzoyl]amino]-3,5-dimethyl-benzoic acid isomer 1. Peak eluting at 4.22 min. Mass spectrum (m/z): 397.2 (M+1).

EXAMPLE 5B

4-[[5-[3-(hydroxymethyl)-1-piperidyl]-2-methyl-benzoyl]amino]-3,5-dimethyl-benzoic acid isomer 2. Peak eluting at 5.30 min. Mass spectrum (m/z): 397.2 (M+1).

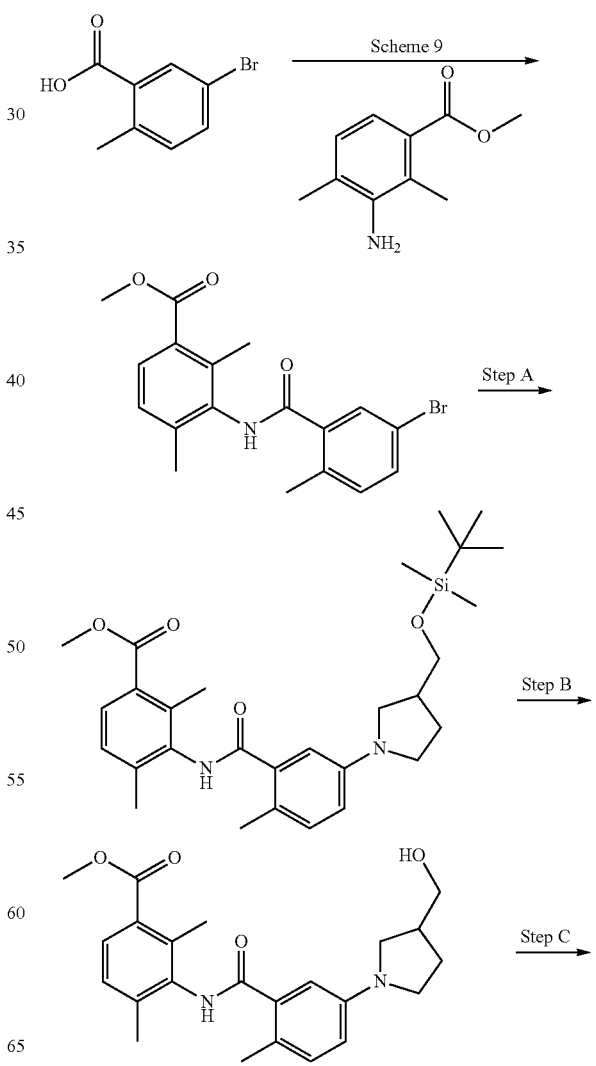

-continued

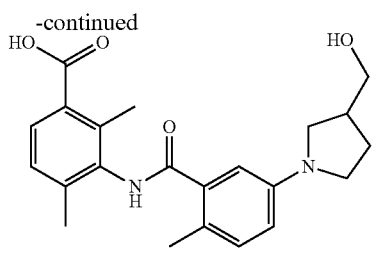

Preparation 26

Synthesis of methyl 3-[[5-[3-[[tert-butyl(dimethyl)silyl]oxymethyl]pyrrolidin-1-yl]-2-methyl-benzoyl]amino]-2,4-dimethyl-benzoate

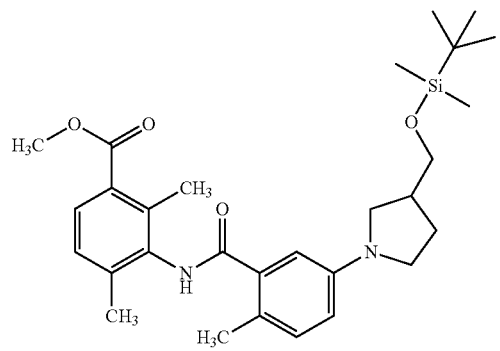 [SMILES: COC(=O)c1ccc(C)c(NC(=O)c2cc(N3CCC(CO[Si](C)(C)C(C)(C)C)C3)ccc2C)c1C]

Scheme 10, step A. To a solution of methyl 3-[(5-bromo-2-methyl-benzoyl)amino]-2,4-dimethyl-benzoate (0.5 g, 1.32 mmol), tert-butyl-dimethyl-(pyrrolidin-3-ylmethoxy)silane (0.4 g, 1.99 mmol) and $Cs_2CO_3$ (1.2 g, 3.99 mmol) in 1,4-dioxane (15 ml) is added $Pd_2(dba)_3$ (0.12 g, 0.132 mmol) followed by S-Phos (0.054 g, 0.132 mmol). The reaction mixture is purged with nitrogen for 5 minutes and then heated at 100° C. After 16 hours, the reaction is cooled to ambient temperature, filtered through Celite™, and washed with EtOAc. The combined filtrates are dried over sodium sulfate, filtered, and concentrated under reduced pressure and purified by flash chromatography (silica gel) using 20% EtOAc in hexane to afford the title compound as a brown semi solid (0.36 g, 53%). Mass spectrum (m/z): 511.2 (M+1).

Preparation 27

Synthesis of methyl 3-[[5-[3-(hydroxymethyl)pyrrolidin-1-yl]-2-methyl-benzoyl]amino]-2,4-dimethyl-benzoate

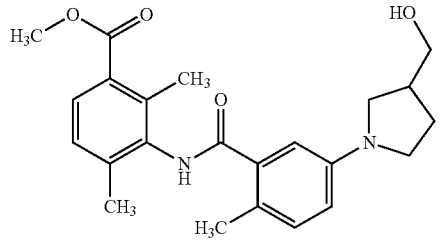

Scheme 10, step B. To a solution of methyl 3-[[5-[3-[[tert-butyl(dimethyl)silyl]oxymethyl]pyrrolidin-1-yl]-2-methyl-benzoyl]amino]-2,4-dimethyl-benzoate (0.35 g, 0.686 mmol) in THF (50 ml) is added $Bu_4NF$ 1.0 M in THF (0.537 g, 2.05 mmol) at 0° C. The reaction mixture is gradually warmed to ambient temperature. After 2 hours, the reaction mixture is diluted with ice-water and extracted twice with ethyl acetate. The organic layers are combined, dried over sodium sulfate, filtered, and concentrated under reduced pressure to give a residue. The residue is purified by flash chromatography (silica gel) over a gradient using 50% ethyl acetate in hexane to afford the title compound as a brown solid (150 mg, 51%).

EXAMPLE 6

Synthesis of 3-[[5-[3-(hydroxymethyl)pyrrolidin-1-yl]-2-methyl-benzoyl]amino]-2,4-dimethyl-benzoic acid

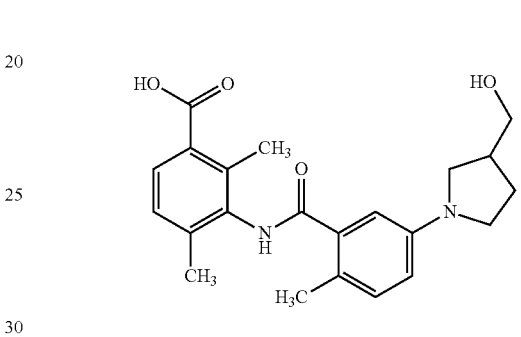

Scheme 10, step C. A solution of aqueous 5N NaOH (5.00 ml) is added to a stirred solution of methyl 3-[[5-[3-(hydroxymethyl)-1-piperidyl]-2-methyl-benzoyl]amino]-2,4-dimethyl-benzoate (0.4 g, 0.975 mmol) in MeOH (5 ml). After 5 hours at ambient temperature, the organic solvent is removed under reduced pressure and the residue is diluted with water, acidified to pH 4 with 1N HCl, and extracted twice with 10% IPA in $CH_2Cl_2$. The organic layers are combined and dried over anhydrous sodium sulfate. The solvent is removed under reduced pressure and the resulting precipitate is triturated with diethyl ether and filtered to afford the title compound as a brown solid (70 mg, 56%). Mass spectrum (m/z): 381.2 (M−1).

Scheme 11

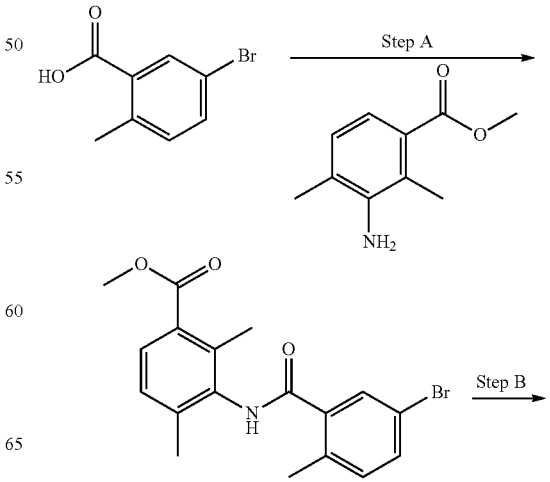

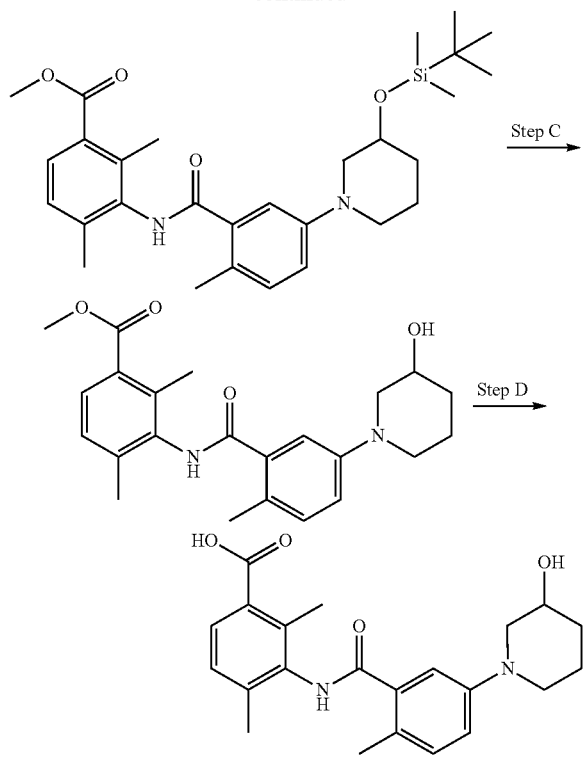

Preparation 28

Synthesis of methyl 3-[(5-bromo-2-methyl-benzoyl)amino]-2,4-dimethyl-benzoate

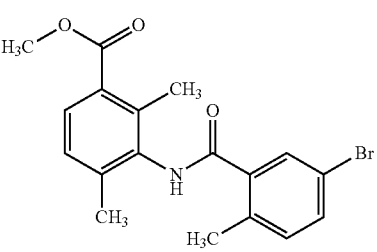

Scheme 11, step A. To a solution of 5-bromo-2-methyl-benzoic acid (2.0 g, 0.0093 mol) in $CH_2Cl_2$ (20 ml) at room temperature are added methyl 3-amino-3,5-dimethylbenzoate (1.49 g, 0.0083 mol, see preparation 12) and N,N-diisopropylethylamine (4.79 g, 0.037 mol). After stirring the reaction mixture for 10 minutes, 1-propanephosphonic acid cyclic anhydride (50% solution in ethyl acetate, 8.87 g, 0.027 mol) is added via syringe and heated at 50° C. After 16 hours, the reaction mixture is diluted with $CH_2Cl_2$, washed with water and brine. The organic layers are combined and dried over anhydrous $Na_2SO_4$, filtered, and concentrated under reduced pressure. The residue is purified by flash chromatography (silica gel) using 10% EtOAc in hexanes to give the title compound as a white powder (2.8 g, 80%).

Preparation 29

Synthesis of methyl 3-[[5-[3-[tert-butyl(dimethyl)silyl]oxy-1-piperidyl]-2-methyl-benzoyl]amino]-2,4-dimethyl-benzoate

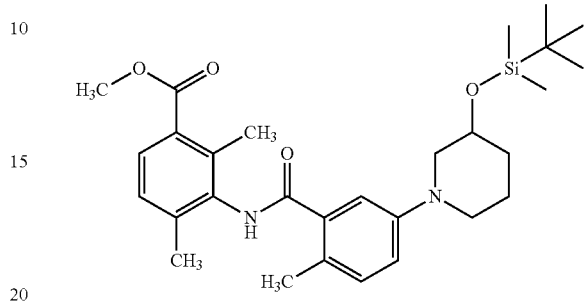

Scheme 11, step B. To a solution of methyl 3-[(5-bromo-2-methyl-benzoyl)amino]-2,4-dimethyl-benzoate (0.5 g, 1.32 mmol), tert-butyl-dimethyl-(3-piperidyloxy)silane (0.425 g, 1.98 mmol) and $Cs_2CO_3$ (1.28 g, 3.96 mmol) in 1,4-dioxane (15 ml) is added $Pd_2(dba)_3$ (0.12 g, 0.132 mmol) followed by S-Phos (0.054 g, 0.132 mmol). The reaction mixture is purged with nitrogen for 5 minutes and then heated at 100° C. After 16 hours, the reaction is cooled to ambient temperature, filtered through Celite™, and washed with EtOAc. The combined filtrates are dried over sodium sulfate, filtered, and concentrated under reduced pressure and purified by flash chromatography (silica gel) using 10% EtOAc in hexane to afford the title compound as a brown semi-solid (0.4 g, 60%).

Preparation 30

Synthesis of methyl 3-[[5-(3-hydroxy-1-piperidyl)-2-methyl-benzoyl]amino]-2,4-dimethyl-benzoate

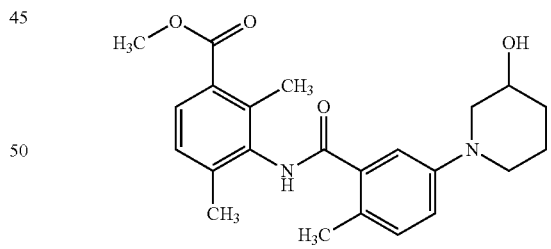

Scheme 11, step C. To a solution of methyl 3-[[5-[3-[tert-butyl(dimethyl)silyl]oxy-1-piperidyl]-2-methyl-benzoyl]amino]-2,4-dimethyl-benzoate (0.4 g, 0.78 mmol) in THF (20 ml) is added $Bu_4NF$ 1.0 M in THF (0.409 g, 1.56 mmol) at 0° C. The reaction mixture is gradually warmed to ambient temperature. After 1 hour, the reaction mixture is diluted with ice-water and extracted twice with ethyl acetate. The organic layers are combined, dried over sodium sulfate, filtered, and concentrated under reduced pressure to give a residue. The residue is purified by flash chromatography (silica gel) over a gradient using 3% methanol in dichloromethane to afford the title compound as a white solid (0.3 g, 97%).

EXAMPLE 7

Synthesis of 3-[[5-(3-hydroxy-1-piperidyl)-2-methyl-benzoyl]amino]-2,4-dimethyl-benzoic acid

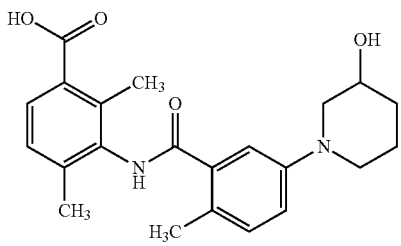 [SMILES: Cc1ccc(N2CCCC(O)C2)cc1C(=O)Nc1c(C)ccc(C(=O)O)c1C]

Scheme 11, step D. A solution of aqueous 4N NaOH (2.00 ml) is added to a stirred solution of methyl 3-[[5-(3-hydroxy-1-piperidyl)-2-methyl-benzoyl]amino]-2,4-dimethyl-benzoate (0.3 g, 0.75 mmol) in THF:MeOH (5 ml:2 ml). After 3 hours at ambient temperature, the organic solvent is removed under reduced pressure and the residue is diluted with water, acidified to pH 4 with 1N HCl, and extracted with 10% IPA in $CH_2Cl_2$. The organic layers are combined and dried over anhydrous sodium sulfate. The solvent is removed under reduced pressure and the resulting precipitate is triturated with diethyl ether and filtered to afford the title compound as an off-white solid (0.274 g, 94%). Mass spectrum (m/z): 383.2 (M+1).

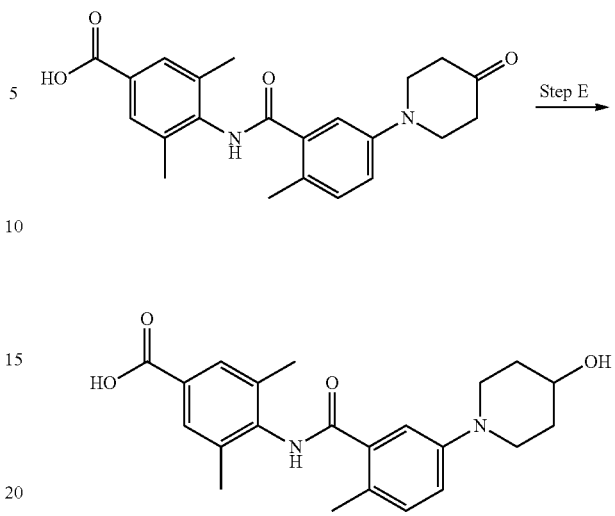

Preparation 31

Synthesis of ethyl 4-[(5-bromo-2-methyl-benzoyl)amino]-3,5-dimethyl-benzoate

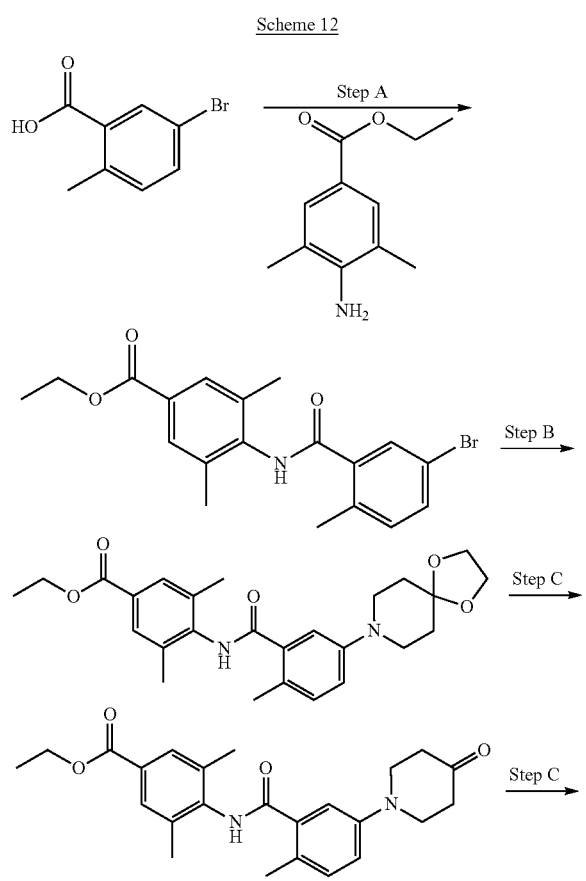

Scheme 12, step A. To a solution of 5-bromo-2-methyl-benzoic acid (1.35 g, 6.15 mmol) in THF (15 ml), $CH_2Cl_2$ (15 ml) and DMF (14.27 μl, 184.57 moles) is added dropwise oxalyl chloride (587.12 μl, 6.77 mmoles) at 0° C. and reaction mixture is slowly allowed to warm to ambient temperature. After 2 hours, the solvent is removed under reduced pressure. To the residue $CH_2Cl_2$ (30 ml) is added and reaction mixture is cooled to 0° C., then ethyl 4-amino-3,5-dimethyl-benzoate (1.19 g, 6.15 mmol) is added followed by 4-pyridinamine, N,N-dimethyl-(37.58 mg, 307.61 mmoles) and pyridine (1.49 ml, 18.46 mmoles). The cooling bath is removed and the clear solution is allowed to warm to ambient temperature. After 5 hours, the solvent is removed and the reaction mixture is diluted with ethyl acetate and washed with 1N HCl, saturated solution of sodium bicarbonate, and brine. The organic layers are combined and dried over anhydrous $Na_2SO_4$, filtered, and concentrated under reduced pressure. The resulting residue is triturated with hexanes and the resulting solids were collected by filtration to give the title compound as a white solid (1.80 g; 75.2%). Mass spectrum (m/z): 390.2 (M+1).

Preparation 32

Synthesis of ethyl 4-[[5-(1,4-dioxa-8-azaspiro[4.5]decan-8-yl)-2-methyl-benzoyl]amino]-3,5-dimethyl-benzoate

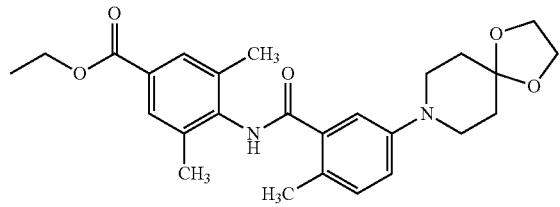 [SMILES: CCOC(=O)c1cc(C)c(NC(=O)c2cc(N3CCC4(CC3)OCCO4)ccc2C)c(C)c1]

Scheme 12, step B. To a solution of ethyl 4-[(5-bromo-2-methyl-benzoyl)amino]-3,5-dimethyl-benzoate (0.5 g, 1.28 mmol), 1,4-dioxa-8-azaspiro(4.5)decane (0.22 g, 1.54 mmol) and Cs₂CO₃ (1.25 g, 3.84 mmol) in THF (10 ml) is added Pd(OAc)₂ (0.04 g, 0.19 mmol) followed by racemic-2,2'-bis(diphenylphosphino)-1,1'-binaphthyl (119.7 mg, 0.19 mmol). The reaction mixture is purged with nitrogen for 5 minutes and then heated at 90° C. After 16 hours, the reaction is cooled to ambient temperature and diluted with ammonium chloride and extracted twice with EtOAc. The combined organic layers are dried over sodium sulfate, filtered, and concentrated under reduced pressure. The resulting residue is purified by flash chromatography (silica gel) using 0-100% ethyl acetate in hexane to afford the title compound as a brown solid (0.21 g, 36.2%). Mass spectrum (m/z): 453.2 (M+1).

Preparation 33

Synthesis of ethyl 3,5-dimethyl-4-[[2-methyl-5-(4-oxo-1-piperidyl)benzoyl]amino]benzoate

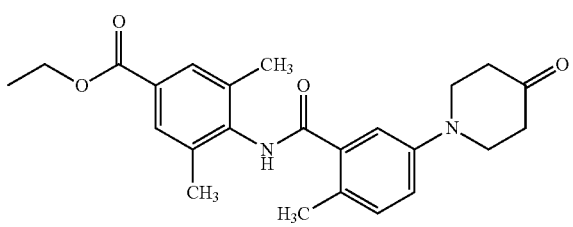 [SMILES: CCOC(=O)c1cc(C)c(NC(=O)c2cc(N3CCC(=O)CC3)ccc2C)c(C)c1]

Scheme 12, step C. To a solution of ethyl 4-[[5-(1,4-dioxa-8-azaspiro[4.5]decan-8-yl)-2-methyl-benzoyl]amino]-3,5-dimethyl-benzoate (205 mg, 452.99 µmoles) in acetone (5 ml) is added a mixture of 5M HCl (1 mL) in H₂O (1 mL) and heated to 60° C. After 12 hours, the mixture is cooled to ambient temperature, diluted with 2M NaOH to pH 6 and extracted with ethyl acetate. The combined organic layers are dried over sodium sulfate, filtered, and concentrated under reduced pressure. The resulting residue is purified by flash chromatography (silica gel) using 0-40% ethyl acetate in hexane to afford the title compound as an off-white foam (0.11 g, 61%). Mass spectrum (m/z): 409.2 (M+1).

Preparation 34

Synthesis of 3,5-dimethyl-4-[[2-methyl-5-(4-oxo-1-piperidyl)benzoyl]amino]benzoic acid

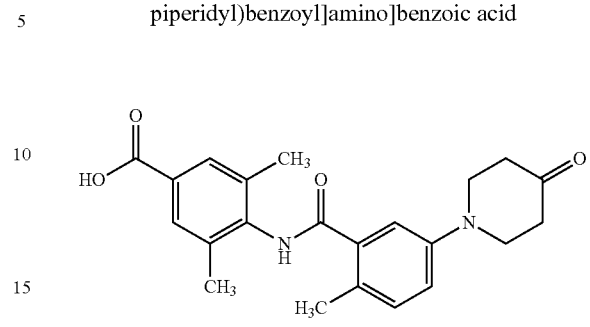

Scheme 12, step D. A solution of aqueous 2N NaOH (2.00 ml) is added to a stirred solution of ethyl 3,5-dimethyl-4-[[2-methyl-5-(4-oxo-1-piperidyl)benzoyl]amino]benzoate (0.11 g, 269.28 µmol) in THF:MeOH (2.4 ml:1.2 ml). After 16 hours at ambient temperature, the organic solvent is removed under reduced pressure and the residue is diluted with water, acidified to pH 7 with 1N HCl, and extracted twice with ethyl acetate. The organic layers are combined with aqueous layer and concentrated under reduced pressure. The resulting solids are triturated with 1:1 mixture of acetonitrile and ethanol to give white slurry that is filtered through Celite™ bed. The filtrate is concentrated under reduced pressure and the precipitate is triturated with acetone and filtered to afford the title compound as an off-white solid (99 mg, 99%). Mass spectrum (m/z): 381.2 (M+1).

EXAMPLE 8

Synthesis of 4-[[5-(4-hydroxy-1-piperidyl)-2-methyl-benzoyl]amino]-3,5-dimethyl-benzoic acid

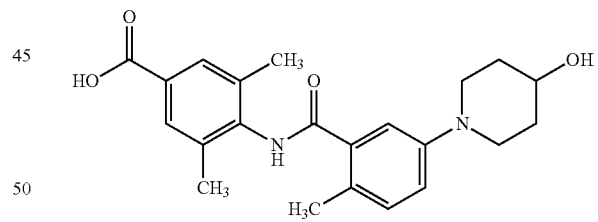

Scheme 12, step E. To a solution of 3,5-dimethyl-4-[[2-methyl-5-(4-oxo-1-piperidyl)benzoyl]amino]benzoic acid (69.5 mg, 182.68 moles) in methanol (1.83 ml) is added sodium tetrahydroborate (13.82 mg, 365.36 moles) and the resulting mixture is stirred at ambient temperature. After 1 hour, the mixture is quenched with saturated solution of NH₄Cl (0.2 ml) and extracted with CHCl₃ (3 ml):IPA (1 ml). The combined organic layers are dried over sodium sulfate, filtered, and concentrated under reduced pressure. The resulting solid is triturated with H₂O (5 ml), filtered, and washed with H₂O (5 ml). The residue is purified by reverse phase chromatography (C18) using 20% acetonitrile in H₂O with 0.1% formic acid to afford the title compound as a white powder (0.01 g, 15.7%). Mass spectrum (m/z): 383.2 (M+1).

Scheme 13

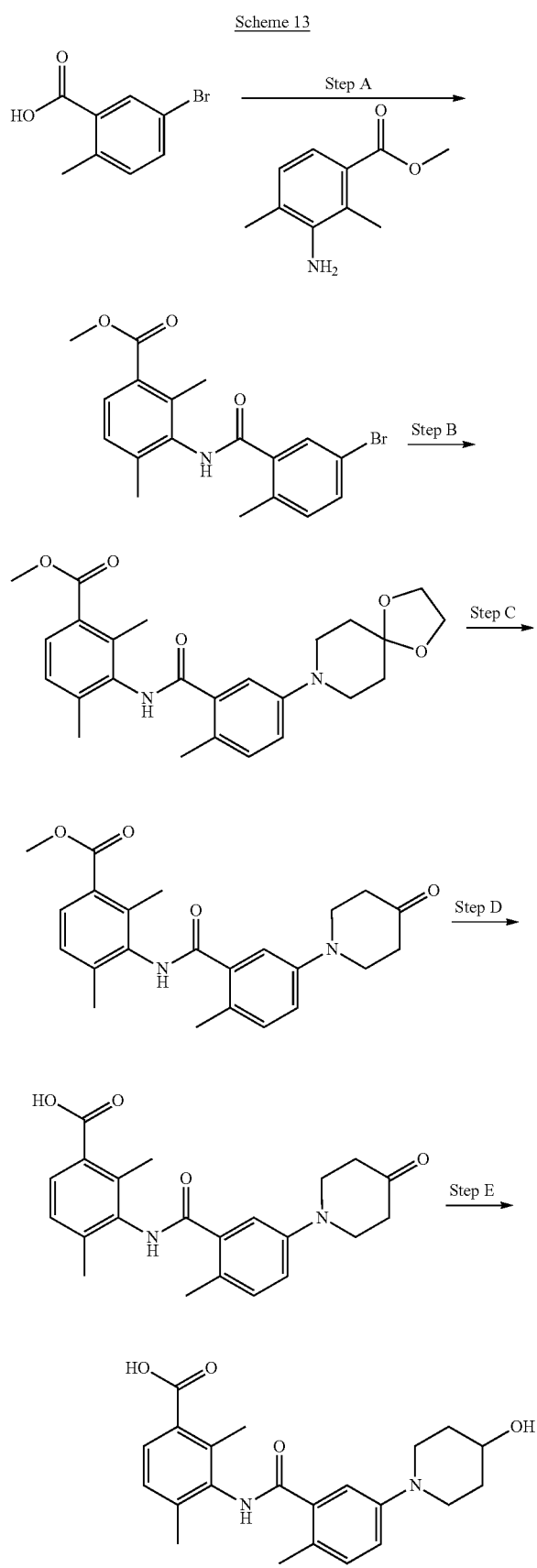

Preparation 35

Synthesis of methyl 3-[(5-bromo-2-methyl-benzoyl)amino]-2,4-dimethyl-benzoate

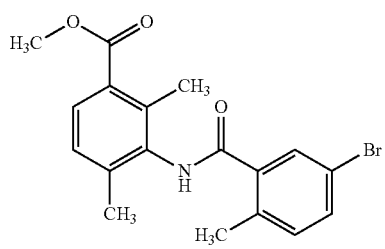 [SMILES: COC(=O)c1ccc(C)c(NC(=O)c2cc(Br)ccc2C)c1C]

Scheme 13, step A. To a solution of 5-bromo-2-methyl-benzoic acid (2.45 g, 11.16 mmol) in THF (10 ml), $CH_2Cl_2$ (10 ml) and DMF (20.00 μl, 258.65 moles) is added dropwise oxalyl chloride (1.16 ml, 13.39 mmoles) at 0° C. and the reaction mixture is slowly allowed to warm to ambient temperature. After 2 hours, the solvent is removed under reduced pressure. To the residue is added $CH_2Cl_2$ (40 ml) and the reaction mixture is cooled to 0° C., then ethyl 4-amino-3,5-dimethyl-benzoate (2 g, 11.16 mmol) is added followed by N,N-dimethylpyridin-4-amine (13.63 mg, 0.11 mmoles) and pyridine (2.71 ml, 33.48 mmoles). The cooling bath is removed and the clear solution is allowed to warm to ambient temperature. After 2 hours, the solvent is removed and the reaction mixture is diluted with ethyl acetate and washed with 1N HCl, a saturated solution of sodium bicarbonate, and brine. The organic layers are combined, dried over anhydrous $Na_2SO_4$, filtered, and concentrated under reduced pressure to give the title compound as a light yellow solid (4.0 g; 95.5%). Mass spectrum (m/z): 376.0 (M+1).

Preparation 36

Synthesis of methyl 3-[[5-(1,4-dioxa-8-azaspiro[4.5]decan-8-yl)-2-methyl-benzoyl]amino]-2,4-dimethyl-benzoate

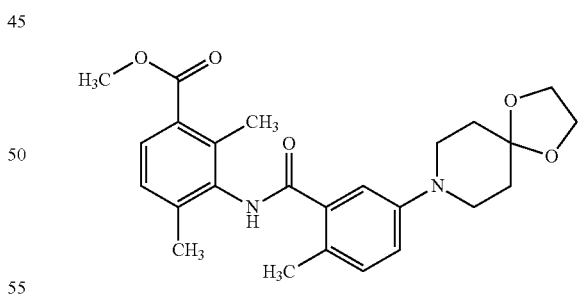

Scheme 13, step B. To a solution of methyl 3-[(5-bromo-2-methyl-benzoyl)amino]-2,4-dimethyl-benzoate (0.5 g, 1.33 mmol), 1,4-dioxa-8-azaspiro(4.5)decane (228.34 mg, 1.59 mmol) and $Cs_2CO_3$ (1.3 g, 3.99 mmol) in 1,4-dioxane (10 ml) is added Pd(OAc)$_2$ (29.84 mg, 132.89 μmol) followed by racemic-2,2'-bis(diphenylphosphino)-1,1'-binaphthyl (82.75 mg, 132.89 μmol). The reaction mixture is purged with nitrogen for 10 minutes and then heated to 90° C. After 3 hours, very small amount of the product is formed. To the reaction mixture is added Pd(OAc)$_2$ (29.84 mg, 132.89 μmol) followed by racemic-2,2'-bis(diphenylphosphino)-1,1'-binaphthyl (82.75 mg, 132.89 μmol) and heated to 100° C. After 12 hours, the reaction is cooled to ambient temperature and diluted with water and extracted with EtOAc. The combined organic layers are washed with brine, dried over sodium sulfate, filtered, and concentrated under reduced pressure. The resulting residue is purified by flash chromatography (silica gel) using 0-100% ethyl acetate in hexane to afford the title compound as a brown solid (0.26 g, 44.62%). Mass spectrum (m/z): 439.2 (M+1).

Preparation 37

Synthesis of methyl 2,4-dimethyl-3-[[2-methyl-5-(4-oxo-1-piperidyl)benzoyl]amino]benzoate

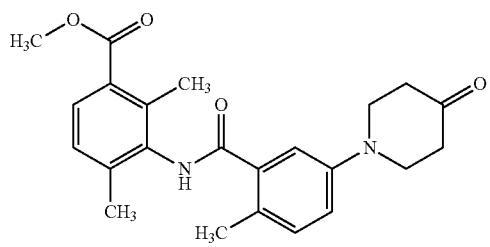 [SMILES: COC(=O)c1ccc(C)c(NC(=O)c2cc(N3CCC(=O)CC3)ccc2C)c1C]

Scheme 13, step C. To a solution of methyl 3-[[5-(1,4-dioxa-8-azaspiro[4.5]decan-8-yl)-2-methyl-benzoyl]amino]-2,4-dimethyl-benzoate (250 mg, 570.09 moles) in THF (2 ml) is added 4M HCl (1 ml) and stirred at ambient temperature. The mixture is concentrated under reduced pressure and re-dissolved in acetone (5 ml) followed by the addition of 5N HCl (1 ml). After 22 hours at 60° C., the mixture is cooled to ambient temperature and diluted with 2M NaOH to pH 6 and extracted twice with ethyl acetate. The combined organic layers are dried over sodium sulfate, filtered, and concentrated under reduced pressure. The resulting residue is purified by flash chromatography (silica gel) using 0-50% ethyl acetate in hexane to afford the title compound as an off-white foam (0.12 g, 53.36%). Mass spectrum (m/z): 395.2 (M+1).

Preparation 38

Synthesis of 2,4-dimethyl-3-[[2-methyl-5-(4-oxo-1-piperidyl)benzoyl]amino]benzoic acid

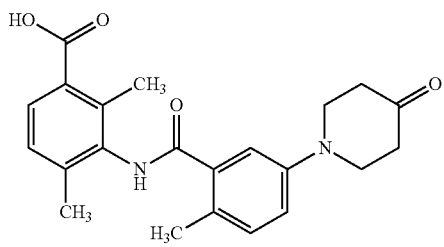 [SMILES: Cc1ccc(N2CCC(=O)CC2)cc1C(=O)Nc1c(C)ccc(C(=O)O)c1C]

Scheme 13, step D. A solution of aqueous 2N NaOH (1.00 ml) is added to a stirred solution of methyl 2,4-dimethyl-3-[[2-methyl-5-(4-oxo-1-piperidyl)benzoyl]amino]benzoate (0.12 g, 304.20 μmol) in THF:MeOH (2 ml:1 ml). After 16 hours at ambient temperature, the organic solvent is removed under reduced pressure and the residue is diluted with water, acidified to pH 6 with 1N HCl, and extracted with ethyl acetate. The organic layers are combined with aqueous layer and concentrated under reduced pressure. The resulting solids are dissolved in acetonitrile/$H_2O$ and lyophilized to afford the title compound as an off-white solid (58 mg, 50.12%). Mass spectrum (m/z): 381.2 (M+1).

EXAMPLE 9

Synthesis of 3-[[5-(4-hydroxy-1-piperidyl)-2-methyl-benzoyl]amino]-2,4-dimethyl-benzoic acid

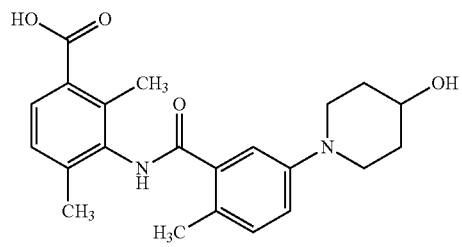 [SMILES: Cc1ccc(N2CCC(O)CC2)cc1C(=O)Nc1c(C)ccc(C(=O)O)c1C]

Scheme 13, step E. To a solution of 2,4-dimethyl-3-[[2-methyl-5-(4-oxo-1-piperidyl)benzoyl]amino]benzoic acid (51 mg, 134.05 μmoles) in methanol (1.34 ml) is added sodium tetrahydroborate (10.14 mg, 268.11 moles) and the mixture is stirred at ambient temperature. After 1 hour, the mixture is quenched and adjusted to pH7 with saturated solution of $NH_4Cl$ and extracted twice with $CHCl_3$ (3 ml):IPA(1 ml). The combined organic layers are dried over sodium sulfate, filtered, and concentrated under reduced pressure. The solid is re-dissolved in 3:1 $CHCl_3$:IPA and diluted with HCl to pH2 and extracted with 3:1 $CHCl_3$:IPA. The combined organic layers are dried over sodium sulfate, filtered, and concentrated under reduced pressure. The resulting residue is taken up in MeOH and filtered through cotton plug. The filtrate is concentrated under reduced pressure followed by dissolution in $H_2O$ and lyophilized for 12 hours to afford the title compound as an off-white powder (0.04 g, 81.9%). Mass spectrum (m/z): 383.2 (M+1).

Scheme 14

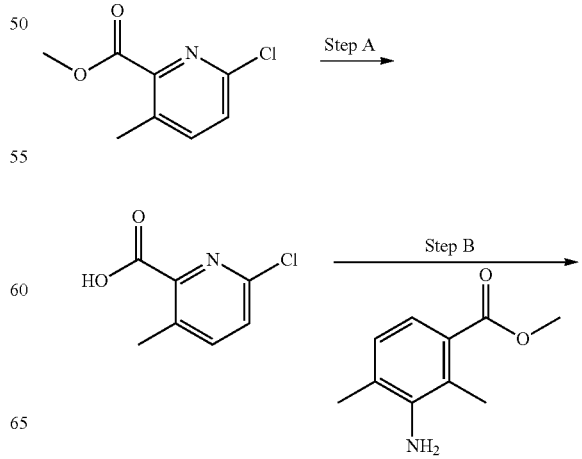

-continued

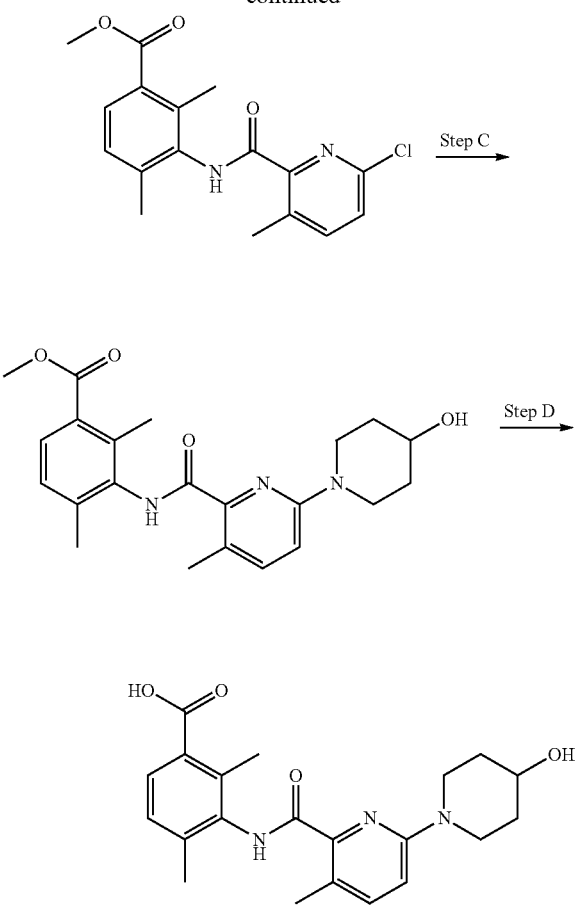

Preparation 39

Synthesis of 6-chloro-3-methyl-pyridine-2-carboxylic acid

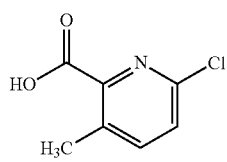

Scheme 14, step A. A solution of aqueous 1N NaOH (10.00 ml) is added to a stirred solution of methyl 6-chloro-3-methyl-pyridine-2-carboxylate (1.0 g, 5.39 mmoles) in THF:MeOH (10 ml:2 ml). The mixture is stirred at room temperature for 3 hours. The organic solvent is removed under reduced pressure and the semi-solid is dissolved in water and acidified to pH 1-2 with aqueous 1N HCl. The resulting precipitate is filtered, washed with water, and dried at 40° C. in vacuum oven for 12 hours to give the title compound as a white solid (780 mg, 84%). Mass spectrum (m/z): 172.0 (M+1).

Preparation 40

Synthesis of methyl 3-[(6-chloro-3-methyl-pyridine-2-carbonyl)amino]-2,4-dimethyl-benzoate

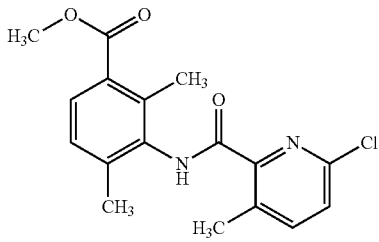 [SMILES: COC(=O)c1ccc(C)c(NC(=O)c2nc(Cl)ccc2C)c1C]

Scheme 14, step B. To a solution of 6-chloro-3-methyl-pyridine-2-carboxylic acid (0.35 g, 0.20 mmol) in CH$_2$Cl$_2$ (6 ml) at room temperature are added methyl 3-amino-3,5-dimethylbenzoate (0.36 g, 0.20 mmol, see preparation 12), and N,N-diisopropylethylamine (0.77 g, 0.60 mmol). After stirring the reaction mixture for 10 minutes, 1-propanephosphonic acid cyclic anhydride (50% solution in ethyl acetate, 2.54 g, 0.80 mmol) is added via syringe. After 16 hours at ambient temperature, the reaction mixture is diluted with CH$_2$Cl$_2$, washed with water and brine. The organic layers are combined and dried over anhydrous Na$_2$SO$_4$, filtered, and concentrated under reduced pressure to give the title compound as a white powder (0.52 g, 76%). Mass spectrum (m/z): 333.2 (M+1).

Preparation 41

Synthesis of tert-butyl-dimethyl-(4-piperidyloxy)silane

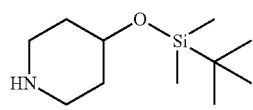

Scheme 14, step C. To a solution of 4-hydroxypiperidine (2.00 g, 9.89 mmoles) in CH$_2$Cl$_2$ (30 mL) is added 1H-imidazole (2.69 g, 39.55 mmoles) followed by t-butyldimethylchlorosilane (3.58 g, 23.73 mmoles) and the reaction mixture is stirred at room temperature. After 12 hours, the reaction mixture is washed with water, saturated solution of NaHCO$_3$, and brine. The organic layers are combined and dried over sodium sulfate, filtered, and concentrated under reduced pressure. The resulting residue is purified by flash chromatography (silica gel) over a gradient using 100% CH$_2$Cl$_2$ to 10% 7N ammonia in MeOH/90% CH$_2$Cl$_2$ to afford the title compound (3.69 g, 86.3%). Mass spectrum (m/z): 216.2 (M+1).

Preparation 42

Synthesis of methyl 3-[[6-(4-hydroxy-1-piperidyl)-3-methyl-pyridine-2-carbonyl]amino]-2,4-dimethyl-benzoate

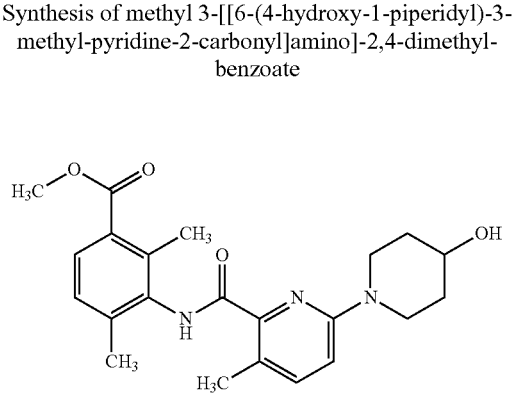

Scheme 14, step C. To a solution of methyl 3-(6-chloro-3-methylpicolinamido)-2,4-dimethylbenzoate (0.50 g, 0.0015 mol), tert-butyl-dimethyl-(4-piperidyloxy)silane (0.90 g, 0.0045 mol) and Cs$_2$CO$_3$ (2.00 g, 0.006 mol) in toluene (6 ml) is added Pd$_2$(dba)$_3$ (0.14 g, 0.00015 mol) followed by BINAP (0.086 g, 0.00015 mol). The reaction mixture is purged with nitrogen for 5 minutes and then heated at 120° C. After 4 hours, the reaction is cooled to ambient temperature, filtered through Celite™, and washed with EtOAc. The combined filtrate is dried over sodium sulfate, filtered, and concentrated under reduced pressure to afford the title compound as a white semi-solid (0.220 g, 29%). Mass spectrum (m/z): 398.2 (M+1).

EXAMPLE 10

Synthesis of 3-[[6-(4-hydroxy-1-piperidyl)-3-methyl-pyridine-2-carbonyl]amino]-2,4-dimethyl-benzoic acid

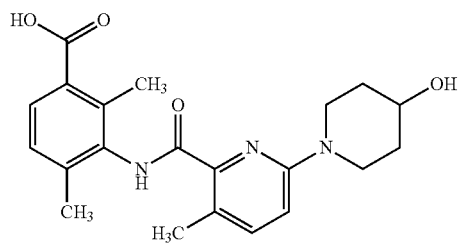 [SMILES: Cc1ccc(N2CCC(O)CC2)nc1C(=O)Nc1c(C)ccc(C(=O)O)c1C]

Scheme 14, step D. A solution of aqueous 2N NaOH (2.00 ml) is added to a stirred solution of methyl 3-[[6-(4-hydroxy-1-piperidyl)-3-methyl-pyridine-2-carbonyl]amino]-2,4-dimethyl-benzoate (0.21 g, 0.52 mmol) in THF:MeOH (3 ml:1 ml). After 16 h at ambient temperature, the organic solvent is removed under reduced pressure and the residue is diluted with water, acidified to pH 6 with aqueous 1N HCl, and extracted with ethyl acetate (2×20 ml). The organic layers are combined and dried over anhydrous sodium sulfate. The solvent is removed under reduced pressure and the resulting precipitate is triturated with pentane and filtered to afford the title compound as a white solid (0.082 g, 39%). Mass spectrum (m/z): 384.2 (M+1).

Scheme 15

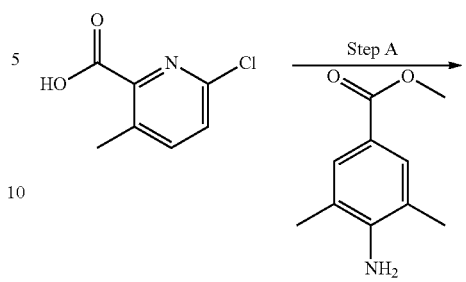

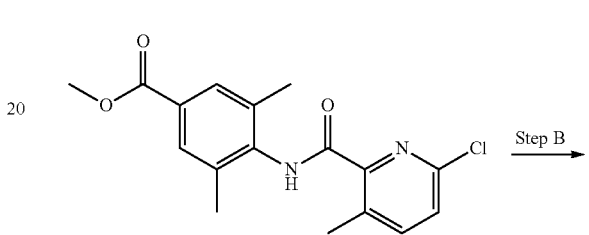

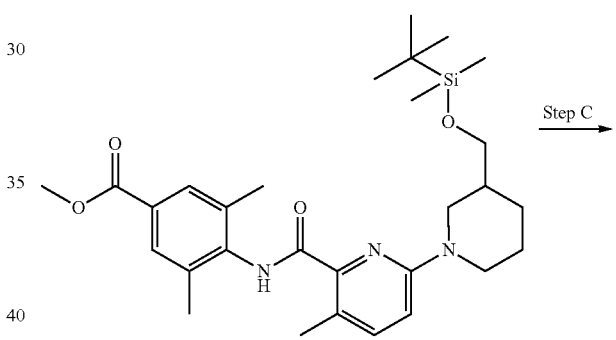

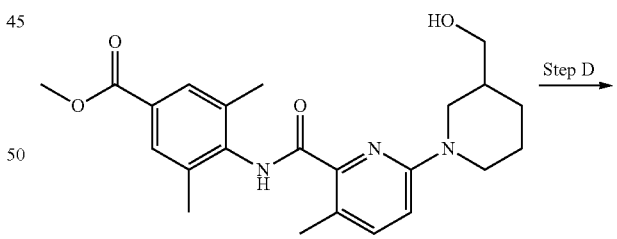

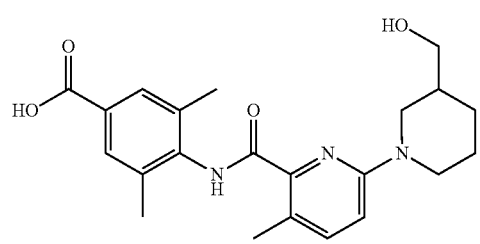

Preparation 43

Synthesis of methyl 4-[(6-chloro-3-methyl-pyridine-2-carbonyl)amino]-3,5-dimethyl-benzoate

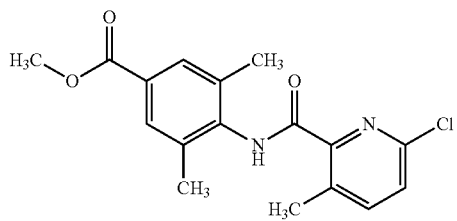 [SMILES: COC(=O)c1cc(C)c(NC(=O)c2nc(Cl)ccc2C)c(C)c1]

Scheme 15, step A. To a solution of 6-chloro-3-methyl-pyridine-2-carboxylic acid (0.70 g, 4.093 mmol, see preparation 1) in $CH_2Cl_2$ (6 mL) at 0° C. are added methyl 4-amino-3,5-dimethylbenzoate (0.74 g, 4.093 mmol, see preparation 12), and triethylamine (0.83 g, 8.187 mmol). After stirring the reaction mixture for 10 minutes, 1-propanephosphonic acid cyclic anhydride (50% solution in ethyl acetate, 2.60 g, 8.187 mmol) is added via syringe and stirred at ambient temperature. After 12 hours, the solvent is removed under reduced pressure and the residue is diluted with water and extracted with ethyl acetate. The organic layers are combined and dried over anhydrous $Na_2SO_4$, filtered, and concentrated under reduced pressure. The resulting residue is purified by flash chromatography (silica gel) using a gradient of 0-40% ethyl acetate in hexanes to give the title compound as an off-white solid (1.10 g, 81%). Mass spectrum (m/z): 333.2 (M+1).

Preparation 44

Synthesis of tert-butyl-dimethyl-(3-piperidylmethoxy)silane

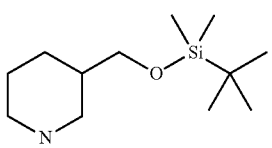

Scheme 15, step B. To a solution of piperidin-3-ylmethanol (2.10 g, 0.018 mol) in $CH_2Cl_2$ (20 mL) is added triethylamine (5.53 g, 0.0547 mol) followed by t-butyldimethylchlorosilane (4.127 g, 0.0275 mol) and the reaction mixture is stirred at room temperature. After 24 hours, the reaction mixture is washed with water, saturated solution of $NaHCO_3$, and brine. The combined organic layers are dried over sodium sulfate, filtered, and concentrated under reduced pressure. The resulting residue is purified by flash chromatography (silica gel) over a gradient using 0-10% MeOH in dichloromethane to afford the title compound (2.50 g, 60%). Mass spectrum (m/z): 231.2 (M+1).

Preparation 45

Synthesis of methyl 4-[[6-[3-[[tert-butyl(dimethyl)silyl]oxymethyl]-1-piperidyl]-3-methyl-pyridine-2-carbonyl]amino]-3,5-dimethyl-benzoate

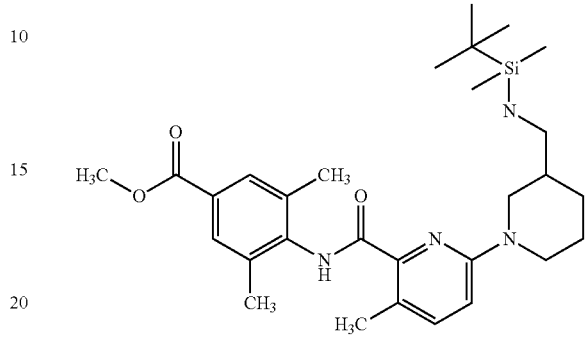

Scheme 15, step B. To a solution of methyl 4-(6-chloro-3-methylpicolinamido)-2,4-dimethylbenzoate (0.50 g, 0.0015 mol), tert-butyl-dimethyl-(3-piperidylmethoxy)silane (0.42 g, 0.0018 mol) and $Cs_2CO_3$ (1.96 g, 0.0060 mol) in 1,4-dioxane (20 ml) is added $Pd_2(dba)_3$ (0.14 g, 0.00015 mol) followed by S-Phos (0.062 g, 0.00015 mol). The reaction mixture is purged with nitrogen for 5 minutes and then heated at 80° C. After 24 hours, the reaction is cooled to ambient temperature, filtered through Celite™, and washed with EtOAc. The combined filtrates are dried over sodium sulfate, filtered, and concentrated under reduced pressure. The resulting residue is purified by flash chromatography (silica gel) to afford the title compound as a white semi-solid (0.230 g, 30%). Mass spectrum (m/z): 526.5 (M+1).

Preparation 46

Synthesis of methyl 4-[[6-[3-(hydroxymethyl)-1-piperidyl]-3-methyl-pyridine-2-carbonyl]amino]-3,5-dimethyl-benzoate

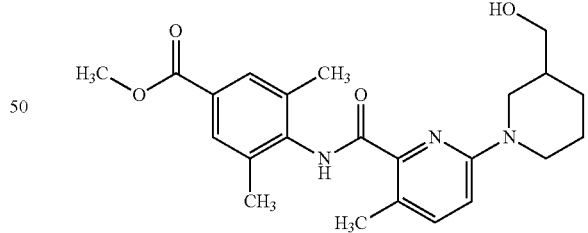

Scheme 15, step C. To a solution of methyl 4-[[6-[3-[[tert-butyl(dimethyl)silyl]oxymethyl]-1-piperidyl]-3-methyl-pyridine-2-carbonyl]amino]-3,5-dimethyl-benzoate (0.22 g, 0.873 mmol) in THF (3 ml) is added $Bu_4NF$ 1.0 M in THF (2.00 ml) at 0° C. The reaction mixture is gradually warmed to ambient temperature. After 8 hours, the reaction mixture is diluted with ice-water and extracted twice with ethyl acetate. The organic layers are combined, dried over sodium sulfate, filtered, and concentrated under reduced pressure to give a residue. The residue is purified by flash chromatography (silica gel) over a gradient using 0-40% ethyl acetate in hex-

EXAMPLE 11

Synthesis of 4-[[6-[3-(hydroxymethyl)-1-piperidyl]-3-methyl-pyridine-2-carbonyl]amino]-3,5-dimethyl-benzoic acid

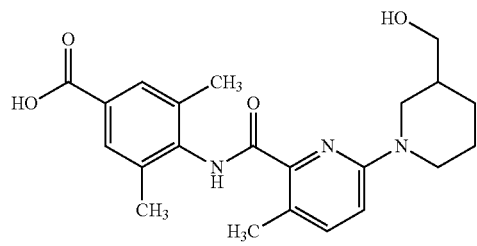

Scheme 15, step D. A solution of aqueous 2N NaOH (2.00 ml) is added to a stirred solution of methyl 4-(6-(3-(hydroxymethyl)piperidin-1-yl)-3-methylpicolinamido)-3,5-dimethylbenzoate (0.06 g, 0.146 mmol) in THF:MeOH (4 ml:1 ml). After 12 hours at ambient temperature, the organic solvent is removed under reduced pressure and the residue is diluted with water, acidified to pH 3 with aqueous citric acid solution, and extracted with ethyl acetate (2×10 ml). The organic layers are combined and dried over anhydrous sodium sulfate. The solvent is removed under reduced pressure and the resulting precipitate is triturated with pentane and filtered to afford the title compound as an off-white solid (0.03 g, 48%). Mass spectrum (m/z): 398.2 (M+1).

Scheme 16

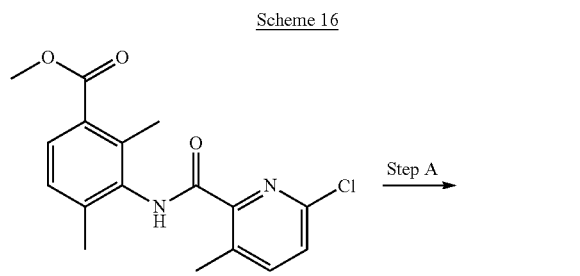

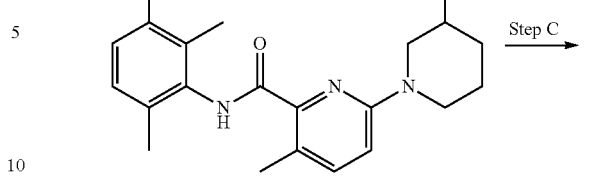

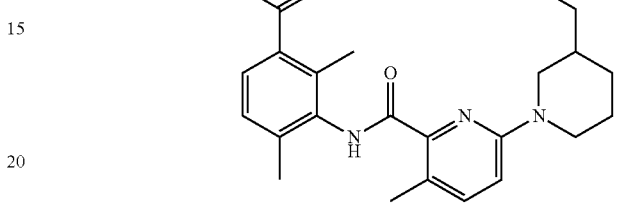

Preparation 47

Synthesis of methyl 3-[[6-[3-[[tert-butyl(dimethyl)silyl]oxymethyl]-1-piperidyl]-3-methyl-pyridine-2-carbonyl]amino]-2,4-dimethyl-benzoate

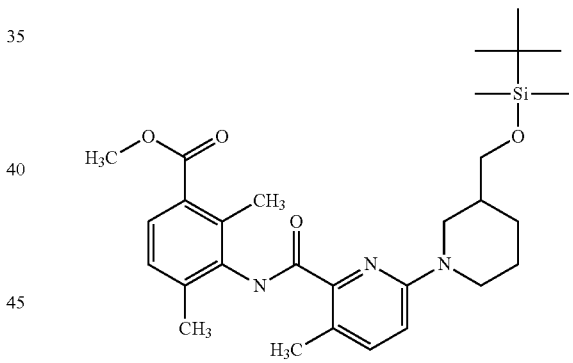

Scheme 16, step A. To a solution of methyl 3-[(6-chloro-3-methyl-pyridine-2-carbonyl)amino]-2,4-dimethyl-benzoate (0.5 g, 0.0015 mol, see preparation 40), tert-butyl-dimethyl-(3-piperidylmethoxy)silane (0.41 g, 0.0018 mol, see preparation 14) and $Cs_2CO_3$ (1.95 g, 0.006 mol) in 1,4-dioxane (20 ml) is added $Pd_2(dba)_3$ (0.137 g, 0.00015 mol) followed by S-Phos (0.06 g, 0.00015 mol). The reaction mixture is purged with nitrogen for 5 minutes and then heated at 80° C. After 24 hours, the reaction is cooled to ambient temperature, filtered through Celite™, and washed with EtOAc. The combined filtrates are dried over sodium sulfate, filtered, and concentrated under reduced pressure and purified by flash chromatography (silica gel) using 20% EtOAc in hexane to afford the title compound as a brown semi-solid (0.2 g, 38%). Mass spectrum (m/z): 525.2 (M+1).

Preparation 48

Synthesis of methyl 3-[[6-[3-(hydroxymethyl)-1-piperidyl]-3-methyl-pyridine-2-carbonyl]amino]-2,4-dimethyl-benzoate

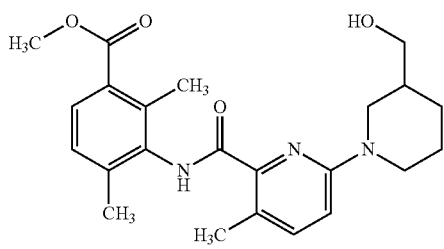 [SMILES: COC(=O)c1ccc(C)c(NC(=O)c2nc(N3CCCC(CO)C3)ccc2C)c1C]

Scheme 16, step B. To a solution of methyl 3-[[6-[3-[[tert-butyl(dimethyl)silyl]oxymethyl]-1-piperidyl]-3-methyl-pyridine-2-carbonyl]amino]-2,4-dimethyl-benzoate (0.20 g, 0.38 mmol) in THF (4 ml) is added Bu$_4$NF 1.0 M in THF (1.5 ml) at 0° C. The reaction mixture is gradually warmed to ambient temperature. After 8 hours, the reaction mixture is diluted with ice-water and extracted with ethyl acetate. The organic layers are combined, dried over sodium sulfate, filtered, and concentrated under reduced pressure. The resulting residue is purified by flash chromatography (neutral alumina) over a gradient using 50% ethyl acetate in hexane to afford the title compound as a white solid (0.18 g, 115%). Mass spectrum (m/z): 412.2 (M+1).

EXAMPLE 12

Synthesis of 3-[[6-[3-(hydroxymethyl)-1-piperidyl]-3-methyl-pyridine-2-carbonyl]amino]-2,4-dimethyl-benzoic acid

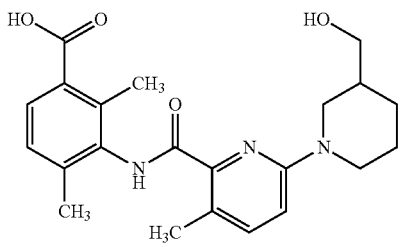

Scheme 16, step C. A solution of aqueous 2N NaOH (3.00 ml) is added to a stirred solution of methyl 3-[[6-[3-(hydroxymethyl)-1-piperidyl]-3-methyl-pyridine-2-carbonyl]amino]-2,4-dimethyl-benzoate (0.18 g, 0.437 mmol) in THF (8 ml). After 12 hours at ambient temperature, the organic solvent is removed under reduced pressure and the residue is diluted with water, acidified to pH 4 with citric acid, and extracted with ethyl acetate. The organic layers are combined and dried over anhydrous sodium sulfate. The solvent is removed under reduced pressure and the resulting residue is purified by preparative HPLC to afford the title compound as off white solid (57 mg, 14%). Mass spectrum (m/z): 398.2 (M+1).

Scheme 17

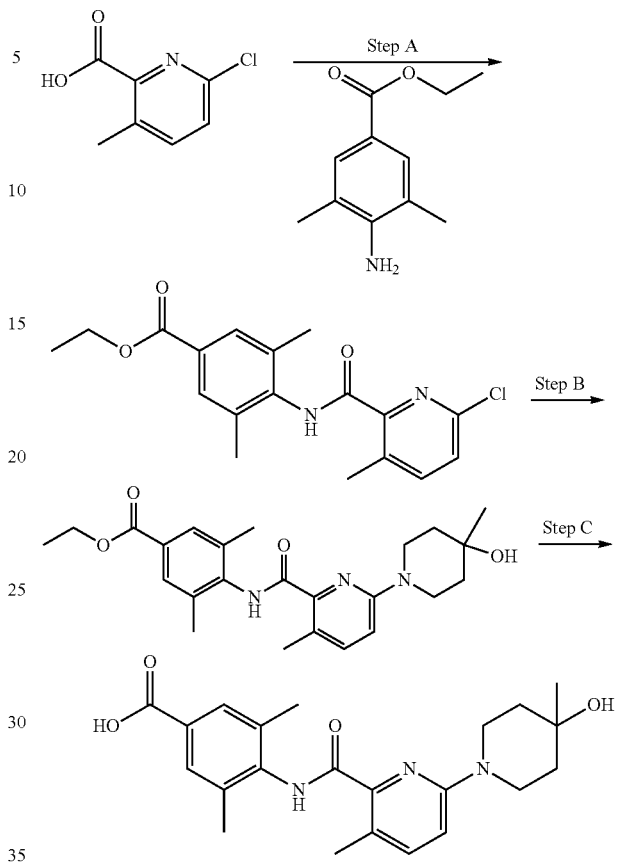

Preparation 49

Synthesis of ethyl 4-[(6-chloro-3-methyl-pyridine-2-carbonyl)amino]-3,5-dimethyl-benzoate

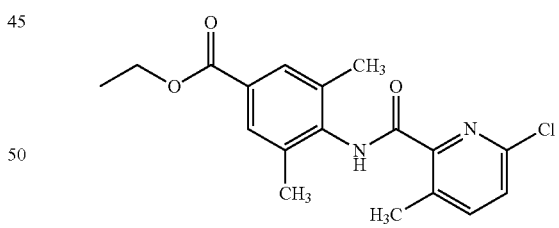

Scheme 17, step A. To a solution of 6-chloro-3-methyl-pyridine-2-carboxylic acid (465 mg, 2.71 mmol) in THF (5 ml), CH$_2$Cl$_2$ (5 ml) and DMF (0.01 ml, 129.33 moles) is added dropwise oxalyl chloride (0.3 ml, 3.46 mmoles) at 0° C. and reaction mixture is slowly allowed to warm to ambient temperature. After 2 hours, the solvent is removed under reduced pressure and the residue. To the residue CH$_2$Cl$_2$ (20 ml) is added and reaction mixture is cooled to 0° C., then ethyl 4-amino-3,5-dimethyl-benzoate (520 mg, 2.69 mmol) is added followed by N,N-dimethylpyridin-4-amine (15 mg, 122.78 moles) and Pyridine (0.66 ml, 8.16 mmoles). The cooling bath is removed and the clear yellow solution is allowed to warm to ambient temperature. After 1 hour, the solvent is removed and the reaction mixture is diluted with ethyl acetate and washed with 0.5N HCl, saturated solution of sodium bicarbonate, and brine. The organic layers are combined and dried over anhydrous Na$_2$SO$_4$, filtered, and concentrated under reduced pressure. The residue is purified by flash chromatography (silica gel) using 0-50% ethyl acetate in hexanes to give the title compound as a solid (790 mg, 84%). Mass spectrum (m/z): 347.2 (M+1).

Preparation 50

Synthesis of ethyl 4-[[6-(4-hydroxy-4-methyl-1-piperidyl)-3-methyl-pyridine-2-carbonyl]amino]-3,5-dimethyl-benzoate

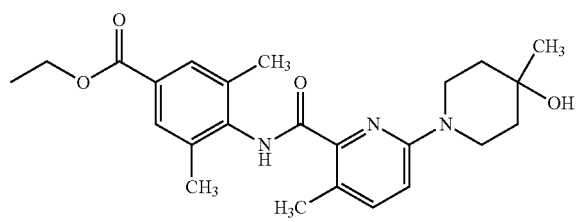 [SMILES: CCOC(=O)c1cc(C)c(NC(=O)c2nc(N3CCC(C)(O)CC3)ccc2C)c(C)c1]

Scheme 17, step B. To a solution of ethyl 4-[(6-chloro-3-methyl-pyridine-2-carbonyl)amino]-3,5-dimethyl-benzoate (275 mg, 792.93 mmoles), 4-methylpiperidin-4-ol (120 mg, 1.04 mmol) and Cs$_2$CO$_3$ (0.8 g, 2.46 mmol) in 1,4-dioxane (6 ml) is added Pd(OAc)$_2$ (27 mg, 120.26 μmoles) followed by racemic-2,2'-bis(diphenylphosphino)-1,1'-binaphthyl (54 mg, 86.72 moles). The reaction mixture is purged with nitrogen for 5 minutes and then heated to reflux. After 2 hours, the reaction is cooled to ambient temperature and diluted with ammonium chloride and extracted twice with EtOAc. The combined organic layers are dried over sodium sulfate, filtered, and concentrated under reduced pressure. The resulting residue is purified by flash chromatography (silica gel) using 0-70% ethyl acetate in hexane to afford the title compound as a yellow oil (0.27 g, 80%). Mass spectrum (m/z): 426.2 (M+1).

EXAMPLE 13

Synthesis of 4-[[6-(4-hydroxy-4-methyl-1-piperidyl)-3-methyl-pyridine-2-carbonyl]amino]-3,5-dimethyl-benzoic acid

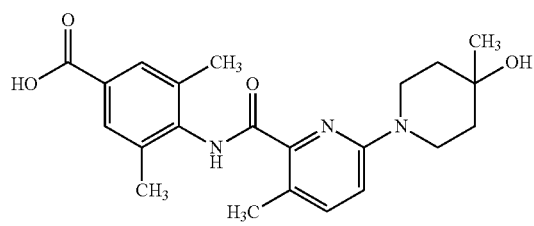 [SMILES: Cc1ccc(N2CCC(C)(O)CC2)nc1C(=O)Nc1c(C)cc(C(=O)O)cc1C]

Scheme 17, step C. A solution of aqueous 2N NaOH (5.00 ml) is added to a stirred solution of ethyl 4-[[6-(4-hydroxy-4-methyl-1-piperidyl)-3-methyl-pyridine-2-carbonyl]amino]-3,5-dimethyl-benzoate (0.27 g, 634.51 mmol) in THF:MeOH (10 ml:5 ml). After 1 hour at 50° C., the organic solvent is removed under reduced pressure and the residue is diluted with water, acidified to pH 6 with 5N HCl, and extracted with ethyl acetate. The organic layers are combined with aqueous layer and concentrated under reduced pressure. The solids are triturated with acetone/acetonitrile and filtered. The filtrate is dried over sodium sulfate, filtered, and concentrated under reduced pressure to afford the title compound as an off-white solid (0.11 g, 43.6%). Mass spectrum (m/z): 398.2 (M+1).

Scheme 18

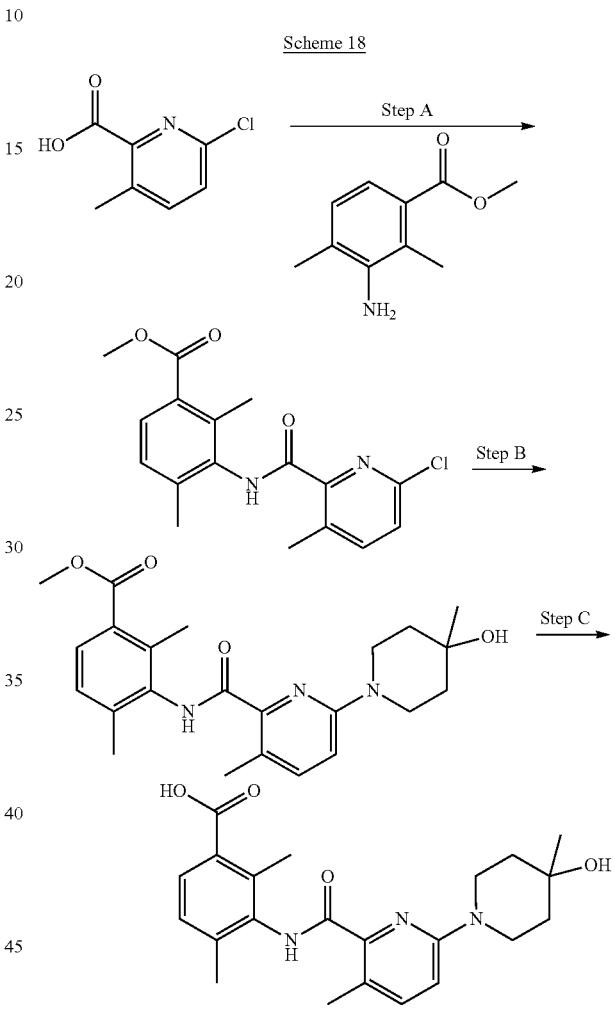

Preparation 51

Synthesis of methyl 3-[(6-chloro-3-methyl-pyridine-2-carbonyl)amino]-2,4-dimethyl-benzoate

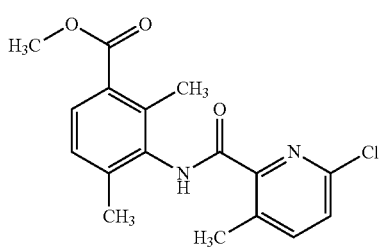

Scheme 18, step A. To a solution of 6-chloro-3-methyl-pyridine-2-carboxylic acid (465 mg, 2.71 mmol) in THF (5 ml), CH$_2$Cl$_2$ (5 ml) and DMF (0.01 ml, 129.33 moles) is added dropwise oxalyl chloride (0.3 ml, 3.46 mmoles) at 0° C. and the reaction mixture is slowly allowed to warm to ambient temperature. After 2 hours, the solvent is removed under reduced pressure. To the residue CH$_2$Cl$_2$ (20 ml) is added and reaction mixture is cooled to 0° C., then methyl 3-amino-3,5-dimethylbenzoate (490 mg, 2.73 mmol) is added followed by N,N-dimethylpyridin-4-amine (15 mg, 122.78 moles) and pyridine (0.66 ml, 8.16 mmoles). The cooling bath is removed and the clear solution is allowed to warm to ambient temperature. After 1.5 hours, the solvent is removed and the reaction mixture is diluted with ethyl acetate and washed with 0.5N HCl, saturated solution of sodium bicarbonate, and brine. The organic layers are combined and dried over anhydrous Na$_2$SO$_4$, filtered, and concentrated under reduced pressure to give the title compound as a light yellow solid (664 mg, 73%). Mass spectrum (m/z): 333.2 (M+1).

Preparation 52

Synthesis of methyl 3-[[6-(4-hydroxy-4-methyl-1-piperidyl)-3-methyl-pyridine-2-carbonyl]amino]-2,4-dimethyl-benzoate

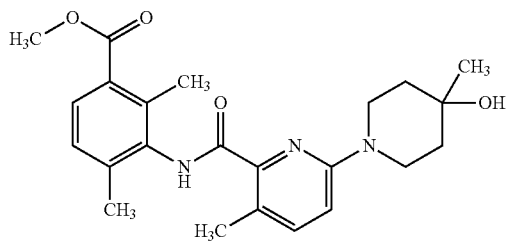 [SMILES: COC(=O)c1ccc(C)c(NC(=O)c2nc(N3CCC(C)(O)CC3)ccc2C)c1C]

Scheme 18, step B. To a solution of methyl 3-[(6-chloro-3-methyl-pyridine-2-carbonyl)amino]-2,4-dimethyl-benzoate (315 mg, 946.55 mmoles), 4-methylpiperidin-4-ol (130 mg, 1.13 mmol) and Cs$_2$CO$_3$ (0.9 g, 2.76 mmol) in 1,4-dioxane (7 ml) is added Pd(OAc)$_2$ (25 mg, 89.93 moles) followed by racemic-2,2'-bis(diphenylphosphino)-1,1'-binaphthyl (56 mg, 89.93 moles). The reaction mixture is purged with nitrogen for 5 minutes and then heated to reflux. After 2 hours, the reaction is cooled to ambient temperature and diluted with ammonium chloride and extracted with EtOAc. The combined organic layers are dried over sodium sulfate, filtered, and concentrated under reduced pressure. The resulting residue is purified by flash chromatography (silica gel) using 0-100% ethyl acetate in hexane to afford the title compound as a brown solid (0.27 g, 69%). Mass spectrum (m/z): 412.2 (M+1).

EXAMPLE 14

Synthesis of 3-[[6-(4-hydroxy-4-methyl-1-piperidyl)-3-methyl-pyridine-2-carbonyl]amino]-2,4-dimethyl-benzoic acid

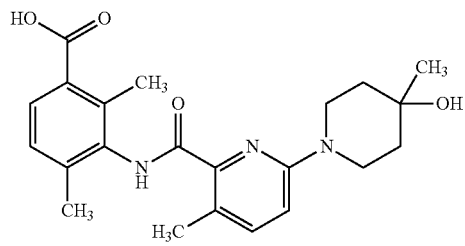 [SMILES: Cc1ccc(N2CCC(C)(O)CC2)nc1C(=O)Nc1c(C)ccc(C(=O)O)c1C]

Scheme 18, step C. A solution of aqueous 2N NaOH (5.00 ml) is added to a stirred solution of methyl 3-[[6-(4-hydroxy-4-methyl-1-piperidyl)-3-methyl-pyridine-2-carbonyl]amino]-2,4-dimethyl-benzoate (0.27 g, 656.13 mmol) in THF:MeOH (10 ml:5 ml). After 1 hour 50° C., the organic solvent is removed under reduced pressure and the residue is diluted with water, acidified to pH 6 with 5N HCl, and extracted with ethyl acetate. The organic layers are combined and concentrated under reduced pressure. The solids are triturated with acetone/acetonitrile and filtered. The filtrate is dried over sodium sulfate, filtered and concentrated under reduced pressure to afford the title compound as an off-white solid (75 mg, 29%). Mass spectrum (m/z): 398.2 (M+1).

Scheme 19

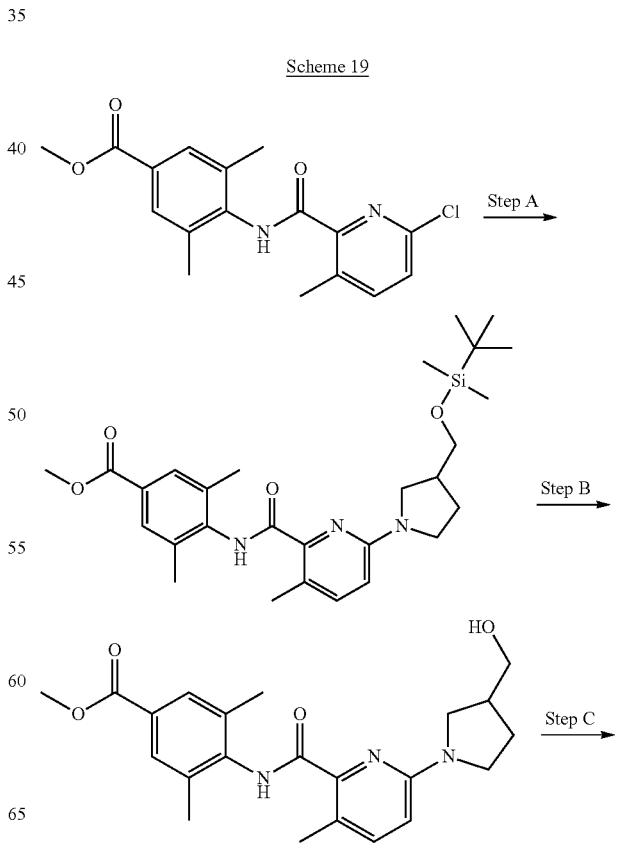

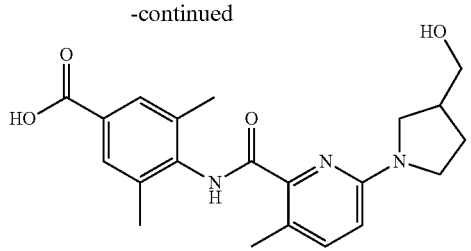

Preparation 53

Synthesis of methyl 4-[[6-[3-[[tert-butyl(dimethyl)silyl]oxymethyl]pyrrolidin-1-yl]-3-methyl-pyridine-2-carbonyl]amino]-3,5-dimethyl-benzoate

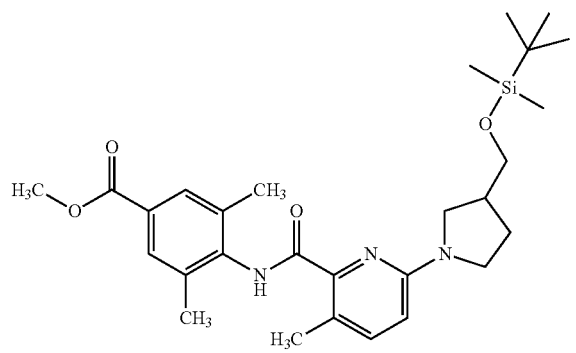 [SMILES: COC(=O)c1cc(C)c(NC(=O)c2nc(N3CCC(CO[Si](C)(C)C(C)(C)C)C3)ccc2C)c(C)c1]

Scheme 19, step A. To a solution of methyl 4-(6-chloro-3-methylpicolinamido)-2,4-dimethylbenzoate (0.4 g, 1.2 mmol, see preparation 2), tert-butyl-dimethyl-(pyrrolidin-3-ylmethoxy)silane (0.775 g, 3.6 mmol) and $Cs_2CO_3$ (1.17 g, 3.6 mmol) in 1,4-dioxane (5 ml) is added $Pd_2(dba)_3$ (0.1 g, 0.12 mmol) followed by S-Phos (0.05 g, 0.12 mmol). The reaction mixture is purged with nitrogen for 5 minutes and then heated at 90° C. After 24 hours, the reaction is cooled to ambient temperature, filtered through Celite™, and washed with EtOAc. The combined filtrates are dried over sodium sulfate, filtered, and concentrated under reduced pressure. The resulting residue is purified by flash chromatography (silica gel) using 10% ethyl acetate in hexanes to afford the title compound as a white semi-solid (1.2 g, crude). Mass spectrum (m/z): 512.2 (M+1).

Preparation 54

Synthesis of methyl 4-[[6-[3-(hydroxymethyl)pyrrolidin-1-yl]-3-methyl-pyridine-2-carbonyl]amino]-3,5-dimethyl-benzoate

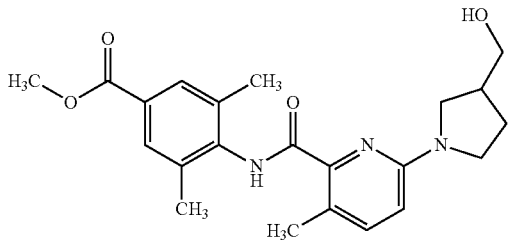 [SMILES: COC(=O)c1cc(C)c(NC(=O)c2nc(N3CCC(CO)C3)ccc2C)c(C)c1]

Scheme 19, step B. To a solution of methyl 4-[[6-[3-[[tert-butyl(dimethyl)silyl]oxymethyl]pyrrolidin-1-yl]-3-methyl-pyridine-2-carbonyl]amino]-3,5-dimethyl-benzoate (1.1 g, 2.15 mmol) in THF (7 ml) is added $Bu_4NF$ 1.0 M in THF (5.00 ml) at 0° C. The reaction mixture is gradually warmed to ambient temperature. After 6 hours, the reaction mixture is diluted with ice-water and extracted with ethyl acetate. The organic layers are combined, dried over sodium sulfate, filtered, and concentrated under reduced pressure. The resulting residue is purified by flash chromatography (silica gel) over a gradient using 0-50% ethyl acetate in hexanes to afford the title compound as an off-white solid (0.36 g, 42%). Mass spectrum (m/z): 398.2 (M+1).

EXAMPLE 15

Synthesis of 4-[[6-[3-(hydroxymethyl)pyrrolidin-1-yl]-3-methyl-pyridine-2-carbonyl]amino]-3,5-dimethyl-benzoic acid

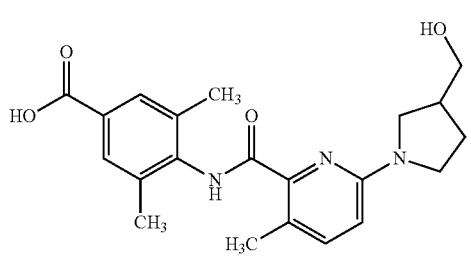 [SMILES: Cc1ccc(N2CCC(CO)C2)nc1C(=O)Nc1c(C)cc(C(=O)O)cc1C]

Scheme 19, step C. A solution of NaOH (0.16 g) in $H_2O$ (1 ml) is added to a stirred solution of methyl 4-[[6-[3-(hydroxymethyl)pyrrolidin-1-yl]-3-methyl-pyridine-2-carbonyl]amino]-3,5-dimethyl-benzoate (0.35 g, 0.88 mmol) in THF:MeOH (5 ml:1 ml). After 8 hours at ambient temperature, the organic solvent is removed under reduced pressure and the residue is diluted with water, acidified to pH 3 with aqueous citric acid solution, and extracted with ethyl acetate (2×10 ml). The organic layers are combined and dried over anhydrous sodium sulfate. The solvent is removed under reduced pressure and the resulting precipitate is triturated with diethyl ether and filtered to afford the title compound as an off-white solid (73 mg, 33.7%). Mass spectrum (m/z): 384.2 (M+1).

Scheme 20

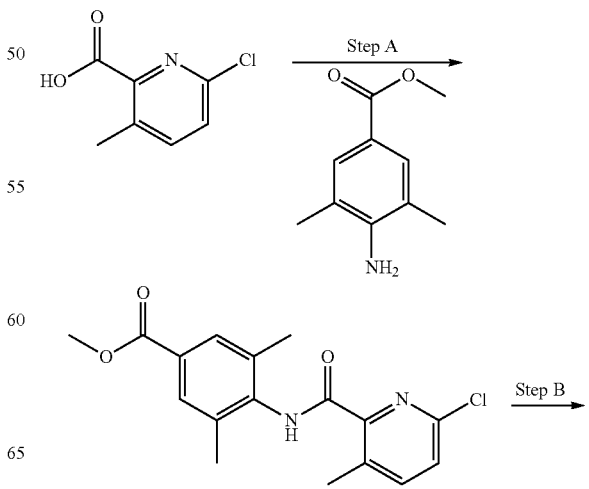

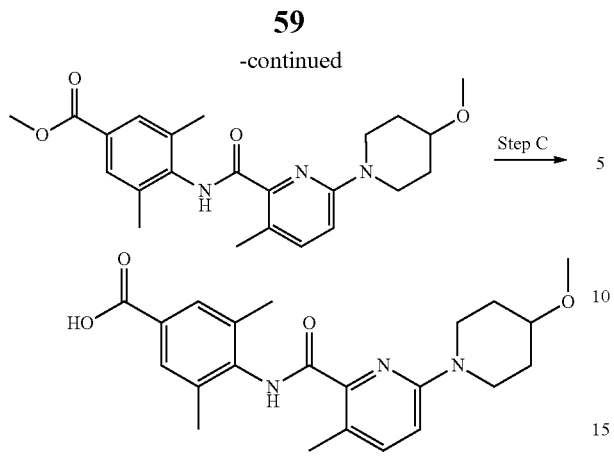

Preparation 55

Synthesis of methyl 4-[(6-chloro-3-methyl-pyridine-2-carbonyl)amino]-3,5-dimethyl-benzoate

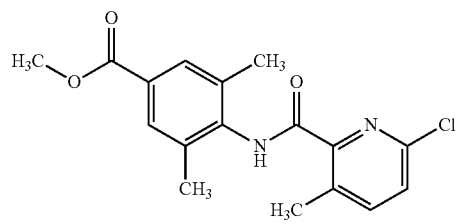 [SMILES: COC(=O)c1cc(C)c(NC(=O)c2nc(Cl)ccc2C)c(C)c1]

Scheme 20, step A. To a solution of 6-chloro-3-methyl-pyridine-2-carboxylic acid (6.00 g, 0.03508 mol) in $CH_2Cl_2$ (50 ml) at 0° C. are added methyl 4-amino-3,5-dimethylbenzoate (5.65 g, 0.03157 mol), and N,N-diisopropylethylamine (15.1 ml, 0.0877 mol). After stirring the reaction mixture for 10 minutes, 1-propanephosphonic acid cyclic anhydride (50% solution in ethyl acetate, 22.32 g, 0.07016 mol) is added via syringe and stirred at 60° C. After 3 hours, the solvent is removed under reduced pressure and the residue is diluted with water and extracted with ethyl acetate. The organic layers are combined and dried over anhydrous $Na_2SO_4$, filtered, and concentrated under reduced pressure. The resulting residue is purified by flash chromatography (silica gel) using a gradient of 0-40% ethyl acetate in hexanes to give the title compound as an off-white solid (8.70 g, 74%). Mass spectrum (m/z): 333.2 (M+1).

Preparation 56

Synthesis of methyl 4-[[6-(4-methoxy-1-piperidyl)-3-methyl-pyridine-2-carbonyl]amino]-3,5-dimethyl-benzoate

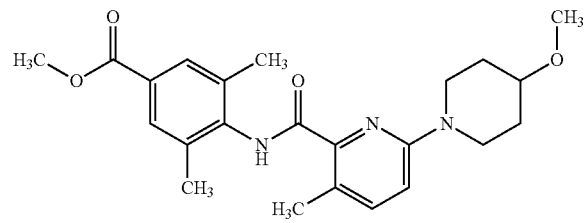

Scheme 20, step B. To a solution of methyl 4-(6-chloro-3-methylpicolinamido)-2,4-dimethylbenzoate (0.30 g, 0.90 mmol), 4-methoxypiperidine (0.178 g, 1.8 mmol) and $Cs_2CO_3$ (0.88 g, 2.7 mmol) in 1,4-dioxane (5 ml) is added $Pd_2(dba)_3$ (0.082 g, 0.09 mmol) followed by S-Phos (0.037 g, 0.09 mmol). The reaction mixture is purged with nitrogen for 5 minutes and then heated at 130° C. After 16 hours, the reaction is cooled to ambient temperature, filtered through Celite™, and washed with EtOAc. The combined filtrates are dried over sodium sulfate, filtered, and concentrated under reduced pressure. The resulting residue is purified by flash chromatography (silica gel) using 20% ethyl acetate in hexane to afford the title compound as a light yellow solid (0.14 g, 34%).

EXAMPLE 16

Synthesis of 4-[[6-(4-methoxy-1-piperidyl)-3-methyl-pyridine-2-carbonyl]amino]-3,5-dimethyl-benzoic acid

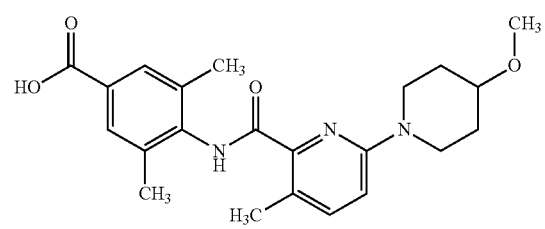 [SMILES: COC1CCN(c2ccc(C)c(C(=O)Nc3c(C)cc(C(=O)O)cc3C)n2)CC1]

Scheme 20, step C. Lithium hydroxide (LiOH.H₂O, 0.026 g, 0.62 mmol) is added to a stirred solution of methyl 4-[[6-(4-methoxy-1-piperidyl)-3-methyl-pyridine-2-carbonyl]amino]-3,5-dimethyl-benzoate (0.129 g, 0.313 mmol) in THF:H₂O:MeOH (0.7 ml:0.3 ml:0.7 ml). After 2 hours at 50° C., the organic solvent is removed under reduced pressure and the residue is diluted with water, acidified to pH 6 with aqueous 1N HCl, and extracted with ethyl acetate (3×20 ml). The organic layers are combined and dried over anhydrous sodium sulfate. The solvent is removed under reduced pressure and the resulting precipitate is triturated with diethyl ether and filtered to afford the title compound as an off-white solid (0.11 g, 88%). Mass spectrum (m/z): 398.2 (M+1).

Scheme 21

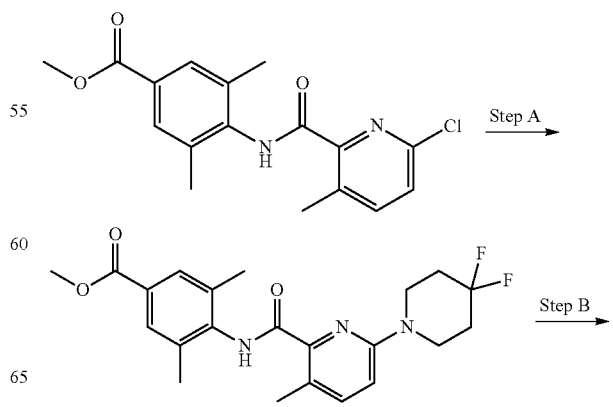

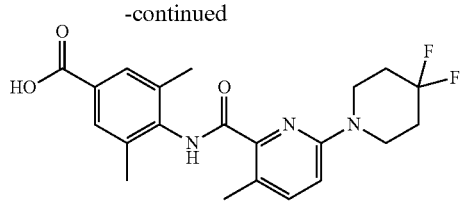

ous 1N HCl, and extracted with ethyl acetate (3×20 ml). The organic layers are combined and dried over anhydrous sodium sulfate. The solvent is removed under reduced pressure and the resulting precipitate is triturated with diethyl ether and filtered to afford the title compound as a white solid (0.166 g, 71%). Mass spectrum (m/z): 404.2 (M+1).

Preparation 57

Synthesis of methyl 4-[[6-(4,4-difluoro-1-piperidyl)-3-methyl-pyridine-2-carbonyl]amino]-3,5-dimethyl-benzoate

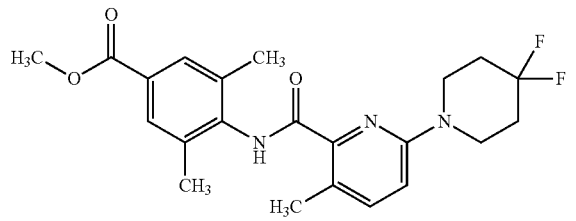 [SMILES: COC(=O)c1cc(C)c(NC(=O)c2nc(N3CCC(F)(F)CC3)ccc2C)c(C)c1]

Scheme 22

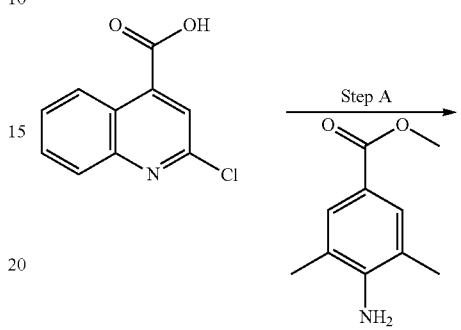

Scheme 21, step A. To a solution of methyl 4-(6-chloro-3-methylpicolinamido)-2,4-dimethylbenzoate (0.30 g, 0.90 mmol, see preparation 43), 4,4-difluoropiperidine (0.283 g, 1.8 mmol) and Cs$_2$CO$_3$ (1.17 g, 3.6 mmol) in 1,4-dioxane (5 ml) is added PdCl$_2$(dppf).CH$_2$Cl$_2$ (0.082 g, 0.0903 mmol) followed by S-Phos (0.037 g, 0.0903 mmol). The reaction mixture is purged with nitrogen for 5 minutes and then heated at 130° C. After 16 hours, the reaction is cooled to ambient temperature, filtered through Celite™ and washed with EtOAc. The combined filtrates are dried over sodium sulfate, filtered, and concentrated under reduced pressure to afford the title compound as a light yellow solid (0.240 g, 63%). Mass spectrum (m/z): 418.2 (M+1).

EXAMPLE 17

Synthesis of 4-[[6-(4,4-difluoro-1-piperidyl)-3-methyl-pyridine-2-carbonyl]amino]-3,5-dimethyl-benzoic acid

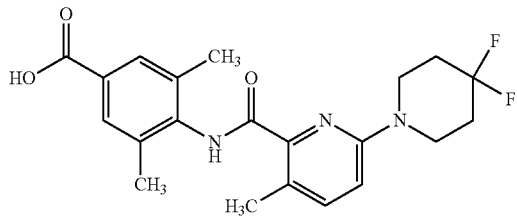 [SMILES: Cc1ccc(N2CCC(F)(F)CC2)nc1C(=O)Nc1c(C)cc(C(=O)O)cc1C]

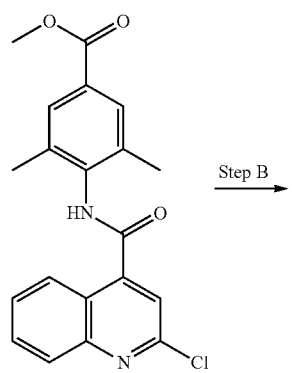

Scheme 21, step B. Lithium hydroxide (LiOH.H$_2$O, 0.048 g, 0.00115 mol) is added to a stirred solution of methyl 4-[[6-(4,4-difluoro-1-piperidyl)-3-methyl-pyridine-2-carbonyl]amino]-3,5-dimethyl-benzoate (0.24 g, 0.575 mmol) in THF:H$_2$O:MeOH (1.5 ml:0.7 ml:1.5 ml). After 3 hours at 50° C., the organic solvent is removed under reduced pressure and the residue is diluted with water, acidified to pH 6 with aque-

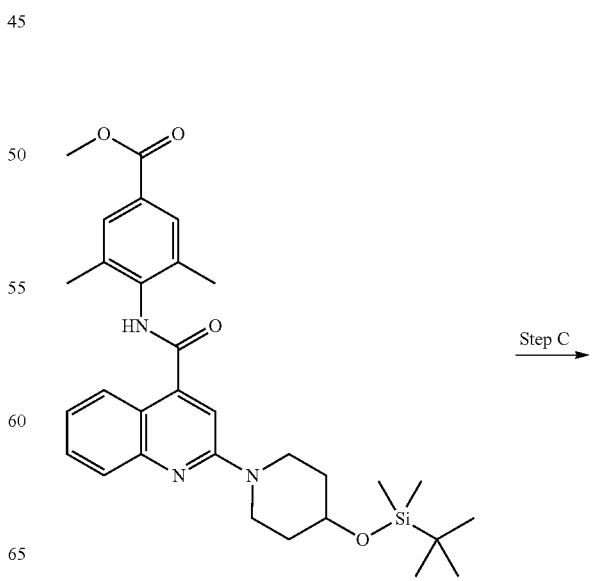

-continued

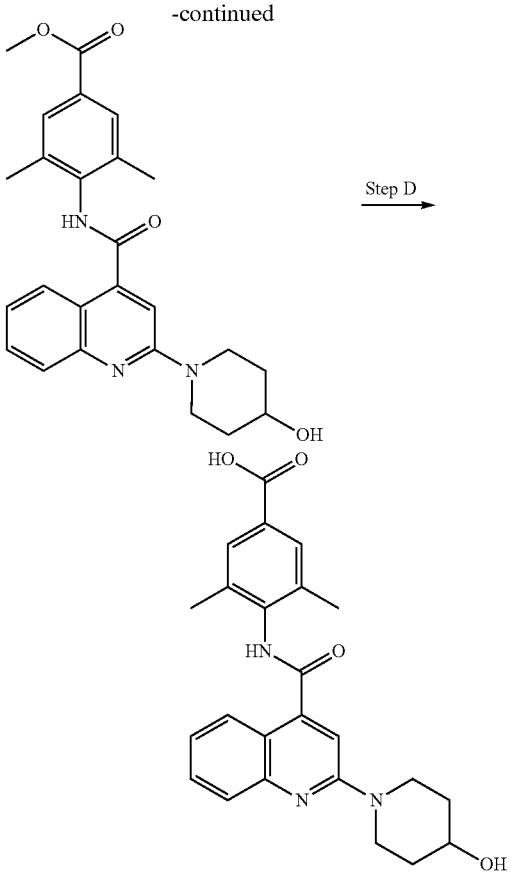

Preparation 58

Synthesis of methyl 4-[(2-chloroquinoline-4-carbonyl)amino]-3,5-dimethyl-benzoate

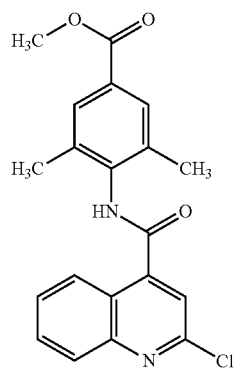 [SMILES: COC(=O)c1cc(C)c(NC(=O)c2cc(Cl)nc3ccccc23)c(C)c1]

Scheme 22, step A. To a solution of 2-chloroquinoline-4-carboxylic acid (5.00 g, 0.0024 mol) in CH$_2$Cl$_2$ (50 mL) at 0° C. are added methyl 4-amino-3,5-dimethylbenzoate (3.88 g, 0.02167 mol, see preparation 12) and N,N-diisopropylethylamine (12.5 ml, 0.07225 mol). After stirring the reaction mixture for 10 minutes, 1-propanephosphonic acid cyclic anhydride (50% solution in ethyl acetate, 31.0 ml, 0.048 mol) is added via syringe and heated at 40° C. After 5 hours, the reaction mixture is diluted with water and extracted with dichloromethane. The organic layers are combined and dried over magnesium sulfate, filtered, and concentrated under reduced pressure. The resulting residue is purified by flash chromatography (silica gel) using a gradient of 0-40% ethyl acetate in hexanes. After purification the solid is triturated with 20% diethyl ether in pentane and dried to give the title compound as a white solid (8.50 g, 96%). Mass spectrum (m/z): 369.1 (M+1).

Preparation 59

Synthesis of methyl 4-[[2-[4-[tert-butyl(dimethyl)silyl]oxy-1-piperidyl]quinoline-4-carbonyl]amino]-3,5-dimethyl-benzoate

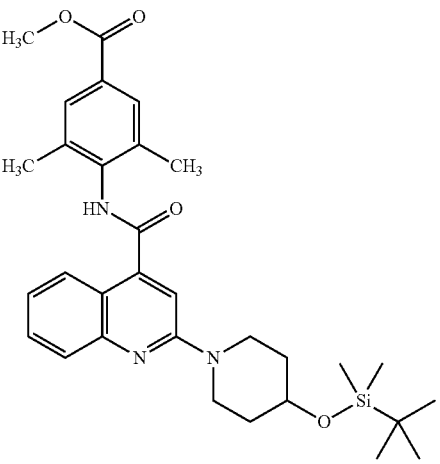 [SMILES: COC(=O)c1cc(C)c(NC(=O)c2cc(N3CCC(O[Si](C)(C)C(C)(C)C)CC3)nc3ccccc23)c(C)c1]

Scheme 22, step B. To a solution of methyl 4-(2-chloroquinoline-4-carboxamido)-3,5-dimethylbenzoate, (0.50 g, 0.00135 mol), tert-butyl-dimethyl-(4-piperidyloxy)silane (0.32 g, 0.0015 mol, see preparation 3) and Cs$_2$CO$_3$ (1.77 g, 0.0054 mol) in 1,4-dioxane (5 ml) is added Pd$_2$(dba)$_3$ (0.124 g, 0.000135 mol) followed by S-Phos (0.060 g, 0.000135 mol). The reaction mixture is purged with nitrogen for 5 minutes and then stirred at 80° C. After 4 hours, the reaction is cooled to ambient temperature, filtered through Celite™, and washed with EtOAc. The organic layers are combined and dried over sodium sulfate, filtered, and concentrated under reduced pressure to afford the title compound (0.21 g, 28%). Mass spectrum (m/z): 548.2 (M+1).

Preparation 60

Synthesis of methyl 4-[[2-(4-hydroxy-1-piperidyl)quinoline-4-carbonyl]amino]-3,5-dimethyl-benzoate

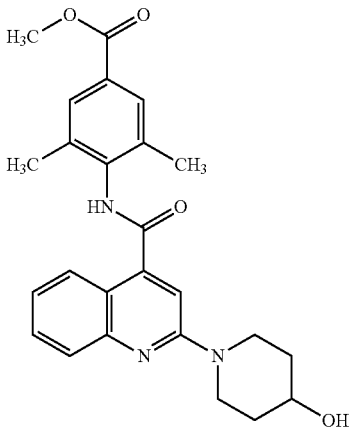 [SMILES: COC(=O)c1cc(C)c(NC(=O)c2cc(N3CCC(O)CC3)nc3ccccc23)c(C)c1]

Scheme 22, step C. To a solution of methyl 4-(2-(4-((tert-butyldimethylsilyl)oxy)piperidin-1-yl)quinoline-4-carboxamido)-3,5-dimethylbenzoate (0.21 g, 0.00038 mol) in THF (4 ml) is added Bu₄NF 1.0 M in THF (4.0 ml) at 0° C. The reaction mixture is gradually warmed to ambient temperature. After 14 hours, the reaction mixture is diluted with ice-water and extracted with ethyl acetate. The organic layers are combined, dried over sodium sulfate, filtered, and concentrated under reduced pressure to give a residue. The residue is purified by flash chromatography (silica gel) over a gradient using 0-40% ethyl acetate in hexanes to afford the title compound as a light yellow solid (0.13 g, 78%). Mass spectrum (m/z): 434.2 (M+1).

EXAMPLE 18

Synthesis of 4-[[2-(4-hydroxy-1-piperidyl)quinoline-4-carbonyl]amino]-3,5-dimethyl-benzoic acid

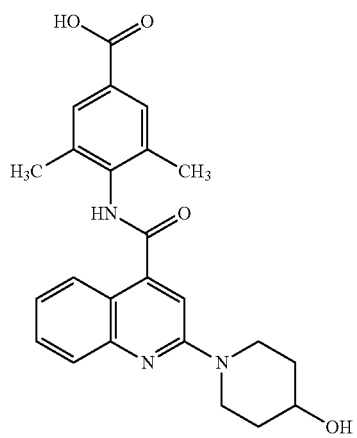 [SMILES: Cc1cc(C(=O)O)cc(C)c1NC(=O)c1cc(N2CCC(O)CC2)nc2ccccc12]

Scheme 22, step D. A solution of aqueous 2N NaOH (2.00 ml) is added to a stirred solution of methyl 4-(2-(4-hydroxypiperidin-1-yl)quinoline-4-carboxamido)-3,5-dimethyl-benzoate (0.13 g, 0.0003 mol) in THF:MeOH (5 ml:2 ml). After 5 h at 50° C., the organic solvent is removed under reduced pressure and the residue is diluted with water acidified to pH 6 with aqueous 1N HCl and extracted with ethyl acetate (2×20 ml). The organic layers are combined and dried over anhydrous sodium sulfate. The solvent is removed under reduced pressure and the resulting precipitate is triturated with pentane and diethyl ether and filtered to afford the title compound as a light yellow solid (0.05 g, 40%). Mass spectrum (m/z): 420.2 (M+1).

Scheme 23

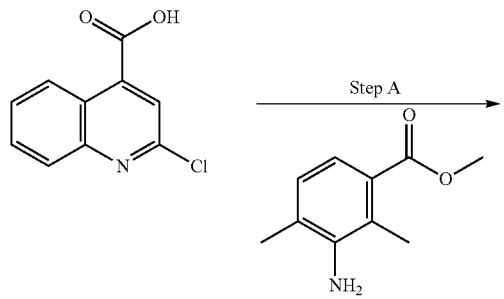

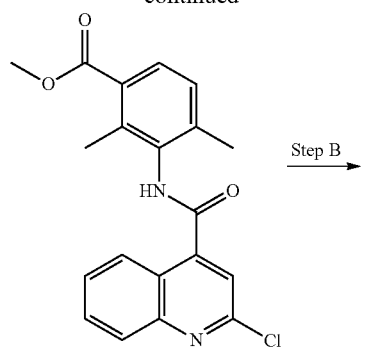

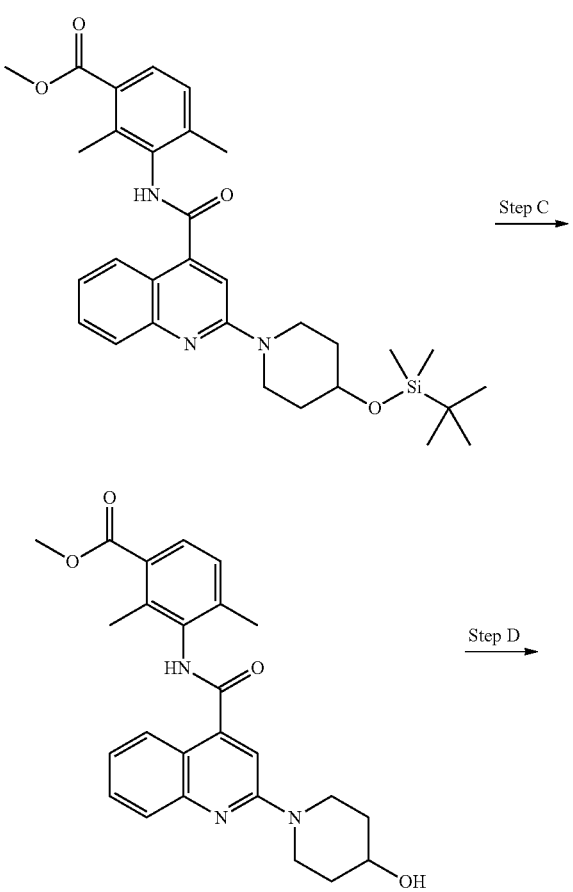

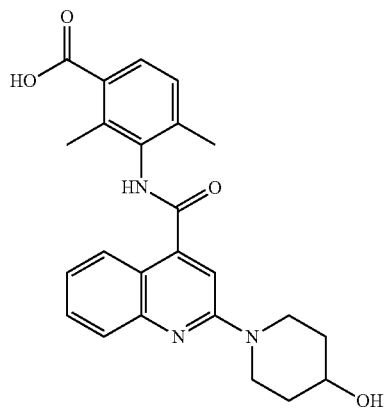 [SMILES: Cc1ccc(C(=O)O)c(C)c1NC(=O)c1cc(N2CCC(O)CC2)nc2ccccc12]

Preparation 61

Synthesis of methyl 3-[(2-chloroquinoline-4-carbonyl)amino]-2,4-dimethyl-benzoate

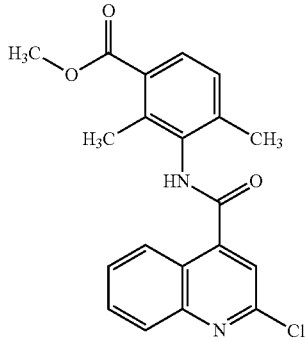 [SMILES: COC(=O)c1ccc(C)c(NC(=O)c2cc(Cl)nc3ccccc23)c1C]

Scheme 23, step A. To a solution of 2-chloroquinoline-4-carboxylic acid (0.40 g, 0.0019 mol) in $CH_2Cl_2$ (8 mL) at 0° C. are added methyl 3-amino-2,4-dimethylbenzoate (0.31 g, 0.0017 mol, see preparation 10) and triethylamine (0.80 ml, 0.0058 mol). After stirring the reaction mixture for 10 minutes, 1-propanephosphonic acid cyclic anhydride (50% solution in ethyl acetate, 2.45 ml, 0.0038 mol) is added via syringe and stirred at room temperature. After 16 hours, the reaction is diluted with water and extracted twice with dichloromethane. The organic layers are combined and dried over magnesium sulfate, filtered, and concentrated under reduced pressure. The resulting residue is triturated with 20% diethyl ether in pentane and filtered to give the title compound as an off-white solid (0.55 g, 77%). Mass spectrum (m/z): 369.1 (M+1).

Preparation 62

Synthesis of methyl 3-[[2-[4-[tert-butyl(dimethyl)silyl]oxy-1-piperidyl]quinoline-4-carbonyl]amino]-2,4-dimethyl-benzoate

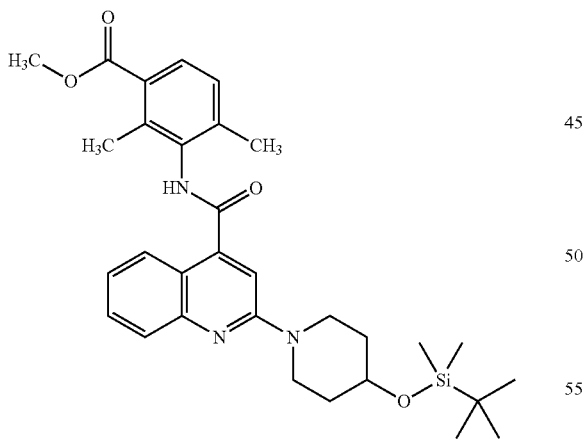

Scheme 23, step B. To a solution of methyl 3-(2-chloroquinoline-4-carboxamido)-2,4-dimethylbenzoate (0.54 g, 0.00146 mol), tert-butyl-dimethyl-(4-piperidyloxy)silane (0.63 g, 0.00293 mol, see preparation 3) and $Cs_2CO_3$ (1.43 g, 0.0044 mol) in 1,4-dioxane (8 ml) is added $Pd_2(dba)_3$ (0.134 g, 0.000146 mol) followed by S-Phos (0.060 g, 0.000146 mol). The reaction mixture is purged with nitrogen for 5 minutes and then stirred at 80° C. After 16 hours, the reaction is cooled to ambient temperature, filtered through Celite™, and washed with EtOAc. The organic layers are combined and dried over sodium sulfate, filtered, and concentrated under reduced pressure to afford the title compound as a black semi-solid (1.31 g, 60%, crude). Mass spectrum (m/z): 548.2 (M+1).

Preparation 63

Synthesis of methyl 3-[[2-(4-hydroxy-1-piperidyl)quinoline-4-carbonyl]amino]-2,4-dimethyl-benzoate

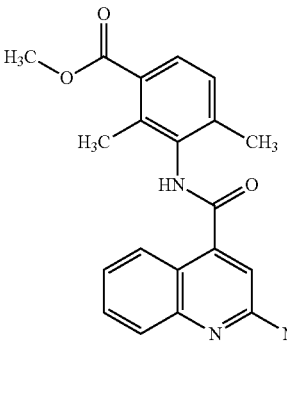

Scheme 23, step C. To a solution of methyl 3-(2-(4-((tert-butyldimethylsilyl)oxy)piperidin-1-yl)quinoline-4-carboxamido)-2,4-dimethylbenzoate (1.30 g, 0.00087 mol) in THF (2.0 ml) is added $Bu_4NF$ 1.0 M in THF (10.0 ml) at 0° C. The reaction mixture is gradually warmed to ambient temperature. After 14 hours, the reaction mixture is diluted with ice-water and extracted with ethyl acetate. The organic layers are combined, dried over sodium sulfate, filtered, and concentrated under reduced pressure to give a residue. The residue is purified by flash chromatography (silica gel) with ethyl acetate in hexanes to afford the title compound as a yellow solid (0.10 g, 27%). Mass spectrum (m/z): 434.3 (M+1).

EXAMPLE 19

Synthesis of 3-[[2-(4-hydroxy-1-piperidyl)quinoline-4-carbonyl]amino]-2,4-dimethyl-benzoic acid

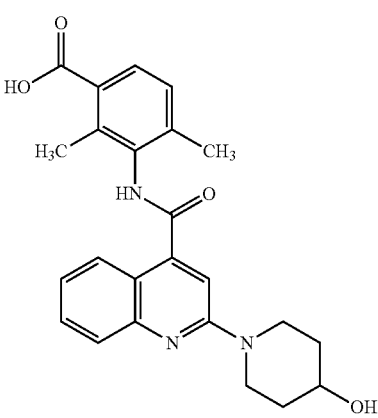 [SMILES: Cc1ccc(C(=O)O)c(C)c1NC(=O)c1cc(N2CCC(O)CC2)nc2ccccc12]

Scheme 23, step D. A solution of aqueous 2N NaOH (2.00 ml) is added to a stirred solution of methyl 3-(2-(4-hydroxypiperidin-1-yl)quinoline-4-carboxamido)-2,4-dimethylbenzoate (0.10 g, 0.00023 mol) in THF:MeOH (4 ml:2 ml). After 5 h at 50° C., the organic solvent is removed under reduced pressure and the residue is diluted with water, acidified to pH 6 with aqueous 1N HCl, and extracted with ethyl acetate (2×20 ml). The organic layers are combined and dried over anhydrous sodium sulfate. The solvent is removed under reduced pressure and the resulting precipitate is triturated with pentane and diethyl ether and filtered to afford the title compound as a light yellow solid (0.03 g, 31%). Mass spectrum (m/z): 420.2 (M+1).

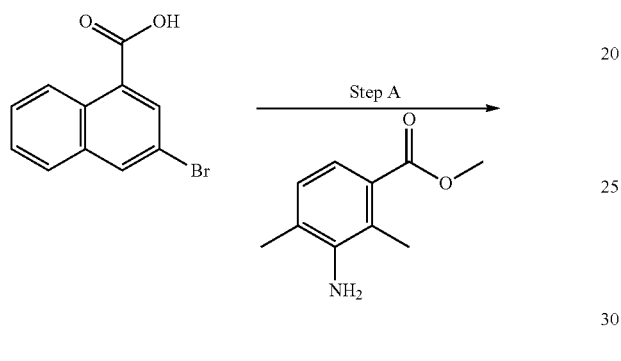

Scheme 24

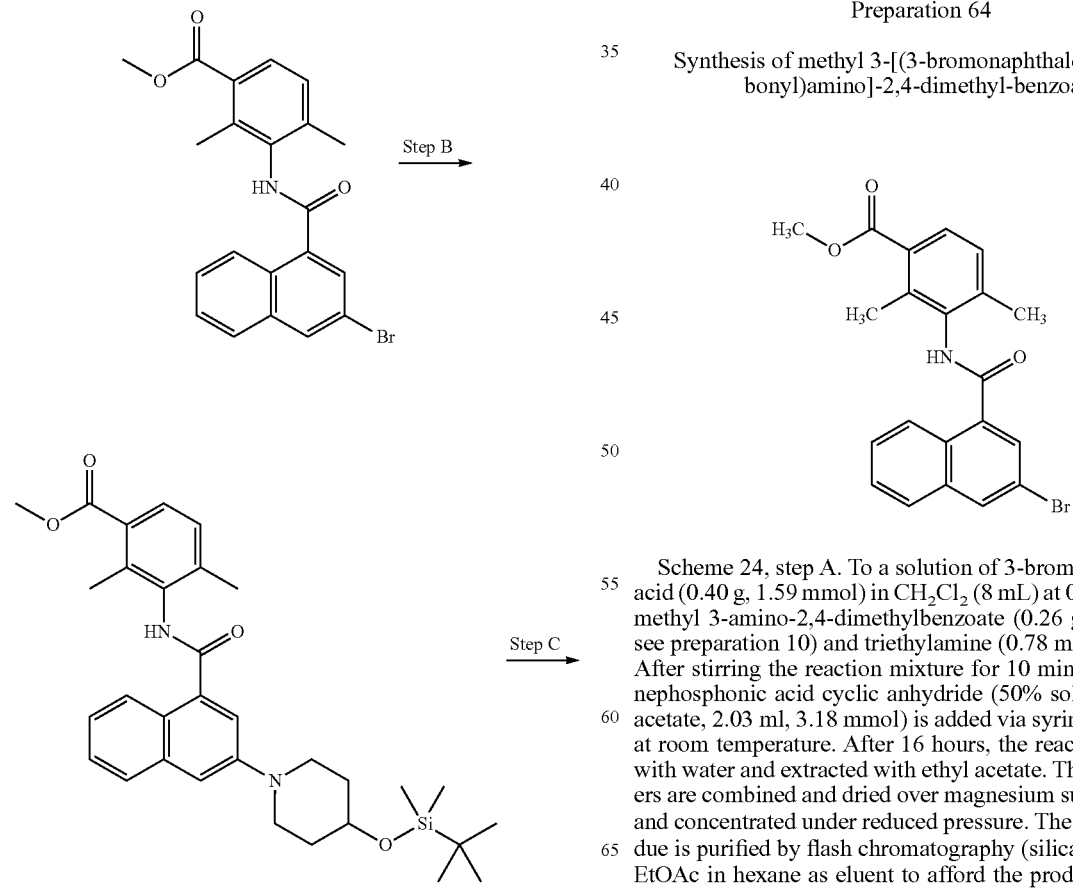

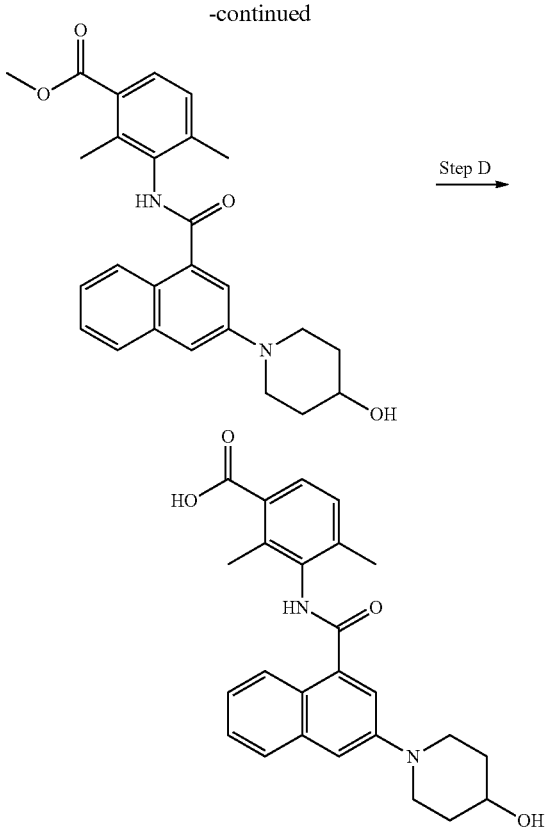

Preparation 64

Synthesis of methyl 3-[(3-bromonaphthalene-1-carbonyl)amino]-2,4-dimethyl-benzoate Scheme 24, step A. To a solution of 3-bromo-1-naphthoic acid (0.40 g, 1.59 mmol) in $CH_2Cl_2$ (8 mL) at 0° C. are added methyl 3-amino-2,4-dimethylbenzoate (0.26 g, 1.43 mmol, see preparation 10) and triethylamine (0.78 ml, 5.38 mmol). After stirring the reaction mixture for 10 minutes, 1-propanephosphonic acid cyclic anhydride (50% solution in ethyl acetate, 2.03 ml, 3.18 mmol) is added via syringe and stirred at room temperature. After 16 hours, the reaction is diluted with water and extracted with ethyl acetate. The organic layers are combined and dried over magnesium sulfate, filtered, and concentrated under reduced pressure. The resulting residue is purified by flash chromatography (silica gel) with 5% EtOAc in hexane as eluent to afford the product as a white solid (0.52 g, 79%). Mass spectrum (m/z): 412.3 (M+1).

Preparation 65

Synthesis of methyl 3-[[3-[4-[tert-butyl(dimethyl)silyl]oxy-1-piperidyl]naphthalene-1-carbonyl]amino]-2,4-dimethyl-benzoate

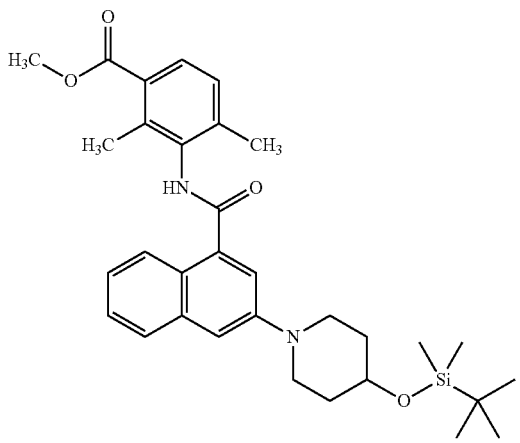 [SMILES: COC(=O)c1ccc(C)c(NC(=O)c2cc(N3CCC(O[Si](C)(C)C(C)(C)C)CC3)cc3ccccc23)c1C]

Scheme 24, step B. To a solution of methyl 3-(3-bromo-1-naphthamido)-2,4-dimethylbenzoate (0.48 g, 0.0011 mol), tert-butyl-dimethyl-(4-piperidyloxy)silane (0.75 g, 0.0034 mol, see preparation 3) and Cs$_2$CO$_3$ (1.00 g, 0.0033 mol) in 1,4-dioxane (8 ml) is added Pd$_2$(dba)$_3$ (0.10 g, 0.00011 mol) followed by S-Phos (0.045 g, 0.00011 mol). The reaction mixture is purged with nitrogen for 5 minutes and then stirred at 80° C.

After 16 hours, the reaction is cooled to ambient temperature, filtered through Celite™ and washed with EtOAc. The organic layers are combined and dried over sodium sulfate, filtered, and concentrated under reduced pressure to afford the title compound as a black semi-solid (0.52 g, crude). Mass spectrum (m/z): 547.5 (M+1).

Preparation 66

Synthesis of methyl 3-[[3-(4-hydroxy-1-piperidyl)naphthalene-1-carbonyl]amino]-2,4-dimethyl-benzoate

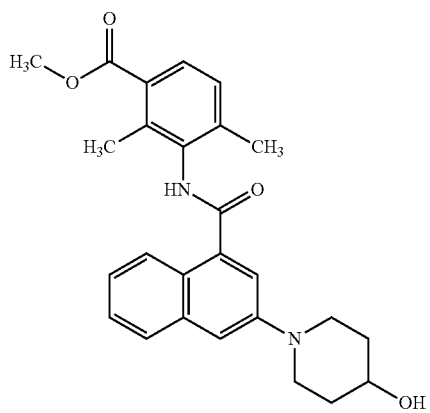 [SMILES: COC(=O)c1ccc(C)c(NC(=O)c2cc(N3CCC(O)CC3)cc3ccccc23)c1C]

Scheme 24, step C. To a solution of methyl 3-[[3-[4-[tert-butyl(dimethyl)silyl]oxy-1-piperidyl]naphthalene-1-carbonyl]amino]-2,4-dimethyl-benzoate (0.30 g, 0.54 mmol) in THF (8.0 ml) is added Bu$_4$NF 1.0 M in THF (0.35 g, 1.60 mmol) at 0° C. The reaction mixture is gradually warmed to ambient temperature. After 14 hours, the reaction mixture is diluted with ice-water and extracted with ethyl acetate. The organic layers are combined, dried over sodium sulfate, filtered, and concentrated under reduced pressure to give a residue. The residue is purified by flash chromatography (silica gel) with ethyl acetate in hexanes to afford the title compound as a white solid (0.10 g, 55%). Mass spectrum (m/z): 433.0 (M+1).

EXAMPLE 20

Synthesis of 3-[[3-(4-hydroxy-1-piperidyl)naphthalene-1-carbonyl]amino]-2,4-dimethyl-benzoic acid

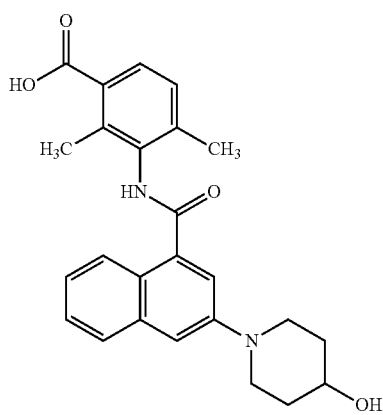

Scheme 24, step D. A solution of aqueous 2N NaOH (3.00 ml) is added to a stirred solution of methyl 3-(3-(4-hydroxypiperidin-1-yl)-1-naphthamido)-2,4-dimethylbenzoate (0.10 g, 0.23 mmol) in THF:MeOH (3 ml:1 ml). After 12 hours at room temperature, the organic solvent is removed under reduced pressure and the residue is diluted with water, acidified to pH 4 with aqueous 1N HCl and extracted with dichloromethane (2×20 ml). The organic layers are combined and dried over anhydrous sodium sulfate. The solvent is removed under reduced pressure and the resulting precipitate is triturated with diethyl ether and filtered to afford the title compound as a white solid (0.028 g, 29%). Mass spectrum (m/z): 419.2 (M+1).

Scheme 25

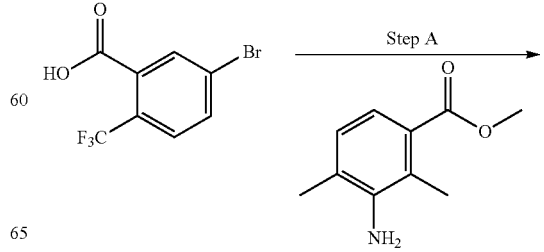

-continued

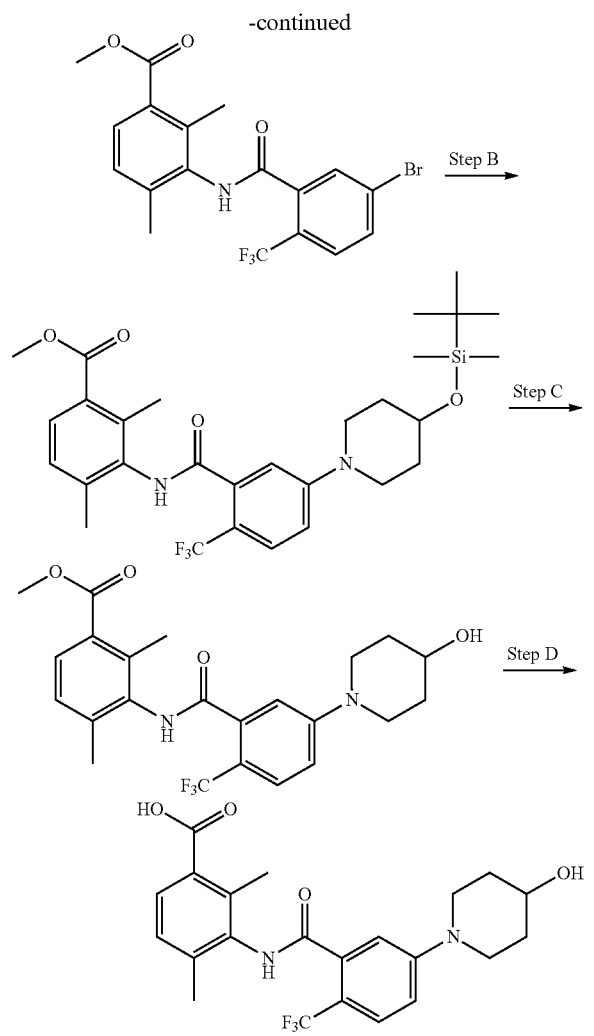

Preparation 67

Synthesis of methyl 3-[[5-bromo-2-(trifluoromethyl)benzoyl]amino]-2,4-dimethyl-benzoate

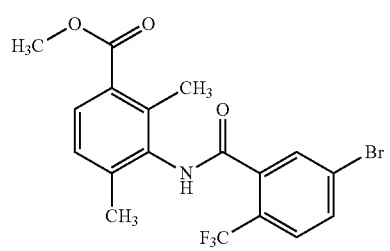

Scheme 25, step A. To a solution of 5-bromo-2-(trifluoromethyl)benzoic acid (1.0 g, 3.53 mmol) in $CH_2Cl_2$ (6 ml) at room temperature are added methyl 3-amino-3,5-dimethyl-benzoate (0.44 g, 2.47 mmol, see preparation 12) and triethylamine (1.0 ml, 7.06 mmol). After stirring the reaction mixture for 10 minutes, 1-propanephosphonic acid cyclic anhydride (50% solution in ethyl acetate, 5.6 ml, 8.83 mmol) is added via syringe. After 14 hours at ambient temperature, the reaction mixture is diluted with $CH_2Cl_2$, washed with water and brine. The organic layers are combined and dried over anhydrous $Na_2SO_4$, filtered, and concentrated under reduced pressure. The resulting residue is purified by flash chromatography (silica gel) using 20% ethyl acetate in hexanes to give the title compound as a white solid (0.6 g, 39%).

Preparation 68

Synthesis of methyl 3-[[5-[4-[tert-butyl(dimethyl)silyl]oxy-1-piperidyl]-2-(trifluoromethyl)benzoyl]amino]-2,4-dimethyl-benzoate

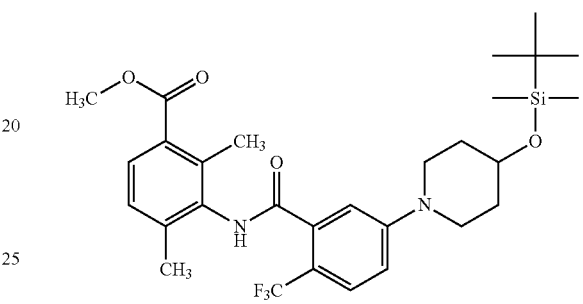

Scheme 25, step B. To a solution of methyl 3-[[5-bromo-2-(trifluoromethyl)benzoyl]amino]-2,4-dimethyl-benzoate (0.20 g, 0.46 mmol), tert-butyl-dimethyl-(3-piperidylmethoxy)silane (0.11 g, 0.50 mmol, see preparation 3) and $Cs_2CO_3$ (0.45 g, 1.39 mmol) in 1,4-dioxane (15 ml) is added $Pd_2(dba)_3$ (43 mg, 0.046 mmol) followed by S-Phos (19.3 mg, 0.046m mol). The reaction mixture is purged with nitrogen for 5 minutes and then heated at 110° C. After 12 hours, the reaction is cooled to ambient temperature, filtered through Celite™, and washed with EtOAc. The combined filtrates are dried over sodium sulfate, filtered, and concentrated under reduced pressure. The resulting residue is purified by flash chromatography (silica gel) using 30% ethyl acetate in hexane to afford the title compound as a brown semi-solid (180 mg, 68%). Mass spectrum (m/z): 565.2 (M+1).

Preparation 69

Synthesis of methyl 3-[[5-(4-hydroxy-1-piperidyl)-2-(trifluoromethyl)benzoyl]amino]-2,4-dimethyl-benzoate

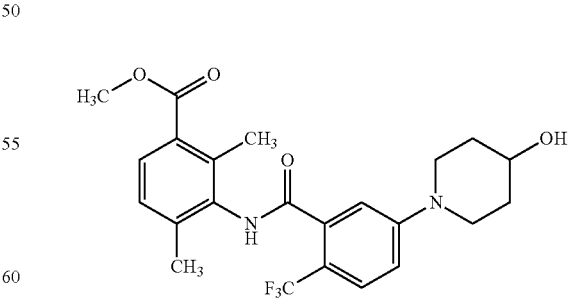

Scheme 25, step C. To a solution of methyl 3-[[5-[4-[tert-butyl(dimethyl)silyl]oxy-1-piperidyl]-2(trifluoromethyl)benzoyl]amino]-2,4-dimethyl-benzoate (180 mg, 0.32 mmol) in THF (10.0 ml) is added $Bu_4NF$ 1.0 M in THF (2.0 ml) at 0° C. The reaction mixture is gradually warmed to ambient temperature. After 8 hours, the reaction mixture is diluted with ice-water and extracted with ethyl acetate. The organic layers are combined, dried over sodium sulfate, filtered, and concentrated under reduced pressure to give a residue. The residue is purified by flash chromatography (neutral alumina) over a gradient using 100% ethyl acetate in hexane to afford the title compound as a white solid (0.11 g, 76%). Mass spectrum (m/z): 451.2 (M+1).

EXAMPLE 21

Synthesis of 3-[[5-(4-hydroxy-1-piperidyl)-2-(trifluoromethyl)benzoyl]amino]-2,4-dimethyl-benzoic acid

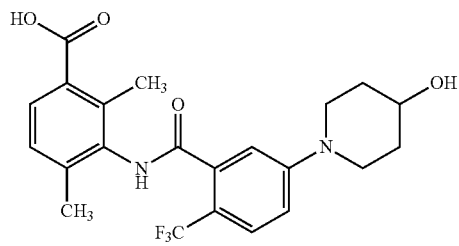 [SMILES: Cc1ccc(C(=O)O)c(C)c1NC(=O)c1cc(N2CCC(O)CC2)ccc1C(F)(F)F]

Scheme 25, step D. A solution of aqueous 2N NaOH (2 ml) is added to a stirred solution of methyl 3-[[6-[3-(hydroxymethyl)-1-piperidyl]-3-methyl-pyridine-2-carbonyl]amino]-2,4-dimethyl-benzoate (0.11 g, 0.24 mmol) in THF (8 ml). After 12 hours at ambient temperature, the organic solvent is removed under reduced pressure and the residue is diluted with water, acidified to pH 4 with 1N HCl, and extracted twice with dichloromethane. The organic layers are combined and dried over anhydrous sodium sulfate. The solvent is removed under reduced pressure and the resulting precipitate is triturated with pentane and diethyl ether and filtered to afford the title compound as an off-white solid (95 mg, 89%). Mass spectrum (m/z): 437.2 (M+1).

Scheme 26

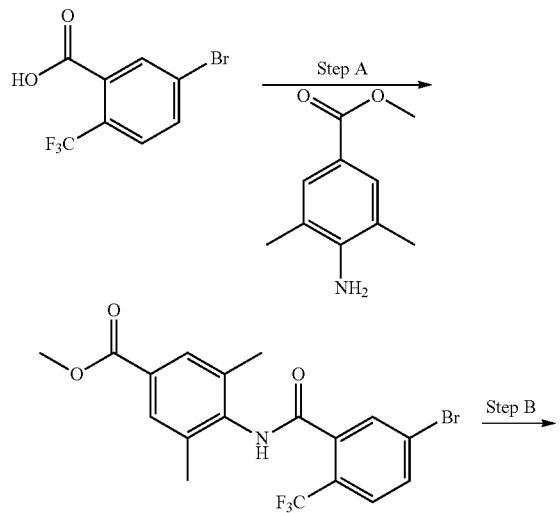

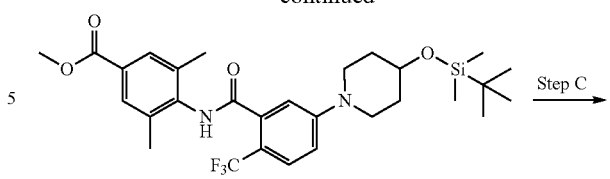

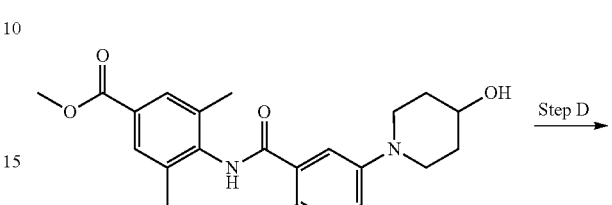

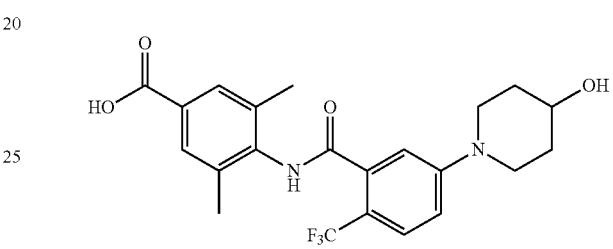

Preparation 70

Synthesis of methyl 4-[[5-bromo-2-(trifluoromethyl)benzoyl]amino]-3,5-dimethyl-benzoate

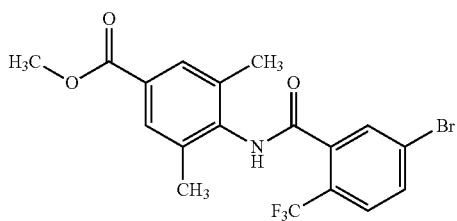 [SMILES: COC(=O)c1cc(C)c(NC(=O)c2cc(Br)ccc2C(F)(F)F)c(C)c1]

Scheme 26, step A. To a solution of 5-bromo-2-(trifluoromethyl)benzoic acid (1.00 g, 0.00371 mol) in CH$_2$Cl$_2$ (15 mL) at room temperature are added methyl 4-amino-3,5-dimethylbenzoate (0.46 g, 0.00260 mol, see preparation 12) and triethylamine (1.10 ml, 0.00743 mol). After stirring the reaction mixture for 10 minutes, 1-propanephosphonic acid cyclic anhydride (50% solution in ethyl acetate, 6.00 ml, 0.00929 mol) is added via syringe and stirred at room temperature. After 14 hours, the reaction mixture is diluted with water and extracted with dichloromethane. The organic layers are combined and dried over magnesium sulfate, filtered, and concentrated under reduced pressure. The resulting residue is purified by flash chromatography (silica gel) with 10-15% EtOAc to give the title compound as an off-white solid (0.45 g, 27.67%). Mass spectrum (m/z): 430.0 (M+1).

Preparation 71

Synthesis of methyl 4-[[5-[4-[tert-butyl(dimethyl)silyl]oxy-1-piperidyl]-2-(trifluoromethyl)benzoyl]amino]-3,5-dimethyl-benzoate

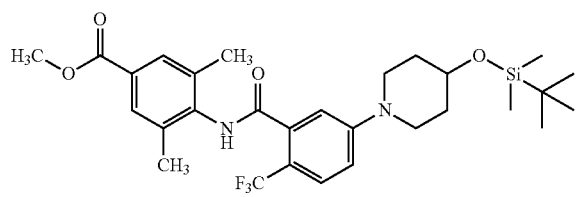 [SMILES: COC(=O)c1cc(C)c(NC(=O)c2cc(N3CCC(O[Si](C)(C)C(C)(C)C)CC3)ccc2C(F)(F)F)c(C)c1]

Scheme 26, step B. To a solution of methyl 4-[[5-bromo-2-(trifluoromethyl)benzoyl]amino]-3,5-dimethyl-benzoate (0.10 g, 232.44 μmol), tert-butyl-dimethyl-(4-piperidyloxy)silane (55.08 mg, 255.68 μmol, see preparation 3) and $Cs_2CO_3$ (227.2 mg, 697.32 μmol) in 1,4-dioxane (2.5 ml) is added $Pd_2(dba)_3$ (21.28 mg, 23.24 μmol) followed by 2-dicyclohexylphosphino-2',6'-dimethoxybiphenyl (S-Phos) (9.54 mg, 23.24 μmol). The reaction mixture is purged with nitrogen for 5 minutes and then heated at 120° C. After 8 hours, the reaction is cooled to ambient temperature, filtered through Celite™, and washed with EtOAc. The combined filtrates are dried over sodium sulfate, filtered, and concentrated under reduced pressure and purified by flash chromatography (neutral alumina) using of 15%-85% ethyl acetate in hexanes as eluent to afford the title compound as a pale yellow oil (0.10 g, 80%). Mass spectrum (m/z): 565.4 (M+1).

Preparation 72

Synthesis of methyl 4-[[5-(4-hydroxy-1-piperidyl)-2-(trifluoromethyl)benzoyl]amino]-3,5-dimethyl-benzoate

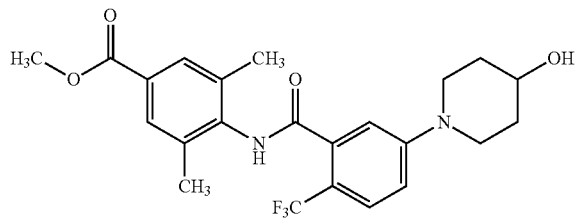 [SMILES: COC(=O)c1cc(C)c(NC(=O)c2cc(N3CCC(O)CC3)ccc2C(F)(F)F)c(C)c1]

Scheme 26, step C. To a solution of methyl 4-[[5-[4-[tert-butyl(dimethyl)silyl]oxy-1-piperidyl]-2-(trifluoromethyl)benzoyl]amino]-3,5-dimethyl-benzoate (0.10 g, 177.08 moles) in THF (4 ml) is added $Bu_4NF$ 1.0 M in THF (1.0 ml) at 0° C. The reaction mixture is gradually warmed to ambient temperature. After 6 hours, the reaction mixture is diluted with ice-water and extracted with ethyl acetate. The organic layers are combined, dried over sodium sulfate, filtered, and concentrated under reduced pressure to give a residue. The residue is purified by flash chromatography (silica gel) over a gradient using 40-60% ethyl acetate in hexanes to afford the title compound as a light yellow solid (0.06 g, 81.5%). Mass spectrum (m/z): 451.2 (M+1).

EXAMPLE 22

Synthesis of 4-[[5-(4-hydroxy-1-piperidyl)-2-(trifluoromethyl)benzoyl]amino]-3,5-dimethyl-benzoic acid

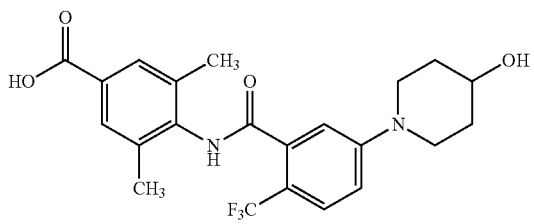 [SMILES: Cc1cc(C(=O)O)cc(C)c1NC(=O)c1cc(N2CCC(O)CC2)ccc1C(F)(F)F]

Scheme 26, step D. A solution of aqueous 2N NaOH (1.5.00 ml) is added to a stirred solution of methyl 4-[[5-[4-[tert-butyl(dimethyl)silyl]oxy-1-piperidyl]-2-(trifluoromethyl)benzoyl]amino]-3,5-dimethyl-benzoate (60.0 mg, 133.20 mmoles) in THF:MeOH (5 ml:0.5 ml). After 12 h at ambient temperature, the organic solvent is removed under reduced pressure and the residue is diluted with water, acidified to pH4 with aqueous citric acid, and extracted with ethyl acetate (2×20 ml). The organic layers are combined and dried over anhydrous sodium sulfate. The solvent is removed under reduced pressure and the resulting precipitate is triturated with pentane and diethyl ether and filtered to afford the title compound as an off-white solid (0.04 g, 60%). Mass spectrum (m/z): 437.2 (M+1).

In Vitro Binding to Human EP1, EP2, EP3 and EP4 hEP1 and hEP4 membranes are prepared from recombinant HEK293 cells stably expressing human EP1 (Genbank accession number AY275470) or EP4 (Genbank accession number AY429109) receptors. hEP2 and hEP3 membranes are prepared from HEK293 cells transiently transfected with EP2 (Genbank accession number AY275471) or EP3 (isoform VI: Genbank accession number AY429108) receptor plasmids. Frozen cell pellets are homogenized in homogenization buffer using a Teflon/glass homogenizer. Membrane protein is aliquoted and quick frozen on dry ice prior to storage at −80° C. Homogenization buffer contained 10 mM Tris-HCl, pH 7.4, 250 mM sucrose, 1 mM EDTA, 0.3 mM indomethacin and plus Complete™, with EDTA, obtained from Roche Molecular Biochemicals (Catalog Number 1 697 498).

Kd values for [3H]-$PGE_2$ binding to each receptor are determined by saturation binding studies or homologous competition. Compounds are tested in a 96-well format using a three-fold dilution series to generate a 10-point curve. Diluted compound is incubated with 20 μg/well EP1, 10 μg/well EP2, 1 ug/well EP3 or 10 to 20 μg/well EP4 membrane for 90 minutes at 25° C. in the presence of 0.3 to 0.5 nM [$^3$H]-$PGE_2$ (PerkinElmer, 118 to 180 Ci/mmol). The binding reaction is performed in 200 μL MES buffer (10 mM MES pH 6.0 with KOH, 10 mM $MgCl_2$ and 1 mM EDTA) using 0.5 mL polystyrene 96-well deep-well plates. Nonspecific binding is calculated by comparing binding in the presence and absence of 2 μM of $PGE_2$. The membranes are harvested by filtration (TomTek harvester), washed 4 times with cold buffer (10 mM MES pH 6.0 with KOH, 10 mM $MgCl_2$), dried in a 60° C. oven, and the radioactivity is quantified as counts per minute (CPM) using a TopCount detector. Percent specific binding is calculated as the percent of the binding in the absence of any inhibitor, corrected for binding in the presence of 2 uM of $PGE_2$. Data are analyzed using a 4-parameter nonlinear logistic equation (ABase Equation 205) as shown: $y=(A+((B-A)/(1+((C/x)^D))))$ where, y=% specific inhibition, A=bottom of the curve; B=top of the curve; C=relative $IC_{50}$=concentration causing 50% inhibition based on the range of the data from top to bottom; D=Hill, Slope=slope of the curve. $K_i$ conversion from $IC_{50}$ Values ($K_i=IC_{50}/(1+[L]/K_d)$ where [L] is the ligand concentration). The compounds of Examples 1-22 herein are tested essentially as described above and exhibit a $K_i$ value for hEP4 of lower than about 2 µM.

TABLE 2

In vitro binding of Example 1 to human EP1, EP2, EP3 and EP4

| Test Compound | hEP1, $K_i$ (nM) | hEP2, $K_i$ (nM) | hEP3, $K_i$ (nM) | hEP4, $K_i$ (nM) |
|---|---|---|---|---|
| Example 1 | >17500 (n = 1) | >18900 (n = 1) | >14000 (n = 1) | 76 ± 47 (n = 7) |

Following the procedures essentially as described above, the data in table 2 demonstrate that the compound of Example 1 binds to hEP4 at low nanomolar concentrations. The data in table 2 also demonstrate the compound of Example 1 binds to hEP4 more strongly than to hEP1, hEP2, and hEP3 indicating selectivity for the hEP4 receptor.

In Vitro Human EP4 Functional Antagonist Activity

Assays are conducted in recombinant HEK293 cells stably expressing human EP4 receptor. The cell lines are maintained by culturing in DMEM with high glucose and pyridoxine hydrochloride (Invitrogen) supplemented with 10% fetal bovine serum (FBS), 1 mM sodium pyruvate, 10 mM HEPES, 500 µg/ml geneticin and 2 mM L-glutamine. Confluent cultures are grown at 37° C. in an atmosphere containing 5% $CO_2$. Cells are harvested using 2.5% Trypsin-EDTA, suspended in freeze media (FBS with 6% DMSO) at $10^7$ cells/mL and aliquots are stored in liquid nitrogen. Just before assay, cells are thawed in DMEM, centrifuged, and resuspended in cAMP buffer.

The inhibition of $PGE_2$-stimulated cAMP production by EP4 antagonists is measured using HTRF; (Cisbio catalog #62AM4PEB). An aliquot equivalent to 4000 cells is incubated with 50 µL cAMP assay buffer containing $EC_{80}$ of $PGE_2$ (0.188 nM $PGE_2$ from Sigma, catalog #P5640-10 mg) and antagonists at room temperature for 20 minutes. cAMP assay buffer contains 500 mL HBSS (Hank's Balanced Salt Solution), 0.1% BSA, 20 mM HEPES and 200 µM IBMX (Sigma I5879). CJ-042794 (4-{(1S)-1-[({5-chloro-2-[(4-fluorophenyl)oxy]phenyl}carbonyl)amino]ethyl}benzoic acid) serves as a positive control. To measure the cAMP levels, cAMP-d2 conjugate and anti cAMP-cryptate conjugate in lysis buffer are incubated with the treated cells at room temperature for 1 hour. The HTRF signal is detected using an EnVision® plate reader (Perkin-Elmer) to calculate the ratio of fluorescence at 665 nm to 620 nm. The raw data are converted to cAMP amount (pmole/well) using a cAMP standard curve generated for each experiment. Data are analyzed using a 4-parameter nonlinear logistic equation (ABase Equation 205) as shown: $y=(A+((B-A)/(1+((C/x)^D))))$ where, y=% specific inhibition, A=Bottom of the curve, B=Top of the curve, C=Relative $IC_{50}$=concentration causing 50% inhibition based on the range of the data from top to bottom, D=Hill, Slope=slope of the curve.

Following the procedures essentially as described above, the compound of Example 1 has an $IC_{50}$ of 5.6±2.8 nM (n=8) measured at human EP4. This demonstrates that the compound of Example 1 is a potent antagonist of human EP4 in vitro.

In Vitro Rat EP4 Functional Antagonist Activity

Rat EP4 cDNA (Genebank Accession# NM_03276) is cloned into pcDNA 3.1 vector and subsequently transfected in HEK293 cells for receptor expression. Rat EP4 stable clone is scaled up and then frozen down as cell bank for future compounds screening. To test EP4 antagonist compounds in rEP4 cells, thaw the frozen cells and then resuspend cells in cAMP assay buffer. The cAMP buffer is made by HBSS without Phenol Red (Hyclone, SH30268) supplemented with 20 mM HEPES (Hyclone, SH30237), 0.1% BSA (Gibco, 15260) and 125 µM IBMX (Sigma, I5879). The cells are plated into 96-well half area flat-bottom polystyrene black plates (Costar 3694). Compounds are serial diluted with DMSO to give 10-point concentration response curves. Then diluted compounds are added into cAMP assay buffer which contains $PGE_2$ (Cayman 14010, in a concentration predetermined to produce an $EC_{80}$) at ratio of DMSO/buffer at 1/100. The cells are treated with compounds in the presence of $PGE_2$ ($EC_{80}$ concentration) for 30 minutes at room temperature. The cAMP levels generated from the cells are quantified by a cAMP HTRF assay kit (Cisbio 62AM4PEC). The plates are read on an EnVision plate reader using HTRF optimized protocol (PerkinElmer). $IC_{50}$'s are calculated using Graphpad Prism (v. 4) nonlinear regression, sigmoidal dose response curve fitting.

Following the procedures essentially as described above, the compound of Example 1 has an $IC_{50}$ of 12 nM measured at rat EP4. This demonstrates that the compound of Example 1 is a potent antagonist of rat EP4 in vitro.

In Vitro Antagonist Activity in Human Whole Blood

The inhibitory effects of $PGE_2$ on LPS-induced TNFα production from macrophages/monocytes are believed to be mediated by EP4 receptors (See Murase, A., et al., Life Sciences, 82:226-232 (2008)). The ability of the compound of Example 1 to reverse the inhibitory effect of $PGE_2$ on LPS-induced TNFα production in human whole blood is an indicia of functional activity.

Blood is collected from normal volunteer donors into sodium heparin vacutainer tubes. Donors have not taken NSAIDs or celecoxib within 48 hours or glucocorticoids within two weeks of the donation. All tubes/donor are pooled into 50 mL Falcon conical centrifuge tubes and 98 µL/well is distributed into 96-well tissue culture plates (Falcon 3072). Compounds are diluted into DMSO to 100× final and 1 µL/well in triplicate is added to the blood to give 7 point concentration response curves. The blood is pretreated with the compounds at 37° C., in a 5% $CO_2$ humidified atmosphere, for 30 minutes, after which 1 µL/well of a solution of 1 mg/mL of lipopolysaccharide (LPS) (Sigma 0111:B4) in 0.2 mg/mL bovine serum albumin (BSA)/PBS+/−1 mM $PGE_2$ (Cayman 14010) is added to give a final LPS concentration of 10 µg/mL+/−10 nM $PGE_2$. The plates are incubated for 20-24 hours at 37° C. in a 5% $CO_2$ humidified atmosphere. The plates are centrifuged at 1800×g, 10 minutes at 22° C., in an Eppendorf 5810R centrifuge. Plasma is removed from the cell layer and is transferred to v-bottom polypropylene plates. TNFα levels in 2 µL plasma are quantified by a commercially available enzyme immunoassay (R&D Systems DY210), using Immulon 4 HBX plates (Thermo 3855) and 3,3',5,5'-tetramethylbiphenyl-4,4'-diamine substrate (KPL 50-76-03). The plates are read at $A_{450}$-$A_{650}$ on a plate reader (Molecular Devices Versamax) using SOFTmaxPRO (v. 4.3.1) software. $IC_{50}$s are calculated using Graphpad Prism (v. 4) nonlinear regression, sigmoidal dose response curve fitting. Results are expressed as the geometric mean±standard deviation; n=number of independent determinations.

Following the procedures essentially as described above, the compound of Example 1 has an $IC_{50}$ of 123±81 nM (n=8) measured at human EP4. This demonstrates that the compound of Example 1 is a potent EP4 antagonist in the human blood TNFα induction assay.

We claim:

1. A compound of the formula:

wherein A is:

$R^1$ is $CH_3$, $CF_3$, or F;
$R^2$ is H, $CH_3$, or F;
$R^3$ is $CH_3$, $OCH_3$, OH, F;
$R^4$ is OH or $CH_2OH$; and
X is CH or N;
or a pharmaceutically acceptable salt thereof.

2. A compound or salt according to claim 1 wherein A is:

3. A compound or salt according to claim 2 wherein $R^1$ is $CH_3$.
4. A compound or salt according to claim 3 wherein X is N.
5. A compound or salt according to claim 4 wherein $R^2$ is H and $R^3$ is OH.
6. The compound according to claim 1 which is:

or a pharmaceutically acceptable salt thereof.

7. The compound according to claim 1 which is:

8. Hydrated compound according to claim 7.
9. The hydrated compound according to claim 8 characterized by a substantial peak in the X-ray diffraction spectrum, at diffraction angle 2-theta, of 9.0°, in combination with two or more peaks at diffraction angle 2-theta selected from the group consisting of 5.8°, 8.5°, 9.8°, 11.6°, 11.8°, 17.5°, and 24.2°.
10. A method of treating osteoarthritis in a patient, comprising administering to a patient in need of such treatment an effective amount of a compound, or pharmaceutically acceptable salt thereof, according to claim 1.
11. A method of treating rheumatoid arthritis in a patient, comprising administering to a patient in need of such treatment an effective amount of a compound or pharmaceutically acceptable salt thereof, according to claim 1.
12. A method of treating pain associated with osteoarthritis or rheumatoid arthritis in a patient, comprising administering to a patient in need of such treatment an effective amount of a compound or a pharmaceutically acceptable salt thereof, according to claim 1.
13. A pharmaceutical composition, comprising a compound or a pharmaceutically acceptable salt thereof according to claim 1 in combination with one or more pharmaceutically acceptable carriers, diluents, or excipients.

* * * * *

UNITED STATES PATENT AND TRADEMARK OFFICE
CERTIFICATE OF CORRECTION

PATENT NO. : 8,642,768 B2
APPLICATION NO. : 13/922277
DATED : February 4, 2014
INVENTOR(S) : Blanco-Pillado et al.

Page 1 of 1

It is certified that error appears in the above-identified patent and that said Letters Patent is hereby corrected as shown below:

In the Claims

Column 81, lines 44 to 52:

*In Claim 1, delete " 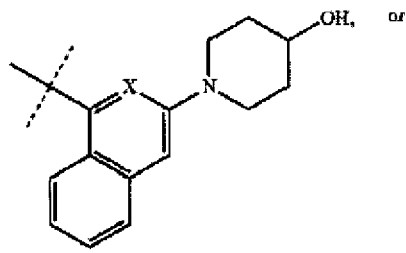 " and

Insert -- 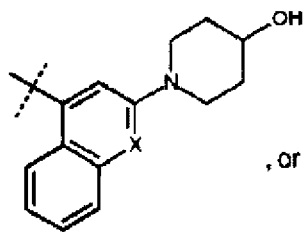 --.

Signed and Sealed this
Sixth Day of May, 2014

Michelle K. Lee
*Deputy Director of the United States Patent and Trademark Office*